United States Patent [19]
Aouni-Ateshian et al.

[11] Patent Number: 6,161,080
[45] Date of Patent: Dec. 12, 2000

[54] THREE DIMENSIONAL MULTIBODY MODELING OF ANATOMICAL JOINTS

[75] Inventors: Gerard H Aouni-Ateshian, New York, N.Y.; Leendert Blankevoort, Nijmegen, Netherlands; S. Daniel Kwak, Brighton, Mass.; Van C. Mow, Briarcliff Manor, N.Y.

[73] Assignee: The Trustees of Columbia University in the City of New York, New York, N.Y.

[21] Appl. No.: 08/972,160

[22] Filed: Nov. 17, 1997

[51] Int. Cl.$^7$ .............................. G06G 7/48; G06G 7/58
[52] U.S. Cl. ................................ 703/11; 703/2; 703/7; 600/587; 623/11
[58] Field of Search ..................... 395/500.28, 500.32; 600/587; 623/11; 703/7, 11, 2

[56] References Cited

U.S. PATENT DOCUMENTS

| | | | |
|---|---|---|---|
| 4,433,961 | 2/1984 | Chandler | 434/274 |
| 5,005,559 | 4/1991 | Blanco et al. | 600/114 |
| 5,041,141 | 8/1991 | Ypma et al. | 623/23 |
| 5,383,454 | 1/1995 | Bucholz | 600/429 |
| 5,433,215 | 7/1995 | Athanasiou et al. | 600/587 |
| 5,445,152 | 8/1995 | Bell et al. | 600/415 |
| 5,503,162 | 4/1996 | Athanasiou et al. | 600/587 |
| 5,522,900 | 6/1996 | Hollister | 623/18 |
| 5,531,520 | 7/1996 | Grimson et al. | 382/131 |
| 5,682,886 | 11/1997 | Delp et al. | 600/407 |
| 5,880,976 | 3/1999 | DiGioia, III et al. | 395/500.28 |

OTHER PUBLICATIONS

Kwak et al., J. Orthop. Res. 15(3): 468–472 (1997).
Blankevoort et al., J. Orthop. Res. 14(4): 676–679 (1996).
Blankevoort et al., J. Biomech. Eng. 113(3): 263–269 (1991).
Ateshian et al., J. Biomech. 24(8): 761–776 (1991).
Roglic et al., ASME Adv. Bioeng 36: 261–262 (Nov. 1997).
Sathasivam and Walker, J. Biomechanics 30: 177–184(1997).
Shelburne and Pandy, J. Biomechanics 30: 163–176(1997).
Wimmer and Andriachhi, J. Biomechanics 30: 131–134(1997).
Grimson et al., IEEE Transactions on Medical Imaging 15(2): 129–140 (Apr. 1996) (Abstract).
Blankevoort and Huiskies, J. Biomechanics 29(7): 955–961(1996).
Kwak et al. ASME BED—Adv. Bioeng. 23: 239–248 (1996).
Beynnon et al., Trans. ASME, J. Biomech. Eng. 118:227–239 (1996).
Cohen et al., ASME BED—Adv. Bioeng. 33:387–388 (1996).
Blankevoort et al., European Society of Biomechanics 10:260(1996).

(List continued on next page.)

*Primary Examiner*—Eric W. Stamber
*Assistant Examiner*—Samuel Broda
*Attorney, Agent, or Firm*—Baker Botts LLP

[57] ABSTRACT

The present invention relates to a method of generating a three dimensional representation of one or more anatomical joints, wherein the representation comprises two or more movable bodies and one or more links, comprising the steps of inputting anatomically representative data of two or more movable bodies of the selected joint or joints; selecting one or more link types responsive to the representative data of the bodies; selecting link characteristics responsive to each selected link type; generating an equilibrium condition responsive to interaction between the bodies and the links; and displaying a three dimensional representation of the selected joint or joints responsive to the data generated from the equilibrium condition of the anatomical joint or joints. The present invention further relates to a system for generating a three dimensional representation of one or more anatomical joints, and a method of planning surgery of one or more anatomical joints.

13 Claims, 25 Drawing Sheets

Microfiche Appendix Included
(1 Microfiche, 128 Pages)

OTHER PUBLICATIONS

Kwak et al., Annals of Biomedical Engineering, vol. 23, p. S–106, Abstract 498 (Suppl. 1. 1995).
Kwak et al. ASME BED—Adv. Bioeng. 31:309–310 (1995).
Heegaard et al., J. Biomechanical Eng., 28:1265–1279 (1995).
Heegard and Leyvraz, ASME, Bioeng. Conference, 29:221–222 (1995).
Eng and Winter, J. Biomechanics, 28: 753–758 (1995).
Woltring, J. Biomech. 27:1399–1414 (1994).
Buckwalter et al., J. Am. Acad. Orthop. Surg. 2:192 (1994).
Gardner, et al., ASME, BED Adv. Bioeng. 28:279–280 (1994).
Delp et al., J. Orthop. Res., 12: 860–870(1994).
Delp et al., J. Orthop. Res., 13: 96–104(1994).
Delp et al., J. Biomechanics, 27:1201–1211 (1994).
Tumer and Engin, Trans. ASME, J. Biomech. Eng. 115:350–356 (1993).
Hirokawa, Crit. Rev. Biomed. Eng., 21(2): 79–135 (1993).
Engin and Tumer, Trans. ASME, J. Biomech. Eng. 115:137–143 (1993).
Hefzy and Yang, J. Biomed. Eng., 15:289–302 (1993).
Abdel–Rahman and Hefzy, J. Biomechanical Eng., 115:357–365 (1993).
Loch et al., J. Biomechanics, 25:81–90 (1992).
Hirokawa, J. Biomechanics, 25:1393–1401 (1992).
Hawkins, Comput. Biol. Med. 22: 59–71(1992).
Landjerit and Thourot, Acta Orthopaedica Belgica, 58: 113–121 (1992) (English summary).
Hirokawa, J. Biomechanics, 24:659–671 (1991).
Blankevoort et al., J. Biomechanics, 24:1019–1031 (1991).
Thompson et al., Am. J. Sports Med. 19:210–216 (1991).
Fulkerson, et al., Am. J. Sports Med. 18:490–496 (1990).
Delp et al., IEEE Trans. Biomed. Eng., 37: 757–766 (1990).
Lengsfeld et al., Arch. Orthop. Trauma Surg. 109: 280–283 (1990).
Garg and Walker, J. Biomechanics 23: 45–88 (1990).
Yamaguchi and Zajac, J. Biomechanics 22: 1–10 (1990).
Apkarian et al., J. Biomechanics 22: 143–155 (1989).
Essinger et al., J. Biomechanics, 22:1229–1241 (1989).
Bradley et al., J. Bone Joint Surg. 70–B: 94–99 (1988).
Hirokawa, Keisoku Jido Seigyo Gakkai Ronbunshu, 24: 72–78 (1988) (English Abstract).
vanEijden et al., Acta Orthop. Scand. 58: 560–566 (1987).
Hirokawa, Keisoku Jido Seigyo Gakkai Ronbunshu, 22: 84–91, (1986) (English Abstract).
Olney and Winter, J. Biomechanics 18: 9–20 (1985).
Huskies et al., J. Biomechanics 18: 559–570 (1985).
Moeinzadeh et al., J. Biomechanics 16: 253–264 (1983).
Andriacchi et al., J. Biomechanics 16: 23–29 (1983).
Wismans et al., J. Biomechanics, 13:677–685 (1980).
Maquet, Clin. Orthop. 115:225–230 (1976).
Crowninshield et al., J. Biomechanics 9: 397–405 (1976).

THREE DIMENSIONAL MULTIBODY MODELING OF ANATOMICAL JOINTS

A portion of the disclosure of this patent document contains material which is subject to copyright protection. The copyright owner has no objection to the facsimile reproduction by anyone of the patent document or the patent disclosure, as it appears in the Patent & Trademark Office file or records, but otherwise reserves all copyright rights whatsoever.

A microfiche Appendix containing source code listing utilized in practicing the invention is included as part of the Specification and is hereinafter referred to as Appendix I. Appendix I includes twelve microfiche labeled 1 to 12 with 1,128 frames, 98 frames on microfiche numbered 1 through 11, respectively, and 50 frames on microfiche numbered 12.

1. INTRODUCTION

This invention relates to a three dimensional software model of an anatomical joint, which predicts the quasi-static kinematic orientation and position of movable bodies. More particularly, the invention relates to a three dimensional software model that predicts contact forces, contact areas and ligament forces, and which can be used to simulate pathologies and surgical procedures.

2. BACKGROUND OF INVENTION

Attempts have been made to model anatomical joints involving two dimensional models and three dimensional models. Nonetheless, serious limitations exist for the existing modeling systems because they are limited to analyzing only two movable bodies. Models that disclose modeling of three bodies must restrict the movability of at least one of the bodies.

Software modeling is generally considered to be preferred to the testing of real joints. When using actual joints, only a limited number of parameters can be studied from a particular set of experiments. If a function of a joint structure is studied by altering the structure (e.g., transecting a ligament), any other variables that are affected by the altered structure can no longer be studied within the same joint without somehow restoring the structure. Since most cadaveric experiments are conducted to perform invasive procedures that destroy the specimen, usually another specimen must be instrumented and tested to examine new parameters, making comparisons of results with previous experiments more difficult since experiments were performed on different joints. Furthermore, to investigate a particular pathology of a joint, either specimens exhibiting that pathology must be found, or the pathology must be physically simulated on a normal joint; both of these options are often difficult. Using a software model, functions of various structures can be studied by removing, restoring, or altering the structure without destroying the original model and can be used indefinitely. Furthermore, a software model can be used to simulate a surgical procedure by examining the interaction between different parameters, particularly with regard to internal forces, such as articular contact forces or ligament tension. A model may further be used as a research tool and a design tool. Effectiveness of various surgical procedures can be explored and evaluated by simulating the surgery with the mathematical model. Prostheses and other medical instruments may be more efficiently designed and evaluated using a model. A model can even aid in the design of new cadaveric experiments by first exploring different design parameters and identifying the most important parameters to be tested.

Of the anatomical joints, the human knee joint with its complex three-dimensional motion and irregular contacting surfaces, has been commonly modeled.

2.1 Two Body Models

Two dimensional models have been designed to analyze two bodies. Two dimensional models of the patellofemoral joint have calculated the contact force in the patellofemoral joint at a given joint pose (i.e., both the position and orientation) by using a sagittal plane. In such a model, the femur is fixed, and the insertion location of the patellar ligament on the tibia is prescribed as a function of knee flexion. The patella is loaded with a single quadriceps force, and the patellar ligament is simulated by a line segment. Such a two-dimensional model predicts patellar pose, contact forces, and ligament forces by solving force and moment equilibrium conditions at each knee flexion angle.

In another two dimensional model of the patellofemoral joint using a sagittal plane, the tibia is fixed and the motion of the femur is prescribed. At a given knee flexion angle, the pose of the patella is adjusted to contact the femur. The profile of the patellar surface is simplified as a straight line, and the profile of the femoral surface is described by elliptical curves. A single quadriceps force is applied on the patella, and the patellar ligament is simulated as an inelastic line segment.

In another two dimensional model, the patellofemoral joint is simulated in the horizontal plane. The outline of the patellar and femoral surfaces are represented as outline curves that are smoothed iteratively using spline functions.

In all of above two dimensional models, the articular surface contact was modeled as a point contact between two rigid surfaces. None of the above two dimensional models are capable of modeling any number of moving bodies, and none simulate the wrapping of bodies around other bodies.

Three dimensional models have been construction of the tibiofemoral joint. In one model, the geometry of articular surfaces are represented as rigid surfaces contacting only at two points on the medial and lateral sides of the surface. A quadriceps force is applied through a set of two lines, and the patellar ligament is simulated by a set of two springs. This model employs geodesic line theory to model the quadriceps tendon wrapping around the femoral trochlear surface at high angles of knee flexion.

In a three-dimensional model of the patellofemoral joint, all structures were assumed to be rigid, including articular surfaces and ligaments. However, both the quadriceps tendon and the patellar ligament were modeled as a single line segments. This model did not simulate wrapping of the quadriceps tendon around the femur; hence, it only simulated the patellofemoral joint at lower angles of knee flexion.

In another three dimensional model of the human knee, the contact of articular surfaces was treated as a deformable contact. Articular surfaces were allowed to overlap each other, and the contact force and area was calculated as a function of the surface overlap. The surfaces of the articular bodies were curved surface approximations. According to this model, the surface displacement is measured by the sum of the relative tibial and femoral surface displacements, which is obtained by the surface penetration of the undeformed tibial and femoral surfaces. However, this articular surface overlap model is limited to an analysis of only two bodies. The model does not provide for the introduction of any number of additional bodies. The model further does not disclose or suggest that the overlap between articular surfaces be measured at each point on the surface of one or the other of the articular bodies, wherein the magnitude of the surface traction due to the surface contact is calculated as a function of combining the contact forces from all points on one of the surfaces, and wherein the surfaces of the articular bodies reflect real anatomical surfaces.

It is further known in the art to use a finite element method (FEM) analysis to simulate the patellofemoral joint in a three dimensional model. In a FEM model, the quadriceps tendon and the patellar ligament are each simulated by a set of three line elements, and the direction of the quadriceps tendon force is varied to accommodate quadriceps tendon wrapping around the femur. The analysis predicted the pose of the patella, stress on the articular surface, and stress inside the patella bone.

In all of the above three-dimensional models, the femur is fixed, while the patella is free to move, and the poses of the tibia were prescribed at various knee flexion angles from experimental results.

Models of the tibiofemoral joint have applied a stiffness model. In one model, the tibiofemoral joint is modeled as two rigid bodies connected by multiple springs. These springs represent different ligaments in the joint, while contact between articular surfaces is not specifically modeled. The stiffness of the joint at different flexion angles is calculated by applying various forces and torques on the model, and the role of a ligament is investigated by selectively eliminating it from the model. In another model, various ligaments and capsular structures in the tibiofemoral joint were simulated as spring elements and were modeled by the mechanical behavior of the joint using a direct stiffness formulation from structural mechanics. Contact between two articular surfaces were included as hydrostatic elements, and curved surfaces were not simulated in the model. In another model, the entire tibiofemoral joint, except for a single ligament and cartilage surfaces, was modeled as a single general stiffness matrix in order to investigate the role of the single ligament in the joint. The geometries of the cartilage surfaces are simplified as spheres for the femur and planes for the tibia. Furthermore, this model is valid only for a small deviation from the experimentally measured equilibrium pose.

In another three dimensional model of the tibiofemoral joint, the model took into account the geometry of the joint surfaces as well as the geometry and material properties of the ligaments and capsule. The position of a large number of point s on the joint surfaces were measured and the geometry of these surfaces were approximated by polynomials in space. The articular surfaces were modeled as rigid surfaces and the ligaments as nonlinear springs. The model calculated internal forces and bone poses by solving the static equilibrium condition at each knee flexion angle. According to the model, the outer surface of each of the condyles of the femur and tibia are simulated by a curved rigid surface, while the contact areas between the femur and tibia are reduced to contact points. The description of the joint surfaces is achieved through the use of dial gauges placed on the joint surfaces to generate coordinates. The contact points on the surfaces of the joint surfaces are determined by an analysis of the flexion extension angle.

In another model of the tibiofemoral joint, the articular surfaces were allowed to overlap each other, and the contact force and area were calculated as a function of the surface overlap. In this model the tibial colateral ligament (also called the medial colateral ligament) was simulated to wrap around the tibial bone surface. In both models, the geometry of the articular surfaces was obtained using a stereophotogrammetric method, and initial lengths of various ligaments were optimized by matching the kinematics of the knee to experimental data.

In another model, a two-dimensional model of the tibiofemoral joint was created using the rigid body spring model that calculated contact force and area as a function of the proximity between two rigid surfaces. The model used an outline of the articular surfaces obtained from a frontal radiograph, and predicted changes in the articular contact pressure as a result of knee osteotomy.

2.2 Three Body Models

Three body models have been developed simulating all three bones in the knee joint. However, simplifications of the anatomical accuracy of the surfaces of the bodies and restrictions of the moveability of the third body have been made.

In one model, a condylar-type knee prosthesis was modeled using a minimum energy principle. Although the patella was included in the model, the motion of the patella was prescribed; hence, it could not deviate from the set path. Furthermore, the geometry of the patellar surface was simplified as a plane, and the patella was not allowed to tilt or rotate internally or externally.

In another model, all three bones in the knee joint were modeled but the tibia was fixed, and the motion of the femur was prescribed. The pose of the patella was prescribed and further adjusted to provide contact with the femur.

In another model, the entire lower extremity including both the knee and hip were simulated to investigate problems in lower extremity. However, this model prescribed the motion of all bones in a certain trajectory; thus, the model could not predict changes in motion of the bones as a result of chances in model parameters, and it did not simulate contact between different articular surfaces.

All of above three body models require a restriction of some or all degrees-of-freedom of one or more of the bodies in order to accommodate the three bones in the joint. The simplifications in the joint geometry and inability to model any number of bodies in one or more joints are serious limitations on the existing models.

2.3 Dynamic Models

Dynamic models have been developed to accommodate surface geometry of bones and ligaments, and to incorporate many movable bodies. Most of the existing dynamic models of anatomical joints are limited to a two dimensional analysis due to the complexity of the calculations needed for dynamic analysis.

In a two dimensional dynamic model of the tibiofemoral joint, a rigid contact between articular surfaces was assumed, and ligaments were modeled as nonlinear elastic springs. In another model, the impact force applied to the joint was simulated. In another two dimensional model, the patella was introduced as third body. In a two dimensional model of the tibiofemoral joint, point contact between two rigid bodies calculations was described.

Although dynamic models have many advantages over static or quasi-static models, their calculations are much more complicated and time consuming. Dynamic models require additional material constants such as damping coefficients, as well as mass and inertia properties. Three dimensional dynamic models have even greater limitations of time and accuracy than two dimensional dynamic models. In order to modify a dynamic model to use it as a static or quasi-static model, artificial values must be assigned to the dynamic forces, such as mass and inertia, therefore deviating from the accuracy of the model.

A serious limitation of existing models is an inability to incorporate accurate anatomical information into the model. Simplifications are made to the anatomy of the body structures requiring artificial compensation in the model to align the results of the model with experimental data.

3. SUMMARY OF THE INVENTION

This present invention provides an accurate three dimensional software model of anatomical joints, which predict the quasi-static kinematic orientation and position of any number of movable bodies, as well as predicting contact forces, contact areas and ligament forces. The software model of the present invention, which can be used to simulate pathologies and surgical procedures, provides a three dimensional multibody model capable of simulating multiple bodies within any particular joint, and is capable of simulating multiple bodies within multiple joints. The present invention incorporates anatomically accurate joint geometry and wrapping of ligaments and tendons around bony or articular surfaces. In accordance with the present invention, the multibody model predicts an equilibrium orientation, contact areas, contact forces, and ligament forces resulting from an interaction between the bodies and links. This graphics based interactive model allows a user easily to modify the input parameters, to designate one or more joints, to select the characteristics of one or more bodies or links between the bodies, and thereafter to almost immediately view the results in a three dimensional display.

It is an object of the present invention to provide a three dimensional software model that predicts the quasi-static kinematic orientation and position of any number of movable bodies.

It is an object of the present invention to provide a three dimensional software model that predicts contact forces, contact areas and ligament forces of any number of movable bodies.

It is an object of the present invention to provide a three dimensional software model that calculates surface stresses of rigid bodies by functions of penetration distances of their irregular three dimensional surfaces, wherein the overlap between articular surfaces is measured at each point on the surface of one or the other of anatomically accurate articular bodies.

It is an object of the present invention to provide a three dimensional software model that simulates the wrapping of bodies around irregular bodies through the use of particle bodies.

It is an object of the present invention to provide a three dimensional software model wherein unknown degrees of freedom are determined by solving equations of static equilibrium forces and moments for all bodies.

It is an object of the present invention to provide a three dimensional software model wherein internal forces resulting from an interaction between the multiple bodies are automatically determined.

It is an object of the present invention to provide a three dimensional software model wherein external forces and moments may be applied.

It is an object of the present invention to provide a three dimensional software model wherein any translational or rotational degree of freedom may be constrained.

It is an object of the present invention to provide a three dimensional software model that can model multiple bodies of a single joint, and multiple bodies of multiple joints.

It is a further object of the present invention to provide a three dimensional software model that models one or more human joints, such as the ankle, knee, hip, wrist, elbow and shoulder.

4. BRIEF DESCRIPTION OF THE DRAWINGS

Further object, features and advantages of the invention will become apparent from the following detailed description taken in conjunction with the accompanying figures showing illustrative embodiments of the invention, in which:

FIG. 1 illustrates the two types of moving bodies represented in the multibody model.

Figure 2:
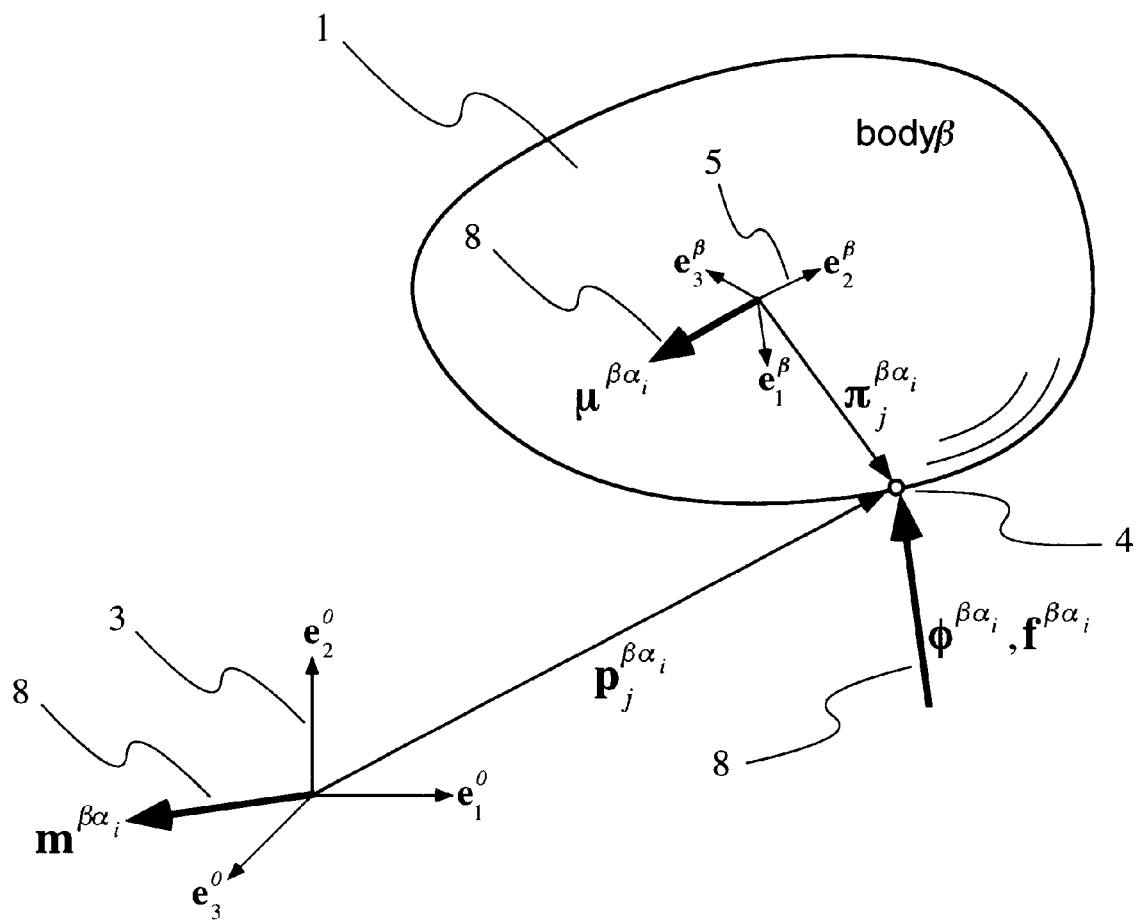

FIG. 2 illustrates the various vectors expressed in two different coordinate systems. Position vector ($\pi_j^{\beta\alpha_i}$) force vector ($\phi^{\beta\alpha_i}$), and moment vector ($\mu^{\beta\alpha_i}$) in the local body-fixed coordinate system ($e_k^\beta$) and related vectors ($P_j^{\beta\alpha_i}$, $f^{\beta\alpha_i}$, and $m^{\beta\alpha_i}$) in the global ground-fixed coordinate system ($e_k^o$) are shown.

Figure 3:
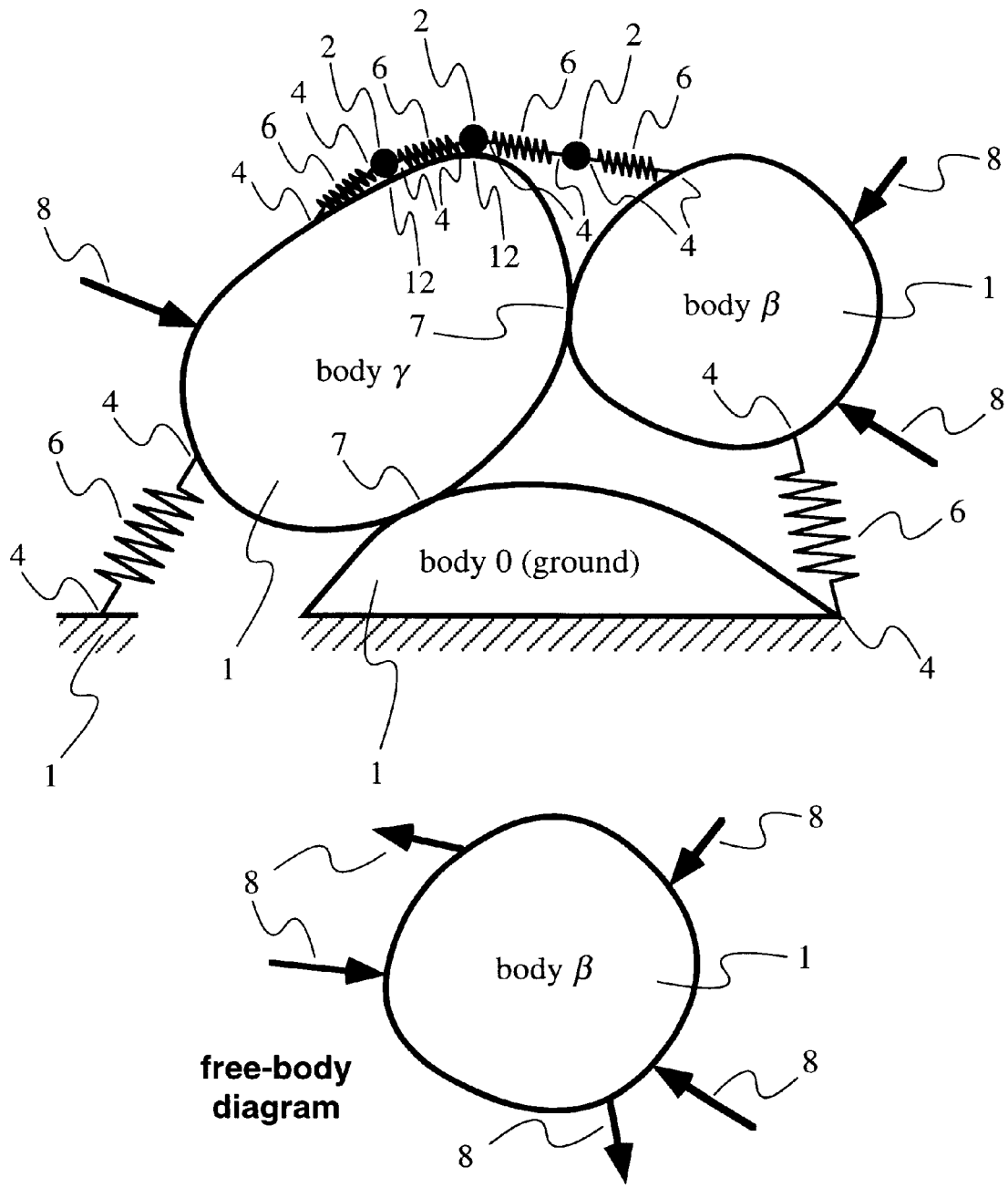

FIG. 3 illustrates that at the convergence of the multibody model, the sum of all forces and the sum or all moments acting on each body must equal be zero.

Figure 4:
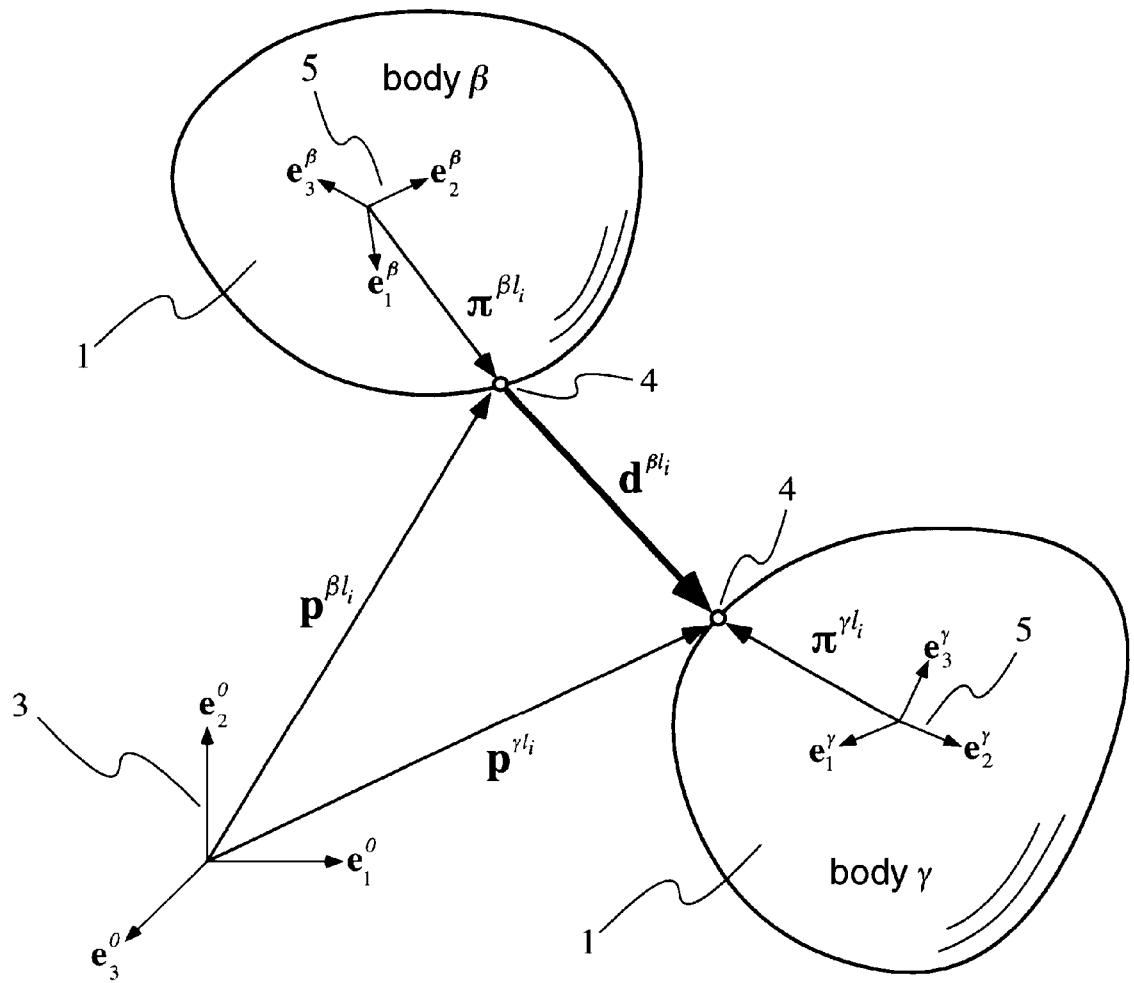

FIG. 4 illustrates a schematic of a ligamentous link between bodies β and γ of a multibody joint model.

FIG. 5 illustrates a tendon-pulley link passing through multiple joints.

Figure 5A:
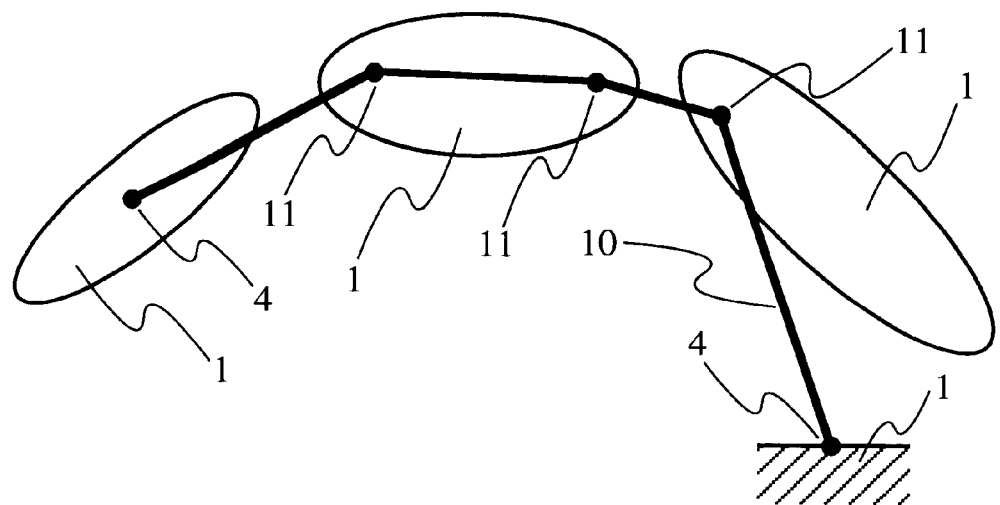

FIG. 5A shows the tendon passing though frictionless pulleys attached to a body in a schematic diagram.

Figure 5B:
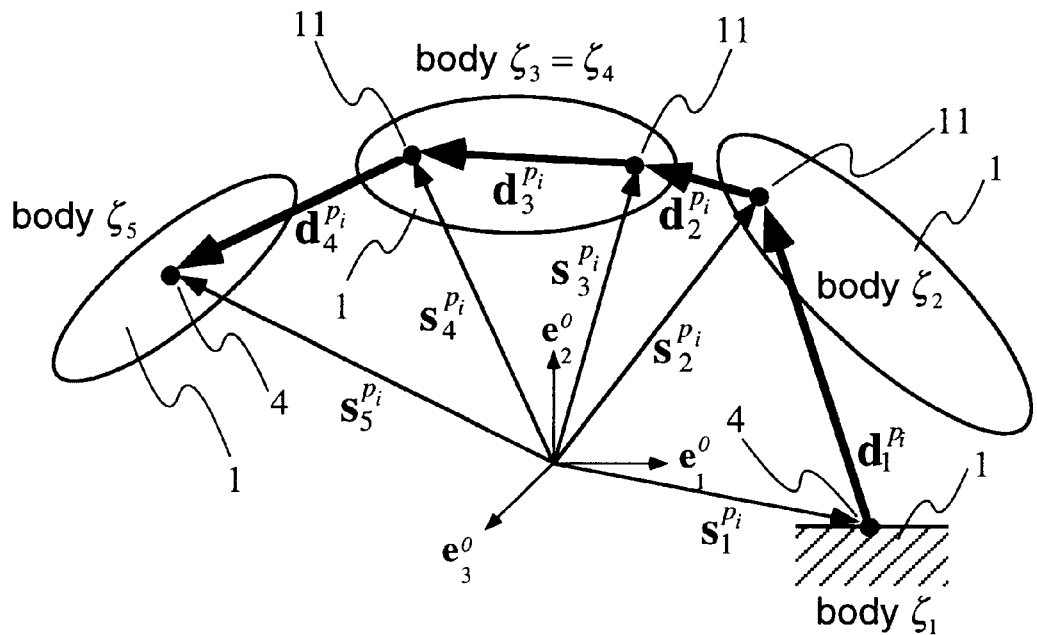

FIG. 5B shows vectors and bodies and

Figure 5C:
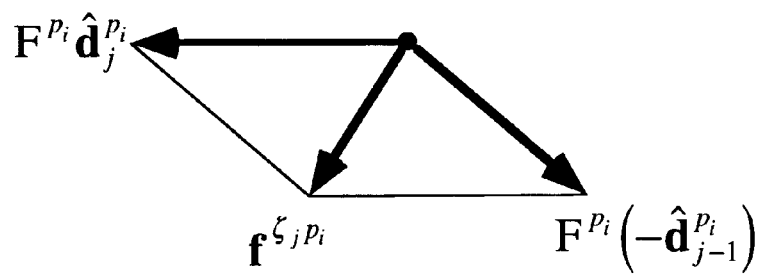

FIG. 5C shows the force on a pulley as a result of tendon passing through.

FIG. 6 illustrates the contact area between two surfaces which is determined by the region of overlap, and the contact force applied at each point on the surface is proportional to the amount of overlap.

Figure 6A:
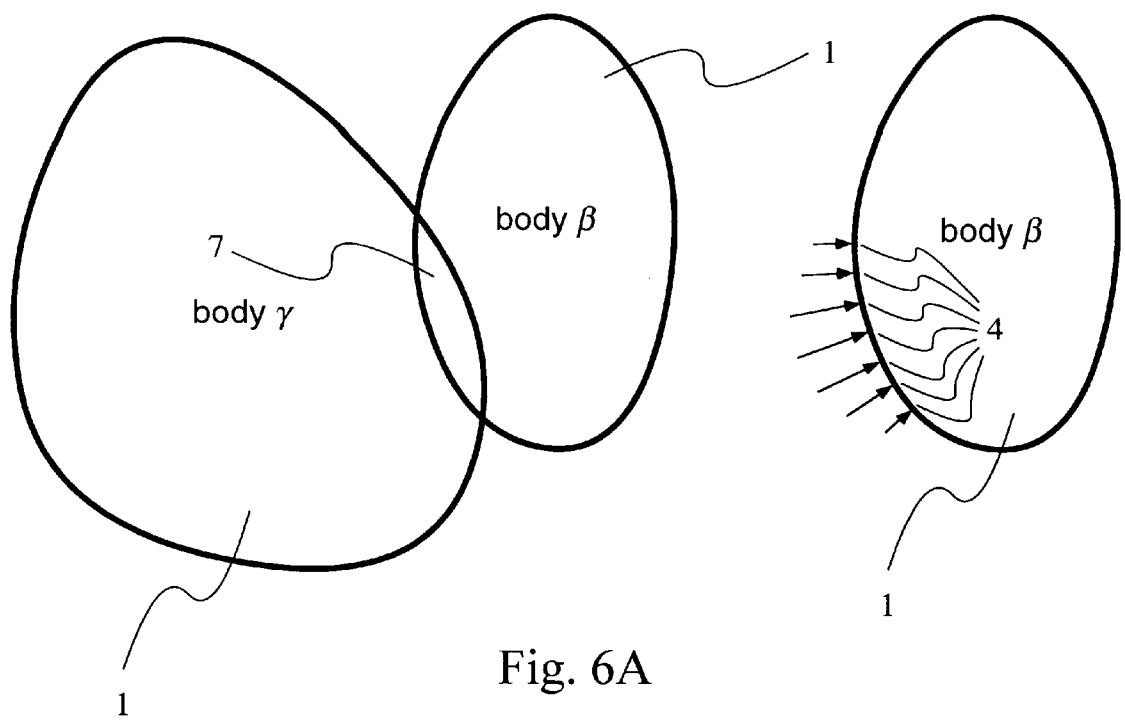

FIG. 6A represents a schematic diagram of contact between two surfaces and

Figure 6B:
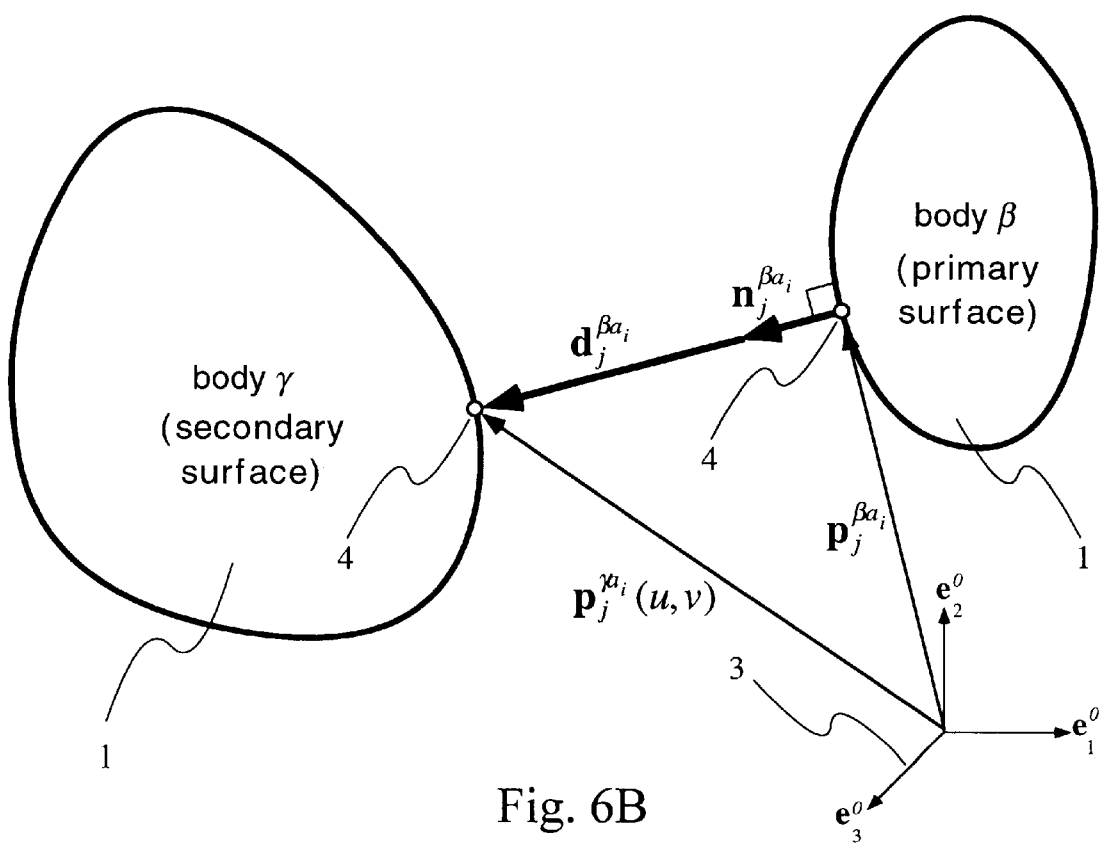

FIG. 6B represents an exploded view with vectors labeled as they appear in the text.

FIG. 7 illustrates a ligament or tendon wrapping around a surface is simulated by imbedding particles in the ligament or tendon, and letting these particles interact with the surface.

Figure 7A:
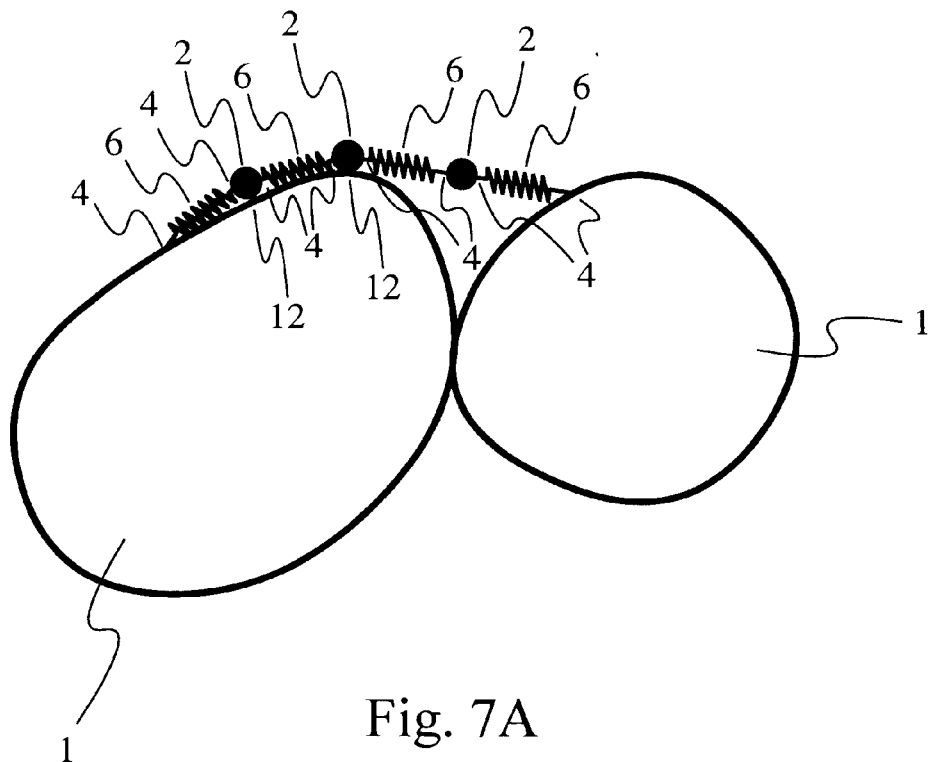

FIG. 7A represents a schematic diagram of a ligament wrapping a surface and

Figure 7B:
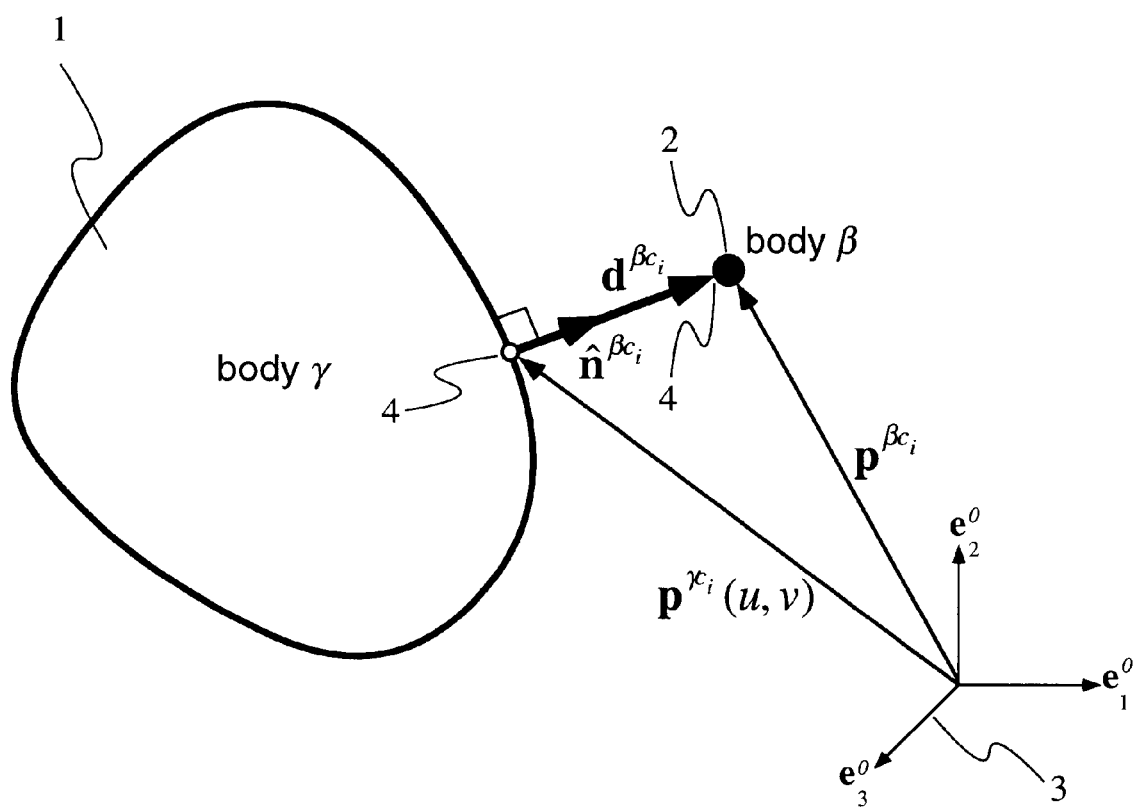

FIG. 7B represents vectors for the particle and surface labeled as they appear in the text.

FIG. 8 illustrates external forces and moments applied directly on a body.

Figure 8A:
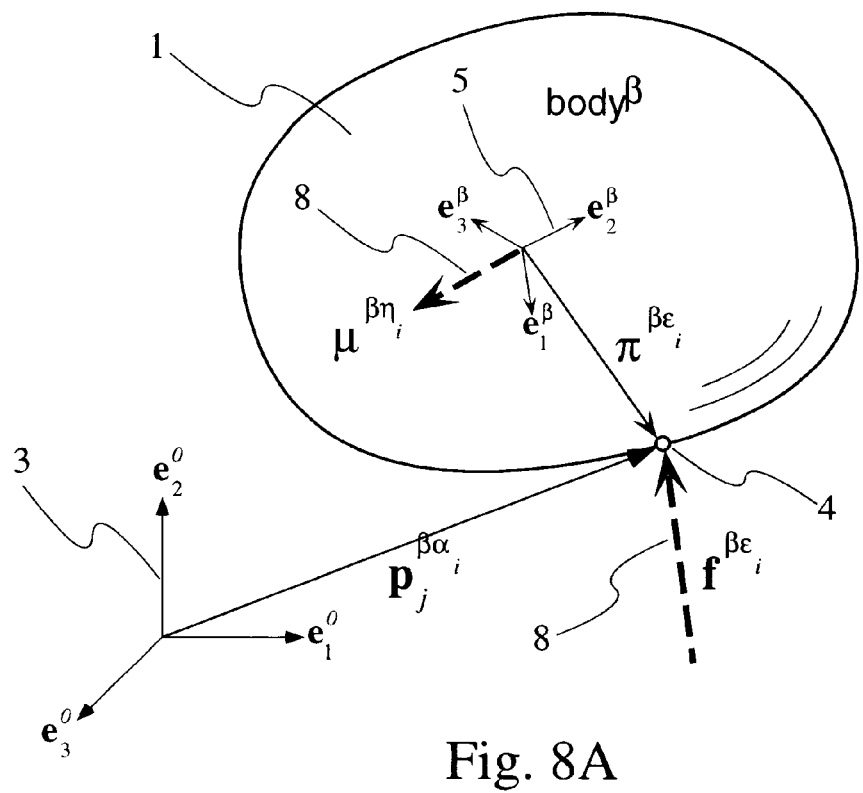
Figure 8B:
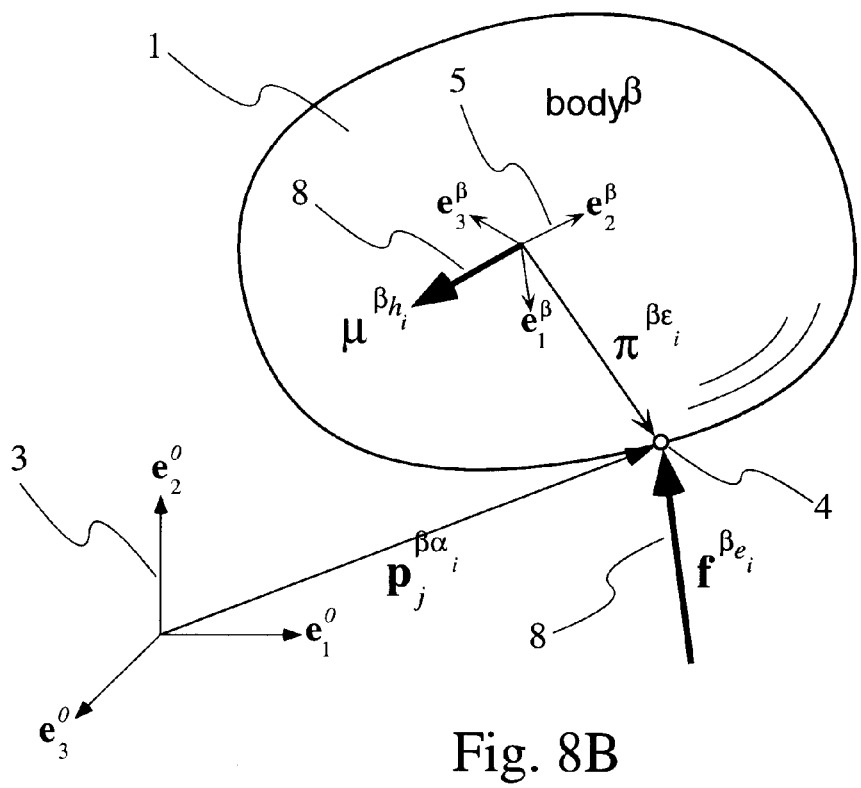

FIG. 8A represents a force and moment fixed to the local body-fixed coordinate system, as noted by dashed lines and different arrow head type, and FIG. 8B represents a force and moment fixed to the global ground-fixed coordinate system.

Figure 9:

FIG. 9 illustrates a display of the multibody model program wherein the user can interact with the program through various menus and windows.

Figure 10:
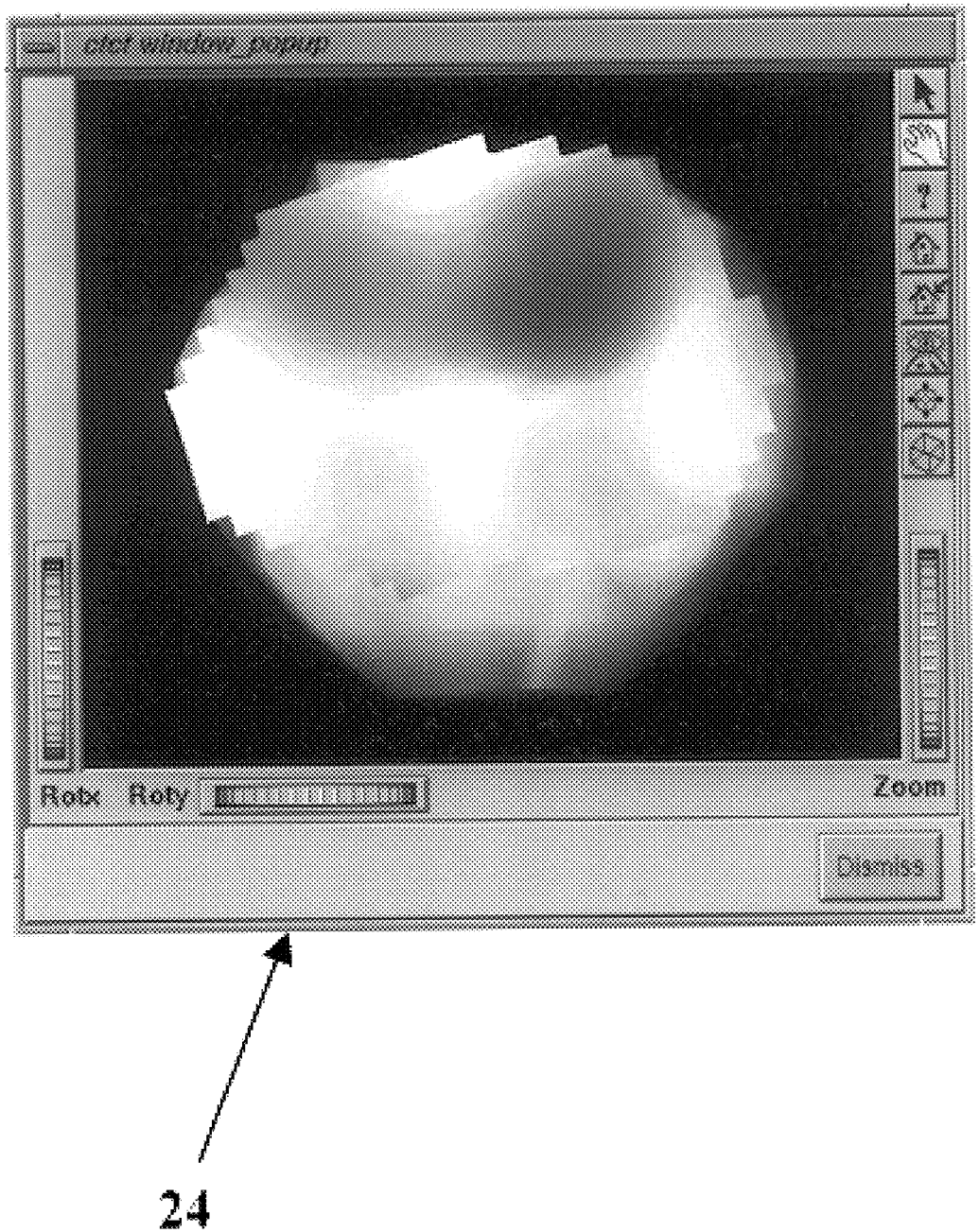

FIG. 10 illustrates a window of the multibody model program, displaying contact area of a patella.

FIGS. 11A–C illustrates the various views of the patellofemoral joint at 90° of knee flexion. Note that the quadriceps tendons wrap around the femoral surface at this flexion angle.

FIGS. 12A–E illustrates multibody models from five of the six knees employed in the validation study. Each model is based on the specific geometry of the individual specimens.

Figure 13:
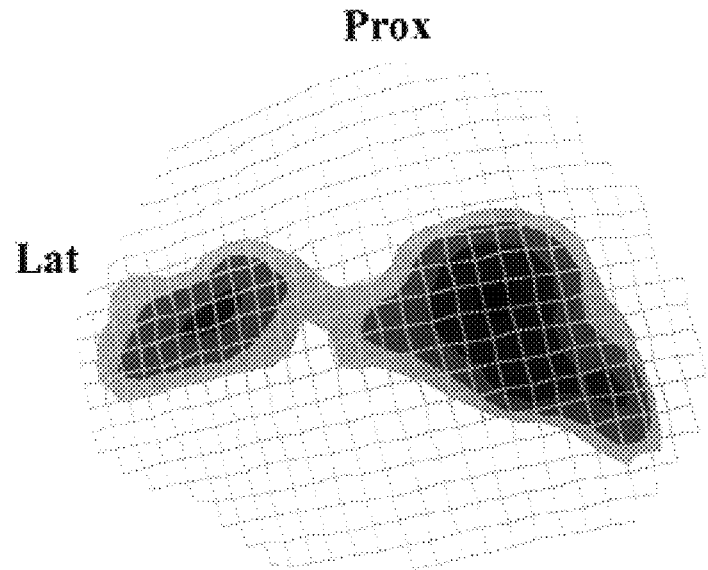
Figure 13:
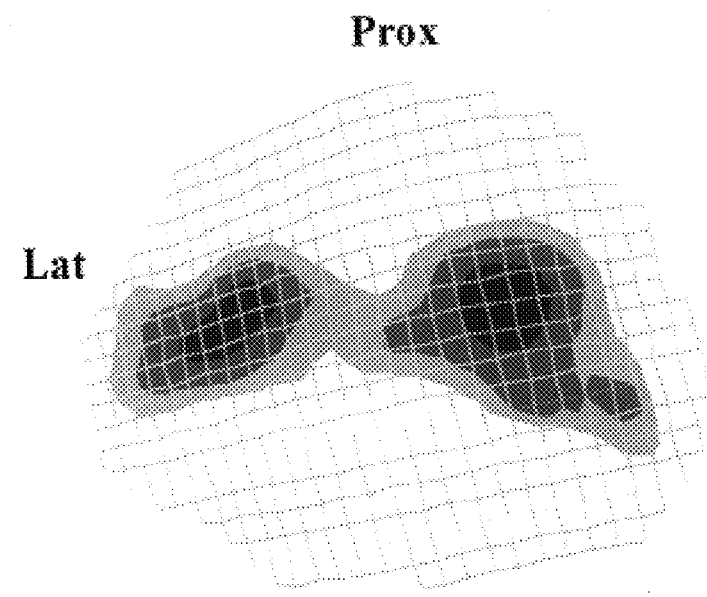
Figure 13:
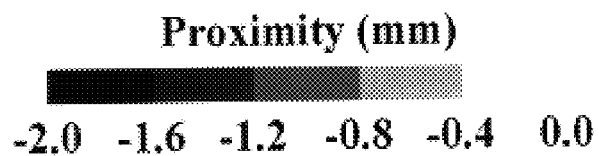

FIG. 13 illustrates the contact areas of the patellofemoral joint at 45° knee flexion, comparing experimental results and multibody model predictions.

Figure 14:
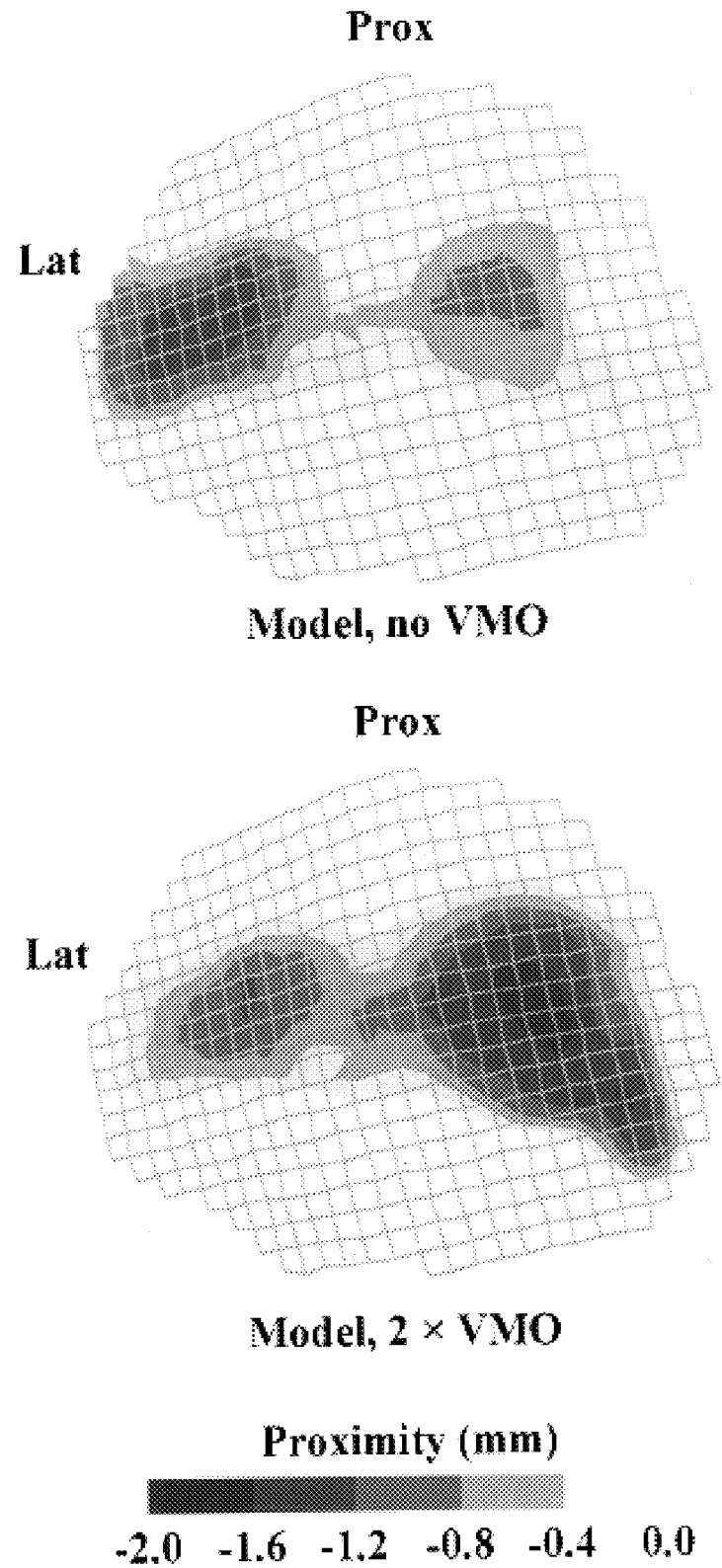

FIG. 14 illustrates the patella contact area at 45° of knee flexion, predicted by the multibody model for the configurations of no VMO force, and twice the VMO force, relative to the configuration of FIG. 13.

Figure 15:
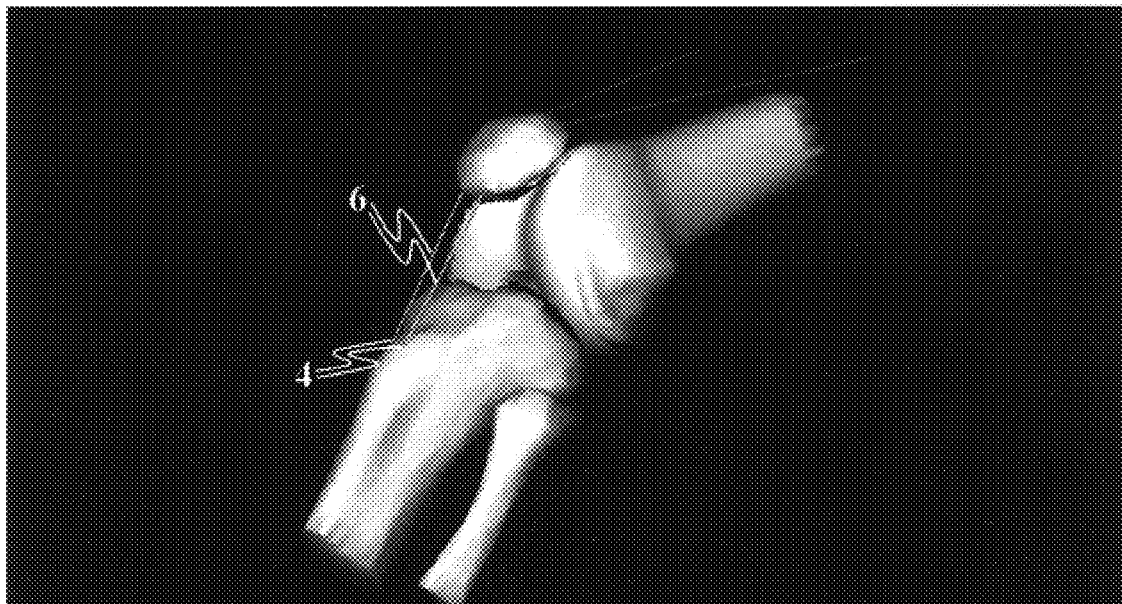
Figure 15:
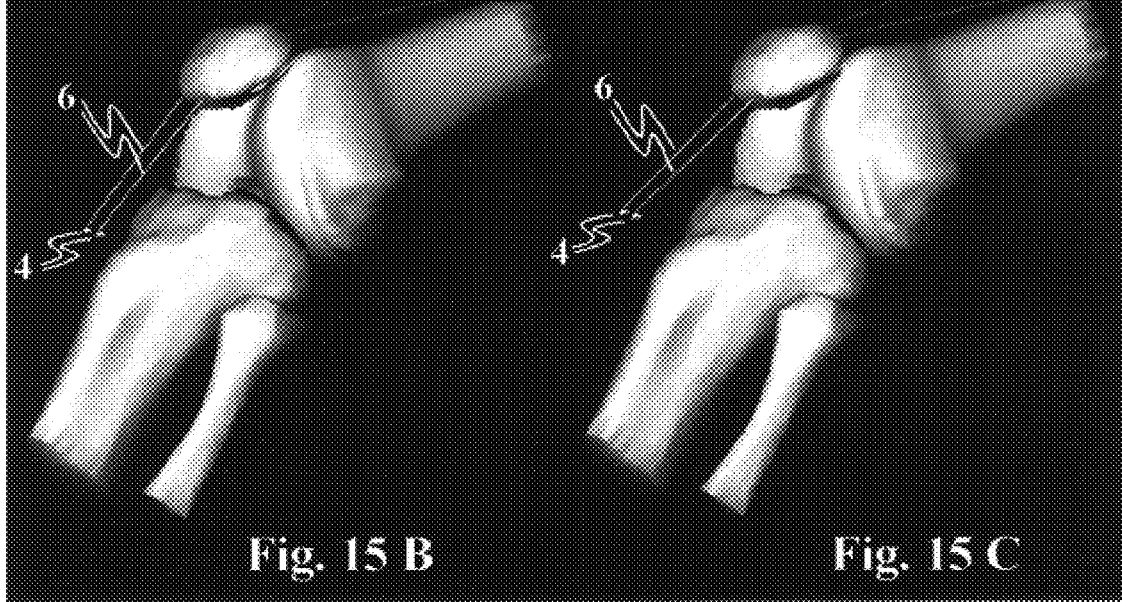

FIG. 15 illustrates the multibody model simulation of a Maquet procedure on a typical knee.

FIG. 15A shows pre-operative configuration,

FIG. 15B shows 15 mm anterior transfer, and

FIG. 15C shows 25 mm anterior transfer.

Figure 16:
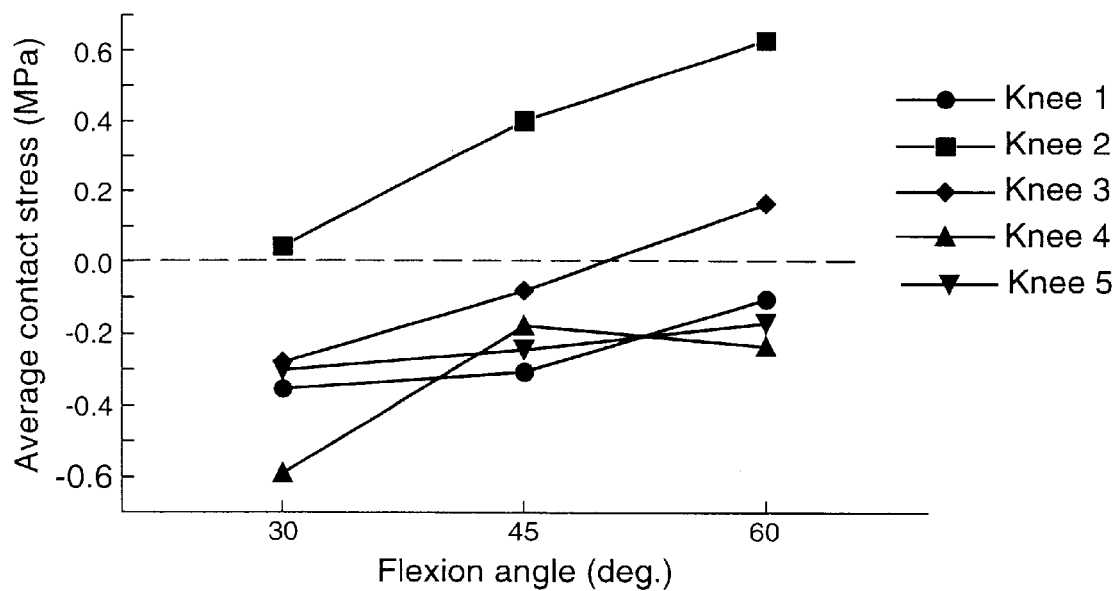

FIG. 16 illustrates the changes in the average contact stress of the patellofemoral joint following 25.0 mm anterior transfer of the tibial tuberosity (Maquet procedure), predicted from the multibody model analysis.

Figure 17:
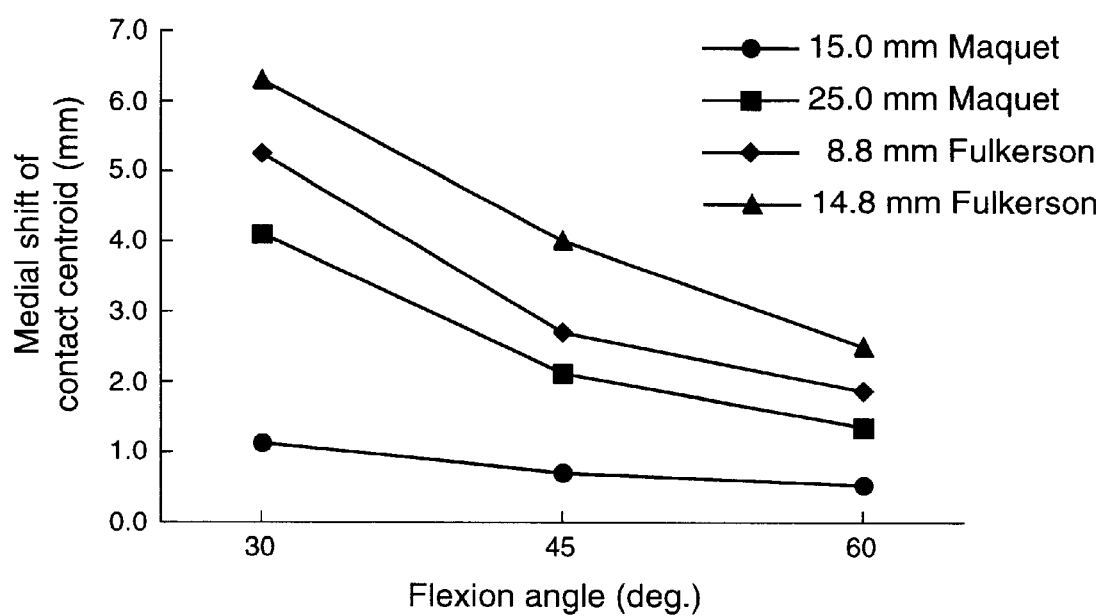

FIG. 17 illustrates the medial shift in the centroid of the patellofemoral joint contact area following Maquet and Fulkerson procedures as predicted by the multibody model.

Figure 18:
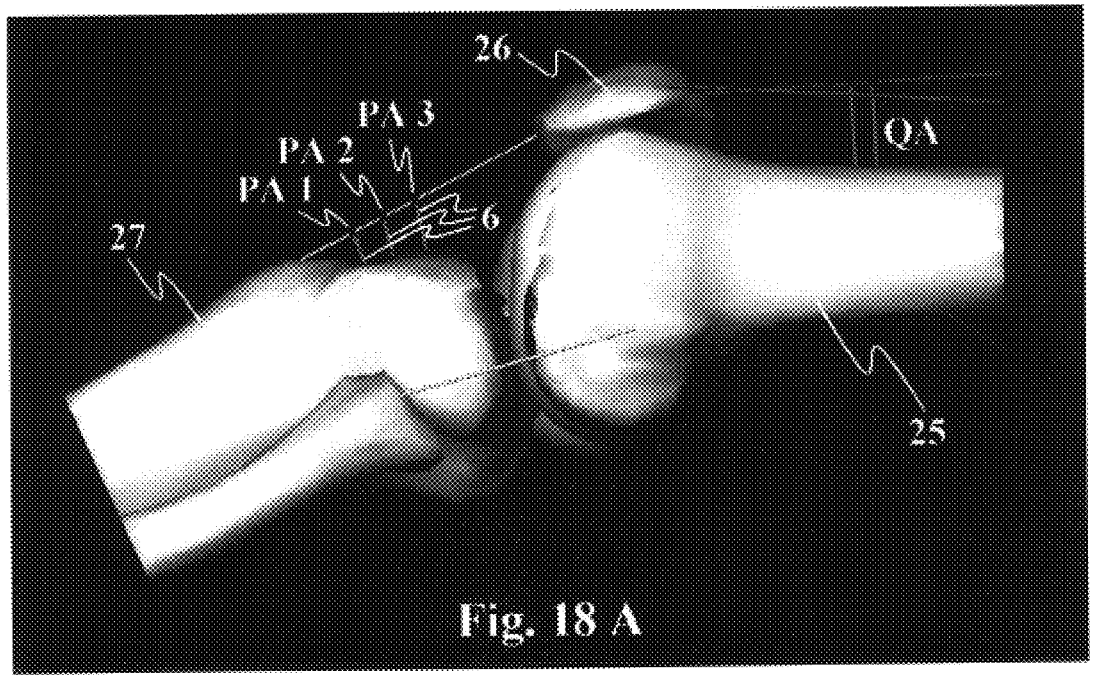
Figure 18:
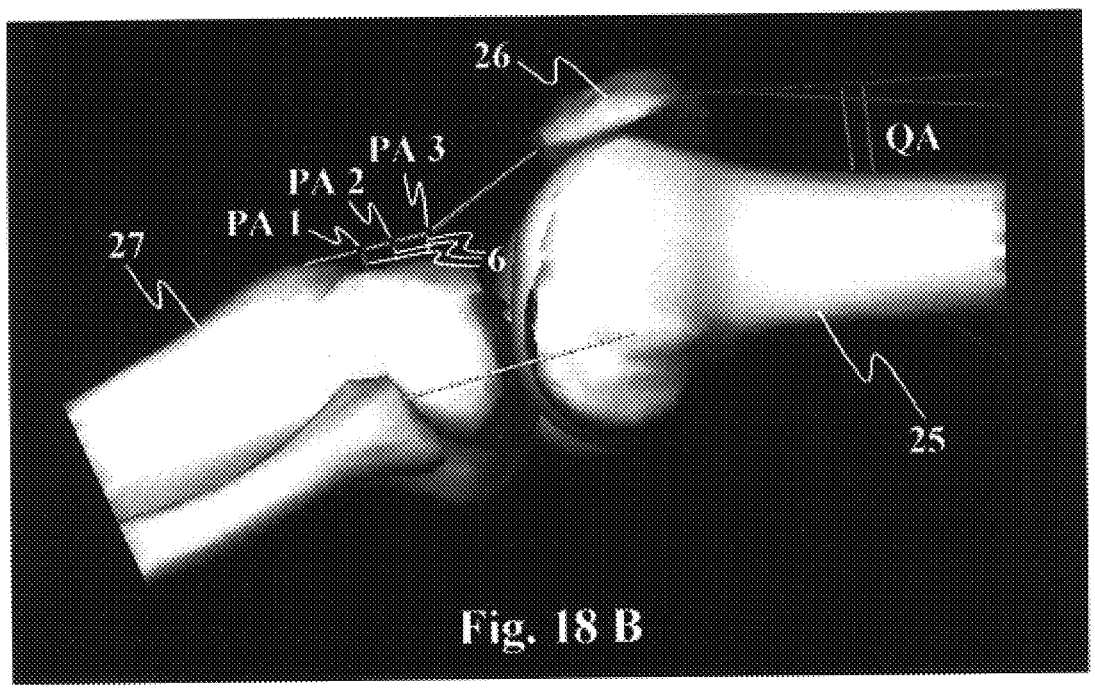

FIG. 18 illustrates the multibody model of patellar and quadriceps tendon adhesions.

FIG. 18A shows normal configuration.

FIG. 18B shows configuration with patellar tendon adhesion (PA1, PA2 and PA3).

Figure 19A:
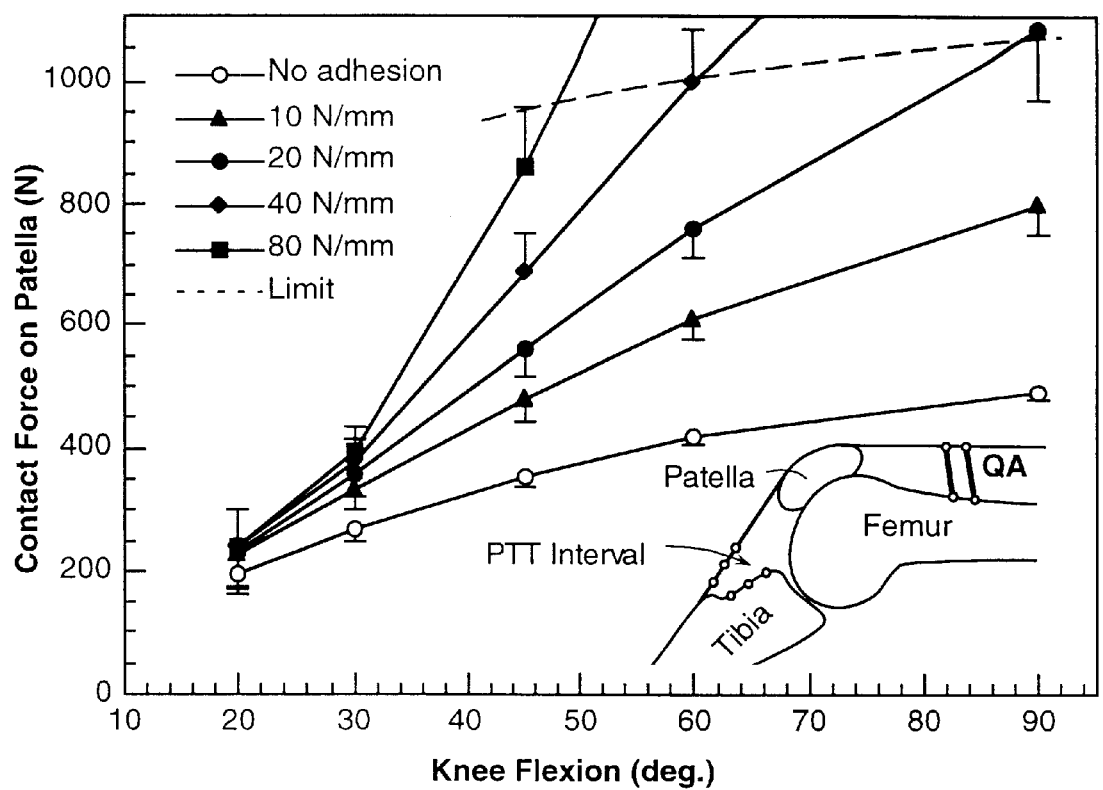

FIG. 19A illustrates variation of contact force on patella with different quadriceps tendon adhesion (QA) stiffness (dotted line represents upper limit of 600N tension on the quadriceps tendon adhesion(QA)).

Figure 19B:
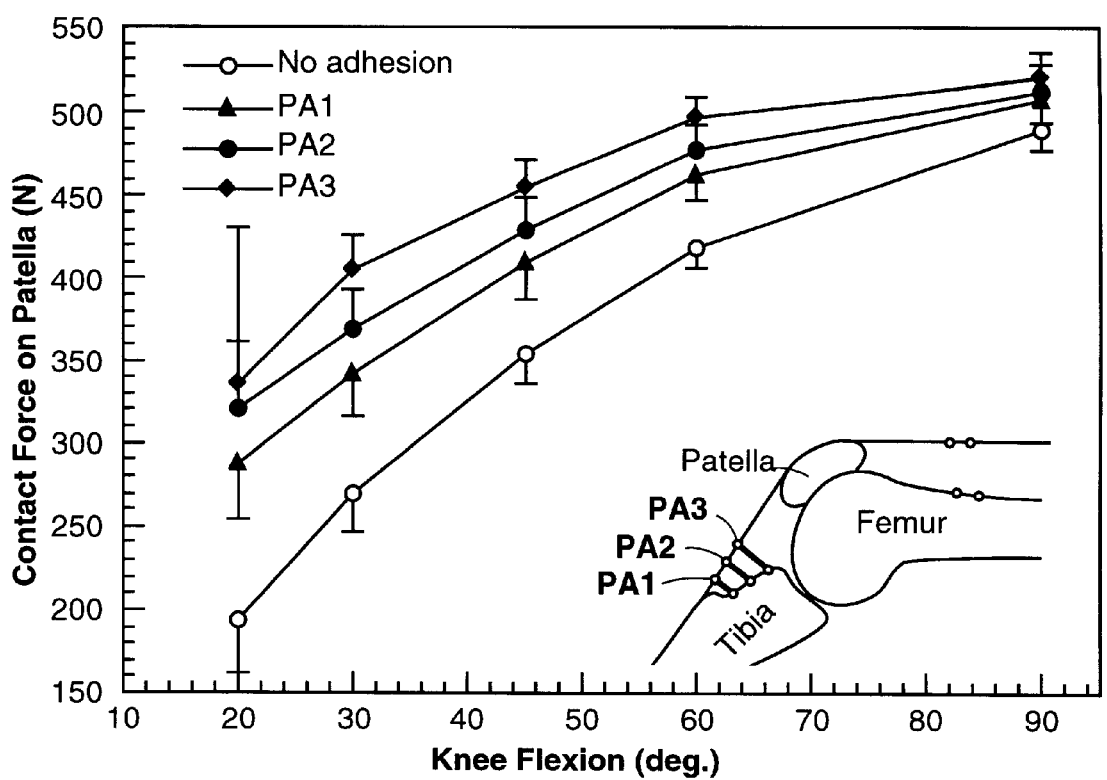

FIG. 19B illustrates variation of contact force on patella with different location of patellar tendon adhesion (PA1, PA2, PA3) (stiffness: 800 N/mm).

Figure 19C:
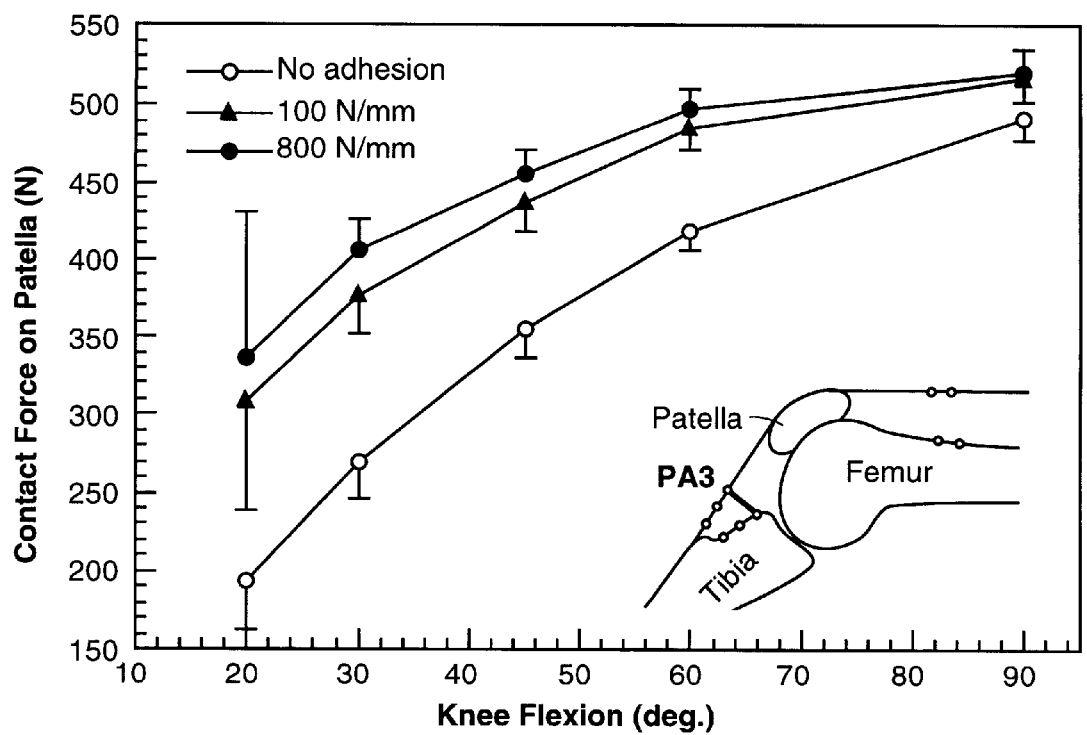

FIG. 19C illustrates variation of contact force on patella with different stiffnesses of patellar tendon adhesion for position of adhesion at PA3.

Figure 20:
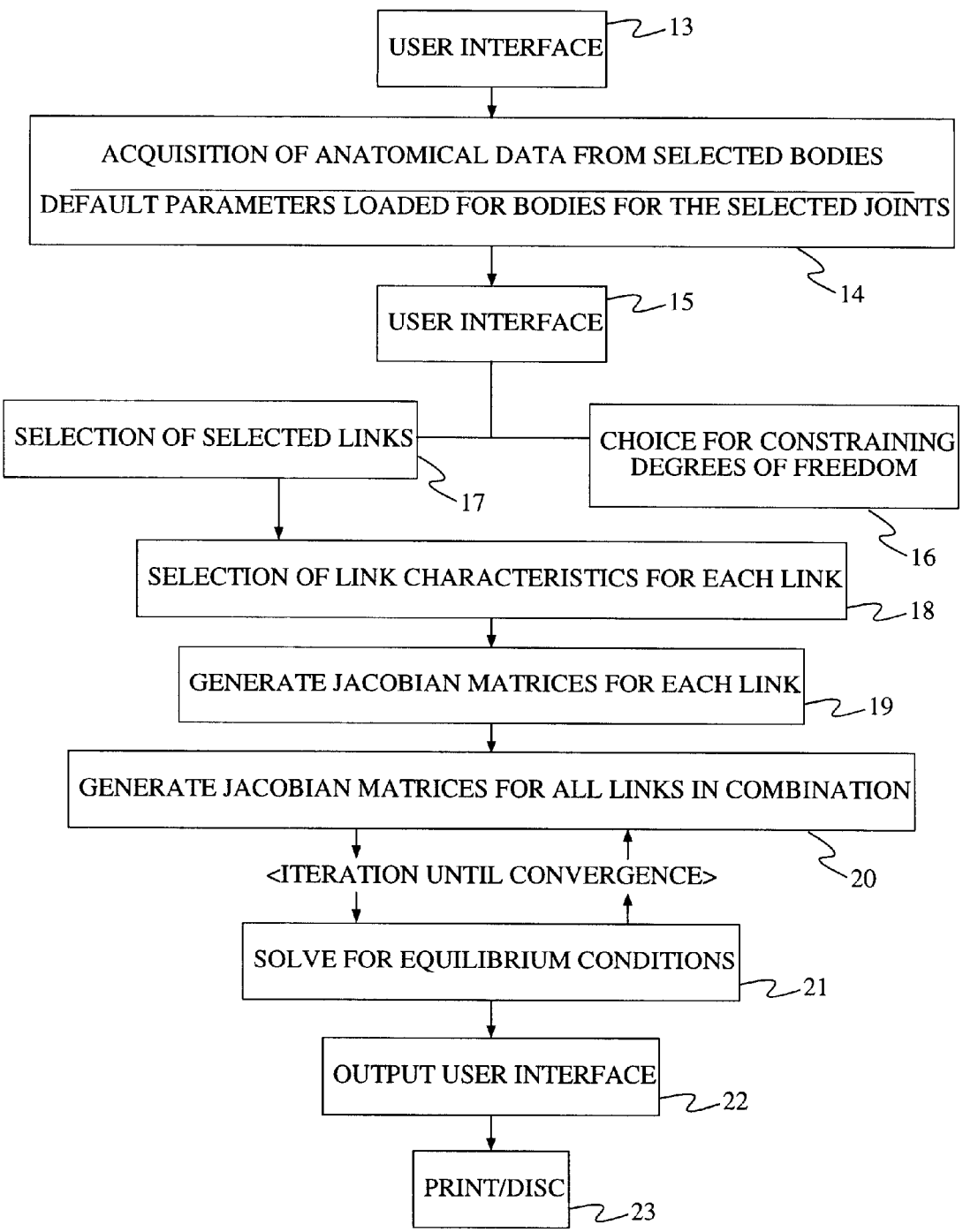

FIG. 20 illustrates a flow diagram of a three dimensional multibody modeling software program in accordance with the present invention.

Figure 21:
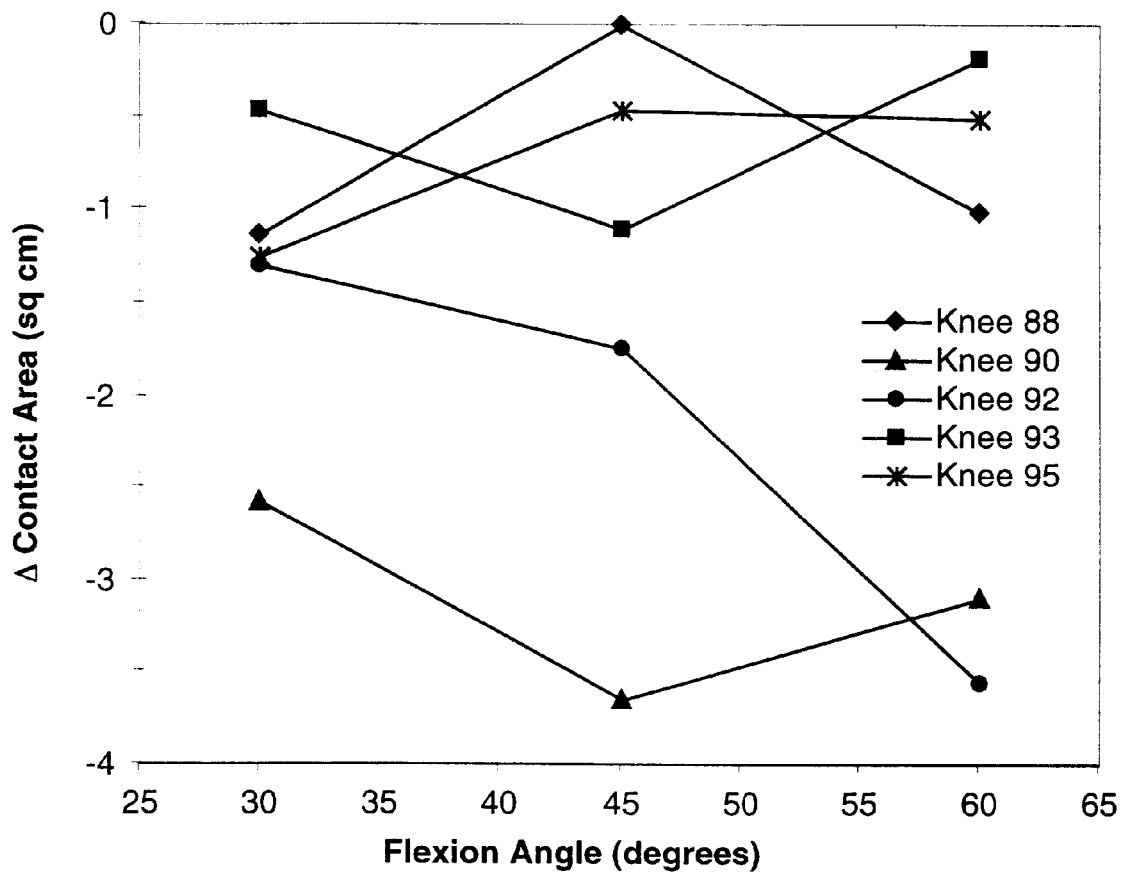

FIG. 21 illustrates changes in contact area due to 25 mm elevation of the tibial tuberosity.

Throughout the figures, the same reference numerals and characters, unless otherwise stated, are used to denote like features, elements, components or portions of the illustrated embodiments. Moreover, while the subject of the invention will now be described in detail with reference to the figures, it is done so in connection with the illustrative embodiments. It is intended that changes and modifications can be made to the described embodiments without departing form the true scope and spirit of the subject invention as defined by the appended claims.

5. DETAILED DESCRIPTION OF THE INVENTION

This three dimensional multibody modeling software program is a graphics based interactive model designed to allow a user to input anatomical data from any number of joints to be analyzed, to modify the input parameters of the bodies associated with the selected joint or joints and to rapidly view the changed results. Once a user has selected a target joint or joints, three dimensional anatomical data may be acquired from the joint or joints or from a library database collection and inputted into the software program. Thereafter, the user selects the links associated with the selected joint or joints. The user has the option to constrain one or more degree of freedom for any body. The links available for the knee, for example, correspond to an anatomical knee, and include ligament links, muscle links, tendon-pulley links, wrapping links, torsional spring links, articular contact links, particle contact links, external forces links, and external moments links. The user can further select link characteristics for each link, which allows for the flexibility of selecting from one or more of the parameters which are specific to the particular link type. The software program generates Jacobian matrices for each link from analytical derivations, thereafter, the software program generates Jacobian matrices for all of the selected links in combination. The software program then solves for the equilibrium condition. Iteration occurs until there is convergence to the equilibrium condition solution; the Jacobian matrices are updated at each iteration. The output display is rapidly available and demonstrates the results to the user in a graphical format, such as a three dimensional image of the selected joint or joints. The three dimensional representation of the anatomical joint may appear on a dimensional screen, but the visual image or images appear three dimensional to the user. Further, when rotated on such a two dimensional screen, the visual image or images of the three dimensional representation maintain a three dimensional appearance of the anatomical joint. As an interactive model, the user has the option to change the selection of the joint or joints by re-starting the process and inputting anatomical data for a newly selected the selected joint or joints. The user may optionally modify the selected joint or joints, the selected link types, the selected link characteristics, and the degree of freedom constraints. Thereafter, the changes can be visualized in the display output.

Any number of types of interactions, such as ligament forces, muscle forces, and contact forces, can be included in the formulation of the model. Any number of types of interaction can be specified simultaneously for any combination of bodies in the multibody model. Each material body in the multibody model can have up to six degrees of freedom associated with it, three in translation and three in rotation. When a body interacts with another body through a link, the resultant force and moment acting on one body due to the other body are equal and opposite.

In a non-limiting embodiment of the invention, ligament links are modeled as line segments whose forces are linearly or nonlinearly dependent on their length, stretch, or strain. Constant loads are applied through tendons to simulate constant muscle forces.

In another non-limiting embodiment of the invention, the tendons may loop through pulleys, attach to a bone, which permits the muscle force to be redirected in a physiologically realistic manner.

In another non-limiting embodiment of the invention, wrapping of the tendons and ligaments around bone and articular surfaces is modeled by imbedding particles in the substance of the ligaments and tendons. These frictionless, massless, point particles are moving bodies that can contact with the bone and articular surface that the tendon or ligaments wrap around. The interaction between these particles and the surfaces they contact redirects the line of action of the ligaments and tendons.

In another non-limiting embodiment of the invention, torsional springs, both linear and nonlinear, can be added to resist rotation between two rotating bodies.

In another non-limiting embodiment of the invention, external forces and moments can be applied to any body, either in the body-fixed coordinate or in a global coordinate system.

In another non-limiting embodiment of the invention, any translational or rotational degree of freedom of any moving body may be optionally constrained.

5.1 Nomenclature

The following conventions have been observed:

Font style:
  italic letter (e.g., a): scalar value
  bold lower case letter (e.g., a): vector
  bold upper case letter (e.g., A): second order tensor Paired Greek and Roman letters:
  bold Greek letter (e.g., $\boldsymbol{\pi}$): vector in the local coordinate system
  bold Roman letter (e.g., p): same vector in the global coordinate system Superscript:
  Greek letter (e.g., $a^\beta$): body identification number
  Roman letter (e.g., $k^{l_i}$): link identification number
  double letters (e.g., $p^{\beta l_i}$): first letter identifies the body second letter identifies the link General symbols

| | |
|---|---|
| a | translation vector |
| $\boldsymbol{\theta}$ | attitude vector |
| $\theta$ | magnitude of attitude vector $\boldsymbol{\theta}$ |
| x | vector representing either translation vector a or attitude vector $\boldsymbol{\theta}$ |
| $R(\boldsymbol{\theta})$ | rotation matrix with respect to attitude vector $\boldsymbol{\theta}$ |
| $Q(\boldsymbol{\theta})$ | related to the derivative of the rotation matrix $R(\boldsymbol{\theta})$ |
| I | identity tensor |
| 0 | null vector or tensor |
| $\mathbf{A}(\mathbf{x})$ | the skew-symmetric tensor of the dual vector (x) |
| $\alpha$ | link type |
| $\alpha_i$ | i-th link of link type $\alpha$ |
| $\boldsymbol{\pi}$ | position of a point in the local coordinate system |
| p | position of a point in the global coordinate system |
| $\boldsymbol{\phi}^{\beta\alpha_i}$ | force acting on body $\beta$ due to link $\alpha_i$ (local coordinate system) |
| $\mathbf{f}^{\beta\alpha_i}$ | force acting on body $\beta$ due to link $\alpha_i$ (global coordinate system) |
| $\boldsymbol{\mu}^{\beta\alpha_i}$ | moment acting on body $\beta$ due to link $\alpha_i$ (local coordinate system) |
| $\mathbf{m}^{\beta\alpha_i}$ | moment acting on body $\beta$ due to link $\alpha_i$ (global coordinate system) |
| $\mathbf{f}^\beta$ | sum of all forces acting on body $\beta$ |
| $\mathbf{m}^\beta$ | sum of all moments acting on body $\beta$ |
| f | generalized force vector |
| q | generalized degrees-of-freedom vector |
| J | Jacobian of the system of equations |
| $\mathbf{J}^{\beta\gamma}$ | sub-Jacobian of body $\beta$ with respect to body $\gamma$ |
| $\mathbf{d}^{\beta\alpha_i}$ | vector connecting two points of link $\alpha_i$ |
| $\hat{\mathbf{d}}^{\beta\alpha_i}$ | unit vector of $\mathbf{d}^{\beta\alpha_i}$ |
| $d^{\beta\alpha_i}$ | length of $\mathbf{d}^{\beta\alpha_i}$ |
| $F^{\alpha_i}$ | magnitude of force or moment produced by link $\alpha_i$ |
| $F'^{\alpha_i}$ | derivative of $F^{\alpha_i}$ |
| $\epsilon_{ijk}$ | permutation symbol (in indicial notation) |
| $\delta_{ij}$ | Kronecker delta symbol (in indicial notation) |
| $\hat{\mathbf{e}}_k^0$ | unit vector along the k-th axis of the global coordinate system |
| $n_\beta$ | total number of moving bodies |
| $n_\alpha$ | total number of links of type $\alpha$ |

Ligament link symbols

| | |
|---|---|
| $k^{l_i}$ | elastic constant of ligament link $l_i$ |
| $d_o^{l_i}$ | reference length of ligament link $l_i$ |
| $\epsilon^{l_i}$ | strain of ligament link $l_i$ |
| $\epsilon_o^{l_i}$ | reference strain of ligament link $l_i$ |
| $a^{l_i}, b^{l_i}$ | structural constants for ligament link $l_i$ |

Tendon-pulley link symbols

| | |
|---|---|
| $s_j^{p_i}$ | position of the j-th insertion of tendon-pulley link $p_i$ (global coordinate system) |
| $\zeta_j$ | body number of j-th insertion of tendon-pulley link $p_i$ |
| $d_j^{p_i}$ | vector connecting current pulley position to next pulley position of tendon-pulley link $p_i$ |

-continued

| | |
|---|---|
| $D_j^{p_i}$ | derivative of $\hat{d}_j^{p_i}$ with respect to $d_j^{p_i}$ |
| $n_{p_i}$ | total number of pulleys in tendon-pulley link $p_i$ |

Contact link symbols

| | |
|---|---|
| $p_j^{\beta\alpha_i}$ | position of j-th point on the primary surface of contact link $\alpha_i$ (global coordinate system) |
| $\hat{v}_j^{\beta\alpha_i}$ | unit normal at point $p_j^{\beta\alpha_i}$ of the primary surface (local coordinate system) |
| $\hat{n}_j^{\beta\alpha_i}$ | unit normal at point $p_j^{\beta\alpha_i}$ of the primary surface (global coordinate system) |
| u,v | parametric coordinates along a surface to locate any point on the surface |
| $p_j^{\gamma a_i}(u,v)$ | position of the point on the secondary surface associated with point $p_j^{\beta c_i}$ |
| $t_j^{\beta\alpha_i}$ | proximity vector at point $p_j^{\beta\alpha_i}$ of contact link $\alpha_i$ ($t_j^{\beta\alpha_i} = p_j^{\gamma a_i}(u,v) - p_j^{\beta\alpha_i}$) |
| $t_j^{\alpha_i}$ | proximity value of point $p_j^{\beta\alpha_i}$ |
| $A_j^{\beta\alpha_i}$ | area of the primary surface surrounding point $p_j^{\beta\alpha_i}$ |
| $n_p^{\beta\alpha_i}$ | total number of points on the primary surface of contact link $\alpha_i$ |

Particle contact link symbols

| | |
|---|---|
| $p^{\gamma c_i}(u,v)$ | position of the point on the contacting surface closest to point $p^{\beta c_i}$ |
| $\hat{n}^{\gamma a_i}$ | unit normal at point $p^{\gamma c_i}(u,v)$ (global coordinate system) |
| $t^{\beta c_i}$ | proximity vector of particle contact link $c_i$ ($t^{\beta c_i} = p^{\beta c_i} - p^{\gamma c_i}(u,v)$) |

5.2 General Definitions

Figure 1A:
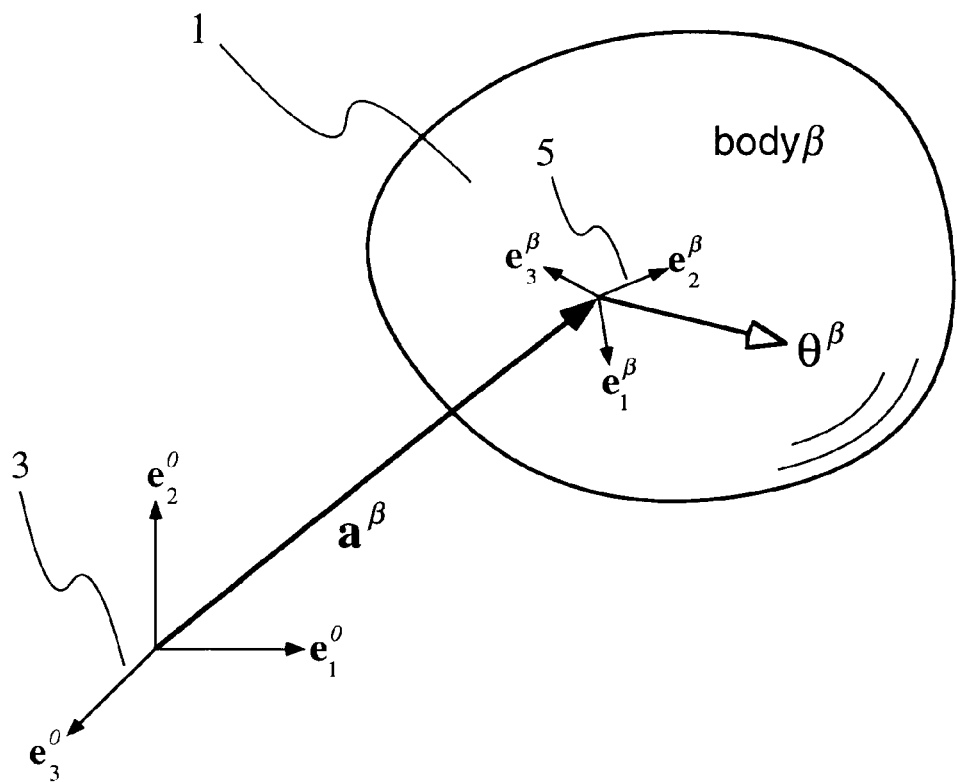
FIG. 1A shows a material body which has both translational DOF ($a^\beta$) and rotational DOF ($\theta^\beta$)
Figure 1B:
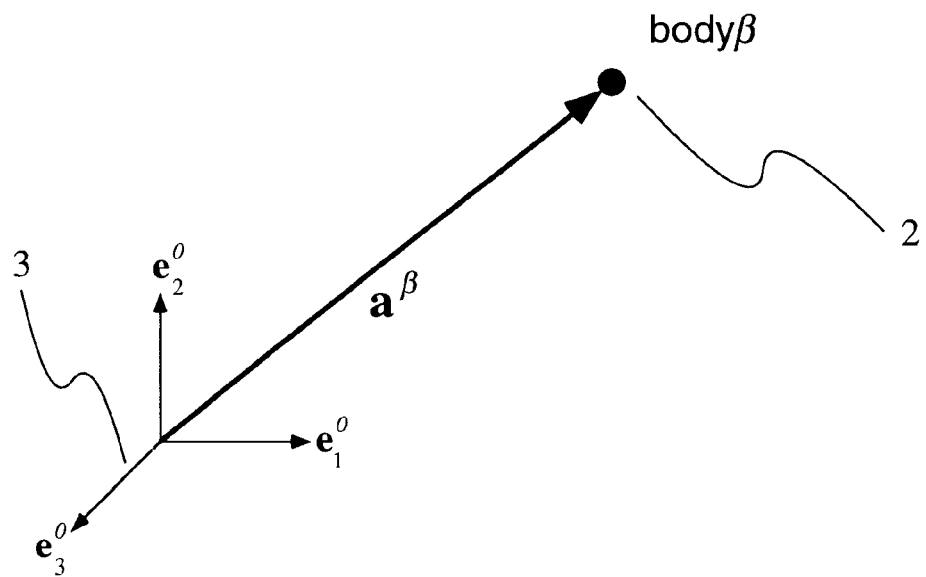
FIG. 1B shows a particle body which is a point body that only has translational DOF ($a^\beta$). Note that the arrow with an open arrow head (⇨) represents an attitude vector.

Two types of moving bodies exist in the model: a material body 1 and a particle body 2 (FIG. 1). A material body 1 has the full set of six degrees-of-freedom (DOF) ($a^\beta$, $\theta^\beta$) associated with it, where $a^\beta$ is the translation vector representing the three translation components of body $\beta$, and $\theta^\beta$ is the attitude vector representing the three rotation components of body $\beta$. An example of a material body 1 a bone. A particle body 2 is a point body in three-dimensional space that has only translational DOF ($a^\beta$), without rotational DOF. Therefore, when $\theta^\beta$ is mentioned, it applies only to a material body 1 and not to a particle body 2. Many moving bodies can exist in the model, i.e., $\beta=1$ to $n_\beta$, where $n_\beta$ is the total number of moving bodies. The model also includes the ground ($\beta=0$) which does not move. All translation and attitude vectors of moving bodies are determined relative to the ground; hence, the coordinate system of the ground is the global coordinate system 3. Since the ground does not move, translation and attitude vectors do not exist for the ground, and $a^\beta$ and $\theta^\beta$ are valid only for moving bodies.

The position of a point 4 on body $\beta$ can be expressed in two different coordinate systems. Position vector $\pi_j^\beta$ represents a point 4 in the local coordinate system 5 fixed to the moving body, while $p_j^\beta$ represents the same point 4 and in the global coordinate system 3 fixed to the ground, where j is the point number of that body. (FIG. 2). The position vectors $p_j^\beta$ and $\pi_j^\beta$ are related by:

$$p_j^\beta = R(\theta^\beta)\pi_j^\beta + a^\beta, \tag{1}$$

where $R(\theta^\beta)$ is the rotation tensor for the attitude vector $\theta^\beta$. Following the notation by Woltring, J. Biomech. 27:1399–1414 (1994), the rotation tensor $R(\boldsymbol{\theta})$ is given by:

$$R(\theta) = (\cos\theta)I + \frac{\sin\theta}{\theta}\mathcal{A}(\theta) + \frac{1-\cos\theta}{\theta^2}\theta\theta. \tag{2}$$

where $\theta$ is the magnitude of the attitude vector $\boldsymbol{\theta}$, defined by:

$$\theta = (\theta \cdot \theta)^{1/2}; \tag{3}$$

I is the identity tensor; $\mathbf{A}_i$ is the skew-symmetric tensor of a vector, defined by:

$$\mathbf{A}_{ij}(\theta_k) = \epsilon_{ijk}\theta_k \text{ (using indicial notation, where } \epsilon \text{ is the permutation symbol);} \quad (4)$$

and $\theta\theta$ is the dyadic product of $\theta$ with itself. For very small $\theta$, it is useful to recognize that $$R(\theta) \approx I + \mathcal{A}(\theta) + \frac{1}{2}\theta\theta, \theta \ll 1. \quad (5)$$

However, there are no limitations on the magnitude of $\theta$ in this analysis.

The bodies in the model interact with each other through various links connecting them. Link type $\alpha$ represents different link types in the model (e.g., link type $\alpha$=l represents a ligament link 6, and $\alpha$=a represents an articular contact link 7). Since many links of type $\alpha$ can exist in the model, each link is labeled $\alpha_i$ where i=1 to $n_\alpha$, ($n_\alpha$ is the total number of links of type $\alpha$). A force 8 acting on body $\beta$ through link $\alpha_i$ is represented by $\phi^{\beta\alpha_i}$ in the local body-fixed coordinate system 5, and the same force is represented by $f^{\beta\alpha_i}$ in the global ground-fixed coordinate system 3 (FIG. 2). The two force vectors are related to each other by:

$$f^{\beta\alpha_i} = R(\theta^\beta)\phi^{\beta\alpha_i}; \quad (6)$$

For a material body 1, a moment 8 acting on body $\beta$ about the origin of its local body-fixed coordinate system 5 due to link $\alpha_i$ is represented by $\mu^{\beta\alpha_i}$. If the moment 8 is due to force $\phi^{\beta\alpha_i}$, applied at point $\pi_j^{\alpha_i}$, $$\mu^{\beta\alpha_i} = \pi_j^{\beta\alpha_i} \times \phi^{\beta\alpha_i}. \quad (7)$$

Similarly, a moment 8 acting on body $\beta$ through link $\alpha_i$ about the origin of the global ground-fixed coordinate system 3 is represented by $m^{\beta\alpha_i}$. Again, if the moment 8 is due to force $f^{\beta\alpha_i}$ applied at point $p_j^{\alpha_i}$, $$m^{\beta\alpha_i} = p_j^{\beta\alpha_i} \times f^{\beta\alpha_i}. \quad (8)$$

Since a particle body 2 does not have rotational DOF, $\mu^{\beta\alpha_i}$ and $m^{\beta\alpha_i}$ are not relevant for a particle body 2. If link $\alpha_i$ connects two bodies $\beta$ and $\gamma$ (e.g., a ligament link 6 or a contact link 7), the force 8 and moment 8 acting on the other body, $\gamma$, are given by:

$$f^{\gamma\alpha_i} = -f^{\beta\alpha_i} \text{ and } m\gamma\alpha_i = -m^{\beta\alpha_i}, \quad (9)$$

by the principle of action and reaction.

5.2.2 Formulation of a Static Equilibrium Condition

The multibody model is a static model that finds the poses (i.e., translations and rotations) of moving bodies by satisfying the static equilibrium condition (FIG. 3). At static equilibrium, the sum of all forces, $f^\beta$ acting on body $\beta$ must equal the null vector:

$$f^\beta = \sum_\alpha \sum_{i=1}^{n_\alpha} f^{\beta\alpha_i} = 0. \quad (10a)$$

For a material body 1, the sum of all moments, $m^\beta$, acting on that body must also equal the null vector:

$$m^\beta = \sum_\alpha \sum_{i=1}^{n_\alpha} m^{\beta\alpha_i} = 0. \quad (10b)$$

To satisfy these equations for all moving bodies, a single generalized force vector, f, is used, where $$[f] = [f^1 m^1 f^2 m^2 \ldots f^{n_\beta} m^{n_\beta}]^T. \quad (11)$$

Similarly, the DOF's associated with each body may be represented by a generalized DOF vector, q, where $$[q] = [a^1\theta^1 a^2\theta^2 \ldots a^{n_\beta}\theta^{n_\beta} 0]^T. \quad (12)$$

For a particle body 2 $\beta$, $m^\beta$ and $\theta^\beta$ would be absent from vector f and vector q, respectively.

Thus, the model solves a system of nonlinear equations:

$$f(q) = 0, \quad (13)$$

where the unknowns are the DOF's in vector q. This system of equations is solved numerically using the Newton-Raphson iterative method, updating vector q by:

$$q \leftarrow q - dq, \quad (14a)$$

where dq is determined by solving:

$$Jdq = f. \quad (14b)$$

In the above equation, J is the Jacobian of the system of equations, given by:

$$J = \frac{\partial f}{\partial q}. \quad (15)$$

The Jacobian J has a large matrix made up of sub-matrices, where $$[J] = \begin{bmatrix} [J^{11}] & [J^{12}] & \cdots & [J^{1\gamma}] & \cdots & [J^{1n_\beta}] \\ [J^{21}] & [J^{22}] & \cdots & [J^{2\gamma}] & \cdots & [J^{2n_\beta}] \\ \vdots & \vdots & \ddots & \vdots & \ddots & \vdots \\ [J^{\beta 1}] & [J^{\beta 2}] & \cdots & [J^{\beta\gamma}] & \cdots & [J^{\beta n_\beta}] \\ \vdots & \vdots & \ddots & \vdots & \ddots & \vdots \\ [J^{n_\beta 1}] & [J^{n_\beta 2}] & \cdots & [J^{n_\beta\gamma}] & \cdots & [J^{n_\beta n_\beta}] \end{bmatrix}, \quad (16)$$

and each sub-component $J^{\beta\gamma}$ ($\beta$, $\gamma$=1 to $n_\beta$) is further composed of:

$$[J^{\beta\gamma}] = \begin{bmatrix} \left[\frac{\partial f^\beta}{\partial a^\gamma}\right] & \left[\frac{\partial f^\beta}{\partial \theta^\gamma}\right] \\ \left[\frac{\partial m^\beta}{\partial a^\gamma}\right] & \left[\frac{\partial m^\beta}{\partial \theta^\gamma}\right] \end{bmatrix}. \quad (17)$$

Each component of $J^{\beta\gamma}$ in equation (17) is a sum of derivatives due to each link. Hence, substituting equation (10) into equation (17), $$\frac{\partial f^\beta}{\partial a^\delta} = \sum_\alpha \sum_{i=1}^{n_\alpha} \frac{\partial f^{\beta\alpha_i}}{\partial a^\delta}, \quad (17a)$$

-continued $$\frac{\partial f^{\beta}}{\partial \theta^{\delta}} = \sum_{\alpha} \sum_{i=1}^{n_{\alpha}} \frac{\partial f^{\beta \alpha_i}}{\partial \theta^{\delta}}, \quad (18b)$$

$$\frac{\partial m^{\beta}}{\partial a^{\delta}} = \sum_{\alpha} \sum_{i=1}^{n_{\alpha}} \frac{\partial m^{\beta \alpha_i}}{\partial a^{\delta}}, \text{ and} \quad (18c)$$

$$\frac{\partial m^{\beta}}{\partial \theta^{\delta}} = \sum_{\alpha} \sum_{i=1}^{n_{\alpha}} \frac{\partial m^{\beta \alpha_i}}{\partial \theta^{\delta}}. \quad (18d)$$

In general, if link $\alpha_i$ connects body $\beta$ to body $\gamma$, from equation (9), $$\frac{\partial f^{\gamma \alpha_i}}{\partial a^{\delta}} = -\frac{\partial f^{\beta \alpha_i}}{\partial a^{\delta}}, \quad \frac{\partial f^{\gamma \alpha_i}}{\partial \theta^{\delta}} = -\frac{\partial f^{\beta \alpha_i}}{\partial \theta^{\delta}}, \quad (19)$$

$$\frac{\partial m^{\gamma \alpha_i}}{\partial a^{\delta}} = -\frac{\partial m^{\beta \alpha_i}}{\partial a^{\delta}}, \text{ and } \frac{\partial m^{\gamma \alpha_i}}{\partial \theta^{\delta}} = -\frac{\partial m^{\beta \alpha_i}}{\partial \theta^{\delta}}.$$

Furthermore, if link $\alpha_i$ connects bodies $\beta$ and $\gamma$, $f^{\beta \alpha_i}$ and $m^{\beta \alpha_i}$ are functions of bodies $\beta$ and $\gamma$ DOF's only, and thus, $$\frac{\partial f^{\beta \alpha_i}}{\partial a^{\delta}} = \frac{\partial f^{\beta \alpha_i}}{\partial \theta^{\delta}} = \frac{\partial m^{\beta \alpha_i}}{\partial a^{\delta}} = \frac{\partial m^{\beta \alpha_i}}{\partial \theta^{\delta}} = 0, \quad (20)$$

where $\delta \neq \beta$ and $\delta \neq \gamma$.

In order to achieve a stable and efficient convergence of the Newton-Raphson iterative process, the components of the Jacobian matrix are evaluated from analytical expressions for each link connecting various bodies.

5.2.3 Derivatives of Moment Vectors

From the previous section, equations (18c) and (18d) require calculation of derivatives of $m^{\beta \alpha_i}$, with respect to $\alpha^{\delta}$ and $\theta^{\delta}$, respectively. Moment vector $m^{\beta \alpha_i}$ is due to link $\alpha_i$, which in general represents a link connecting body $\beta$ to body $\gamma$. Then from equation (8), $$\frac{\partial m^{\beta \alpha_i}}{\partial a^{\delta}} = \frac{\partial}{\partial a^{\delta}}(p_j^{\beta \alpha_i} \times f^{\beta \alpha_i}) \quad (21)$$

$$= \mathcal{A}(p_j^{\beta \alpha_i})\frac{\partial f^{\beta \alpha_i}}{\partial a^{\delta}} - \mathcal{A}(f^{\beta \alpha_i})\frac{\partial p_j^{\beta \alpha_i}}{\partial a^{\delta}},$$

$$\frac{\partial m}{\partial a} = \mathcal{A}(p)\frac{\partial f}{\partial a} - \mathcal{A}(f)\frac{\partial p}{\partial a}. \quad (22)$$

since for any vectors $m = p \times f$ and $a$, Matrix $\mathbf{A}_f$ is the skew-symmetric tensor given in equation (4). Also, from equation (1), $$\frac{\partial p_j^{\beta \alpha_i}}{\partial a^{\delta}} = \begin{cases} I, & \delta = \beta \\ 0, & \delta \neq \beta \end{cases}. \quad (23)$$

If link $\alpha_i$ connects bodies $\beta$ and $\gamma$, substituting equations (19) and (23) into equation (21), $$\frac{\partial m^{\beta \alpha_i}}{\partial a^{\delta}} = \begin{cases} \mathcal{A}(p_i^{\beta \alpha_i})\frac{\partial f^{\beta \alpha_i}}{\partial a^{\beta}} - \mathcal{A}(f^{\beta \alpha_i}), & \delta = \beta \\ \mathcal{A}(p_i^{\beta \alpha_i})\frac{\partial f^{\beta \alpha_i}}{\partial a^{\gamma}}, & \delta = \gamma \\ 0, & \delta \neq \beta \text{ and } \delta \neq \gamma \end{cases} \quad (24)$$

Similarly, from equations (8) and (22), $$\frac{\partial m^{\beta \alpha_i}}{\partial \theta^{\delta}}$$

is given by:

$$\frac{\partial m^{\beta \alpha_i}}{\partial \theta^{\delta}} = \frac{\partial}{\partial \theta^{\delta}}(p_j^{\beta \alpha_i} \times f^{\beta \alpha_i}) \quad (25)$$

$$= \mathcal{A}(p_j^{\beta \alpha_i})\frac{\partial f^{\beta \alpha_i}}{\partial \theta^{\delta}} - \mathcal{A}(f^{\beta \alpha_i})\frac{\partial p_j^{\beta \alpha_i}}{\partial \theta^{\delta}}.$$

Also, from equation (1), $$\frac{\partial p_j^{\beta \alpha_i}}{\partial \theta^{\delta}} = \begin{cases} \frac{\partial R(\theta^{\beta})}{\partial \theta^{\beta}}\pi_j^{\beta \alpha_i}, & \text{when } \delta = \beta \\ 0, & \text{when } \delta \neq \beta \end{cases} \quad (26)$$

Following the notations of Woltring, J. Biomech. 27:1399–1414 (1994), $$\frac{\partial R(\theta)}{\partial \theta}\pi = -\mathcal{A}(R\pi)Q(\theta). \quad (27)$$

Matrix $Q(\theta)$ is related to the derivative of rotation matrix $R(\theta)$ such that $\mathbf{A}[Q(\theta)d\theta] = dRR^T$:

$$Q(\theta) = \frac{\theta \theta}{\theta^2} + \frac{\sin\left(\frac{\theta}{2}\right)}{\frac{\theta}{2}}R\left(\frac{\theta}{2}\right)\left(I - \frac{\theta \theta}{\theta^2}\right), \quad (28)$$

where $\theta$ is the magnitude of $\theta$ defined in equation (3). Again, it is useful to note that for very small $\theta$, $$Q(\theta) \approx I + \frac{1}{2}\mathbf{A}(\theta) + \frac{1}{6}\theta \theta, \quad \theta \ll 1. \quad (29)$$

Substituting equations (27) and (1) into equation (26):

$$\frac{\partial R(\theta^{\beta})}{\partial \theta^{\beta}}\pi_j^{\beta \alpha_i} = -\mathcal{A}(R(\theta^{\beta})\pi_j^{\beta \alpha_i})Q(\theta^{\beta}) \quad (30)$$

$$= -\mathcal{A}(p_j^{\beta \alpha_i} - a^{\beta})Q(\theta^{\beta}).$$

Finally, if link $\alpha_i$ connects bodies $\beta$ and $\gamma$, substituting equations (26) and (30) into equation (25), $$\frac{\partial m^{\beta\alpha_i}}{\partial \theta^\delta} = \begin{cases} \mathcal{A}(p_j^{\beta\alpha_i})\frac{\partial f^{\beta\alpha_i}}{\partial \theta^\beta} + & \text{when } \delta = \beta \\ \mathcal{A}(f^{\beta\alpha_i})\mathcal{A}(p_j^{\beta\alpha_i} - a^\beta)Q(\theta^\beta), & \\ \mathcal{A}(p_j^{\beta\alpha_i})\frac{\partial f^{\beta\alpha}}{\partial \theta^\gamma}, & \text{when } \delta = \gamma \\ 0, & \text{when } \delta \neq \beta \text{ and } \delta \neq \gamma \end{cases} \quad (31)$$

Equations (24) and (31) show how $$\frac{\partial m^{\beta\alpha_i}}{\partial a^\delta} \text{ and } \frac{\partial m^{\beta\alpha_i}}{\partial \theta^\delta}$$

can be determined once $$\frac{\partial f^{\beta\alpha_i}}{\partial a^\delta} \text{ and } \frac{\partial f^{\beta\alpha_i}}{\partial \theta^\beta}$$

are known. Therefore, it is sufficient to derive derivatives of force vectors for each link type, and derivatives of moment vectors can be calculated from equation (24) and (31) subsequently.

5.2.4 Ligament Link

A ligament is modeled by a ligament link 6 ($\alpha=1$) that connects two insertion points 4 as a line segment (FIG. 4). The ligament force acts along the direction of the line, and its magnitude is a function of the line segment length, as well as other parameters such as reference ligament length and ligament material properties. Since the multibody model is a static model, ligaments are simplified as either linear or nonlinear elastic line segments, and the time-dependent viscoelastic behavior is not simulated.

The ligament link 6 is represented by vector $d^{\beta l_i}$ connecting insertion point $p^{\beta l_i}$ on body $\beta$ to insertion point $p^{\gamma l_i}$ on body $\gamma$:

$$d^{\beta l_i} = p^{\gamma l_i} - p^{\beta l_i}. \quad (32)$$

Substituting equation (1) into equation (32), $$d^{\beta l_i} = R(\theta^\gamma)\pi^{\gamma l_i} + a^\gamma - R(\theta^\beta)\pi^{\beta l_i} - a^\beta. \quad (33)$$

The length of the ligament is:

$$d^{l_i} = (d^{\beta l_i} \cdot d^{\beta l_i})^{1/2}. \quad (34)$$

The force on body $\beta$ due to the ligament is given by:

$$f^{\beta l_i} = F^{l_i}(d^{l_i})\frac{d^{\beta l_i}}{d^{l_i}} = F^{l_i}(d^{l_i})\hat{d}^{\beta l_i}, \quad (35)$$

where $F^{l_i}(d^{l_i})$ is either a linear or nonlinear function relating the magnitude of the ligament force to the ligament length, and $\hat{d}^{\beta l_i}$ is the unit vector along $d^{\beta l_i}$.

To simplify the notation, let x represent any of $a^\beta$, $a^\gamma$, $\theta^\beta$, or $\theta^\gamma$. Then, differentiating equation (35) with respect to x, $$\frac{\partial f^{\beta l_i}}{\partial x} = \frac{\partial f^{\beta l_i}}{\partial d^{\beta l_i}}\frac{\partial d^{\beta l_i}}{\partial x}. \quad (36)$$

Also, differentiating equation (35) with respect to $d^{\beta l_i}$, $$\frac{\partial f^{\beta l_i}}{\partial d^{\beta l_i}} = \hat{d}^{\beta l_i}\left\{\frac{\partial F^{l_i}(d^{l_i})}{\partial d^{\beta l_i}}\right\} + F^{l_i}(d^{l_i})\frac{\partial \hat{d}^{\beta l_i}}{\partial d^{\beta l_i}}. \quad (37)$$

Expanding terms in equation (37) further, $$\frac{\partial}{\partial d^{\beta l_i}}[F^{l_i}(d^{l_i})] = \left\{\frac{\partial}{\partial d^{l_i}}[F^{l_i}(d^{l_i})]\right\}\frac{\partial d^{l_i}}{\partial d^{\beta l_i}}, \text{ and} \quad (38)$$

$$\frac{\partial \hat{d}^{\beta l_i}}{\partial d^{\beta l_i}} = \frac{\partial}{\partial d^{\beta l_i}}\left(\frac{d^{\beta l_i}}{d^{l_i}}\right) = \frac{1}{d^{l_i}}\frac{\partial d^{\beta l_i}}{\partial d^{\beta l_i}} - \frac{d^{\beta l_i}}{(d^{l_i})^2}\frac{\partial d^{l_i}}{\partial d^{\beta l_i}}. \quad (39)$$

Note that from equation (34), $$\frac{\partial d^{l_i}}{\partial d^{\beta l_i}} = \frac{\partial\left[(d^{\beta l_i} \cdot d^{\beta l_i})^{\frac{1}{2}}\right]}{\partial d^{\beta l_i}} = \frac{d^{\beta l_i}}{d^{l_i}} = \hat{d}^{\beta l_i}. \quad (40)$$

Hence, equations (38) and (39) become:

$$\frac{\partial}{\partial d^{\beta l_i}}[F^{l_i}(d^{l_i})] = F^{l_i\prime}\hat{d}^{\beta l_i} \text{ and} \quad (41)$$

$$\frac{\partial \hat{d}^{\beta l_i}}{\partial d^{\beta l_i}} = \frac{1}{d^{l_i}}I - \frac{1}{d^{l_i}}\hat{d}^{\beta l_i}\hat{d}^{\beta l_i} = \left(I - \hat{d}^{\beta l_i}\hat{d}^{\beta l_i}\right)\frac{1}{d^{l_i}}, \quad (42)$$

where $$F^{l_i\prime} = \frac{\partial F^{l_i}(d^{l_i})}{\partial d^{l_i}},$$

and $\hat{d}^{\beta l_i}\hat{d}^{\beta l_i}$ is the dyadic product of $\hat{d}^{\beta l_i}$ with itself. Substituting equations (41) and (42) into equation (37), $$\frac{\partial f^{\beta l_i}}{\partial d^{\beta l_i}} = F^{l_i\prime}\hat{d}^{\beta l_i}\hat{d}^{\beta l_i} + F^{l_i}\left(I - \hat{d}^{\beta l_i}\hat{d}^{\beta l_i}\right)\frac{1}{d^{l_i}} \quad (43)$$

$$= \left(F^{l_i\prime} - \frac{F^{l_i}}{d^{l_i}}\right)\hat{d}^{\beta l_i}\hat{d}^{\beta l_i} + \frac{F^{l_i}}{d^{l_i}}I,$$

Finally, substituting equation (43) into equation (36), $$\frac{\partial f^{\beta l_i}}{\partial x} = \left[\left(F^{l_i\prime} - \frac{F^{l_i}}{d^{l_i}}\right)\hat{d}^{\beta l_i}\hat{d}^{\beta l_i} + \frac{F^{l_i}}{d^{l_i}}I\right]\frac{\partial d^{\beta l_i}}{\partial x}. \quad (44)$$

Replacing x back with $a^\beta$, $a^\gamma$, $\theta^\beta$, and $\theta^\gamma$, when $x=a^\beta$, from equation (33), $$\frac{\partial d^{\beta l_i}}{\partial a^\beta} = -I. \quad (45a)$$

When $x=a^\gamma$, $$\frac{\partial d^{\beta l_i}}{\partial a^\gamma} = -\frac{\partial d^{\beta l_i}}{\partial a^\beta} = I. \quad (45b)$$

When $x=\theta^\beta$, using equations (27) and (1), $$\frac{\partial d^{\beta l_i}}{\partial \theta^\beta} = -\frac{\partial R(\theta^\beta)}{\partial \theta^\beta} \pi^{\beta l_i} \qquad (45c)$$

$$= \mathcal{A}(R(\theta^\beta)\pi^{\beta l_i})Q(\theta^\beta)$$

$$= \mathcal{A}(p^{\beta l_i} - a^\beta)Q(\theta^\beta).$$

Finally, when $x=\theta^\gamma$, $$\frac{\partial d^{\beta l_i}}{\partial \theta^\gamma} = -\mathcal{A}(p^{\gamma l_i} - a^\gamma)Q(\theta^\gamma) \qquad (45d)$$

Hence, $$\frac{\partial f^{\beta l_i}}{\partial a^\beta} = -\left(F^{l_i\prime} - \frac{F^{l_i}}{d^{l_i}}\right)\hat{d}^{\beta l_i}\hat{d}^{\beta l_i} - \frac{F^{l_i}}{d^{l_i}}I, \qquad (46a)$$

$$\frac{\partial f^{\beta l_i}}{\partial a^\gamma} = -\frac{\partial f^{\beta l_i}}{\partial a^\beta} = \left(F^{l_i\prime} - \frac{F^{l_i}}{d^{l_i}}\right)\hat{d}^{\beta l_i}\hat{d}^{\beta l_i} + \frac{F^{l_i}}{d^{l_i}}I, \qquad (46b)$$

$$\frac{\partial f^{\beta l_i}}{\partial \theta^\beta} = \left[\left(F^{l_i\prime} - \frac{F^{l_i}}{d^{l_i}}\right)\hat{d}^{\beta l_i}\hat{d}^{\beta l_i} + \frac{F^{l_i}}{d^{l_i}}I\right]\mathcal{A}(p^{\beta l_i} - a^\beta)Q(\theta^\beta), \qquad (46c)$$

and $$\frac{\partial f^{\beta l_i}}{\partial \theta^\gamma} = \left[-\left(F^{l_i\prime} - \frac{F^{l_i}}{d^{l_i}}\right)\hat{d}^{\beta l_i}\hat{d}^{\beta l_i} - \frac{F^{l_i}}{d^{l_i}}I\right]\mathcal{A}(p^{\gamma l_i} - a^\beta)Q(\theta^\gamma). \qquad (46d)$$

Therefore, sub-Jacobians for ligament link $l_i$ are analytically derived for $$\frac{\partial f^{\beta l_i}}{\partial a^\beta}, \frac{\partial f^{\beta l_i}}{\partial a^\gamma}, \frac{\partial f^{\beta l_i}}{\partial \theta^\gamma} \text{ and } \frac{\partial f^{\beta l_i}}{\partial \theta^\beta}.$$

Substituting equations (46) into equations (24) and (31) other components of the sub-Jacobians, $$\frac{\partial m^{\beta l_i}}{\partial a^\beta}, \frac{\partial m^\beta}{\partial a^\gamma}, \frac{\partial m^{\beta l_i}}{\partial \theta^\beta}, \text{ and } \frac{\partial m^{\beta l_i}}{\partial \theta^\gamma},$$

can be easily calculated.

In equation (35), the ligament can be represented by any function relating ligament force to the ligament length, with known derivative of the ligament force with respect to the ligament length. Several force-length relationships of a ligament are included in the model thus far. A ligament can be modeled using a linear force-length relationship, either as a tension-only element:

$$F^{l_i}=F^{l_i}=0, \ d^{l_i}<d_{41}{}^{l_i}; \text{ or} \qquad (47b)$$

as a tension-compression element:

$$F^{l_i}=k^{l_i}(d^{l_i}-d_{41}{}^{l_i}, \text{ for any } d^{1i}; \qquad (48)$$

$$F^{1i}=k^{1i}$$

where $k^{l_i}$ is the elastic constant and $d_0{}^{l_i}$ is the initial length of the ligament. A ligament can be also described using a non-linear tension-only relationship from several choices. Let $\epsilon^{l_i}$ be the strain of the ligament:

$$\varepsilon^{l_i} = \frac{d^{l_i} - d_o^{l_i}}{d_o^{l_i}}. \qquad (49)$$

The ligament force can be related to the strain by a quadratic relationship, where $$F^{l_i}=k^{l_i}(\epsilon^{l_i})^2$$

$$F^{l_i\prime} = \frac{2k^{l_i}\varepsilon^{l_i}}{d_o^{l_i}}, \ \varepsilon^{l_i} \geq 0; \text{ and} \qquad (50a)$$

$$F^{l_i}=F^{l_i}=0, \ \epsilon^{l_i}<0. \qquad (50b)$$

Also, only the toe region of the force-length relationship can be modeled as quadratic and modeled linear elsewhere:

$$F^{l_i}=k^{l_i}(\epsilon^{l_i}-\epsilon_0{}^{l_i})$$

$$F^{l_i\prime} = \frac{k^{l_i}}{d_o^{l_i}}, \ \varepsilon^{l_i} > 2\varepsilon_o^{l_i}; \qquad (51a)$$

$$F^{l_i\prime} = \frac{k^{l_i}(\varepsilon^{l_i})^2}{4\varepsilon_o^{l_i}} \ \varepsilon^{l_i}, 0 \leq \varepsilon^{l_i} \leq 2\varepsilon_o^{l_i}; \text{ and} \qquad (51b)$$

$$F^{l_i\prime} = \frac{k^{l_i}\varepsilon^{l_i}}{2\varepsilon_o^{l_i}d_o^{l_i}}.$$

$$F^{l_i}=F^{l_i}=0, \ \epsilon^{l_i}<0; \qquad (51c)$$

where $\epsilon_0{}^{l_i}$ is the reference strain demarcating transition from the quadratic toe region to the linear region. Finally, the ligament described by an exponential function:

$$F^{l_i}=F^{l_i}=0, \ d^{l_i}<d_0{}^{l_i}; \qquad (52b)$$

where e is the base of the natural logarithm, and $a^{l_i}$ and $b^{l_i}$ are material constants for the given relationship.

Any one of the above relationships can be chosen to model a ligament. Other relationships can be easily added to the model by providing a force-length equation and its derivative with respect to the ligament length. Similarly, in other links (e.g., contact link and torsional spring link), different linear and nonlinear force relationships can be used to represent that particular link.

5.2.5 Muscle Link

A muscle force is simulated in the model as a constant force applied on a line segment which inserts on two separate bodies. Hence, a muscle link 9 ($\alpha$=m) can be modeled as a special case of the ligament link 6. Like a ligament link 6, a muscle link 9 is a line segment, with its force acting along the direction of the line. However, since the magnitude of the force is constant, the derivative of force $F^{m_i}$ with respect to $d^{m_i}$ is 0 (i.e., $F^{m_i\prime}=0$). Thus, from equation (46):

$$\frac{\partial f^{\beta m_i}}{\partial a^\beta} = \frac{F^{m_i}}{d^{m_i}}\left(\hat{d}^{\beta m_i}\hat{d}^{\beta m_i} - I\right), \qquad (52a)$$

-continued $$\frac{\partial f^{\beta m_i}}{\partial a^\gamma} = -\frac{\partial f^{\beta m_i}}{\partial a^\beta} = \frac{F^{m_i}}{d^{m_i}}\left(-\hat{d}^{\beta m_i}\hat{d}^{\beta m_i} + I\right), \tag{52b}$$

$$\frac{\partial f^{\beta m_i}}{\partial \theta^\beta} = -\frac{F^{m_i}}{d^{m_i}}\left(\hat{d}^{\beta m_i}\hat{d}^{\beta m_i} - I\right)\mathcal{A}(p^{\beta m_i} - a^\beta)Q(\theta^\beta), \text{ and} \tag{52c}$$

$$\frac{\partial f^{\beta m_i}}{\partial \theta^\gamma} = \frac{F^{m_i}}{d^{m_i}}\left(\hat{d}^{\beta m_i}\hat{d}^{\beta m_i} - I\right)\mathcal{A}(p^{\beta m_i} - a^\gamma)Q(\theta^\gamma). \tag{52d}$$

5.2.6 Tendon-pulley Link

A tendon-pulley link 10 ($\alpha$=p) simulates a tendon passing across multiple diarthrodial joints (e.g., tendons in a finger) (FIG. 5). Except for the two ends of a tendon, a tendon-pulley link 10 does not attach to a body, but merely passes through frictionless pulleys 11 attached to the body. A pulley 11 is a point 4 on a body that redirects the tendon force; a body may contain more than one pulley. Like a muscle link 9, a tendon-pulley link 10 applies a constant tension throughout the tendon.

Let $s_j^{P_i}$ be the position of the j-th insertion of tendon $p_i$ in the global ground-fixed coordinate system 11 (FIG. 5), where j=1 to $n_{p_i}$ ($n_{p_i}$=total number of pulleys). Each insertion $s_j^{P_i}$ is attached to body $\beta = \zeta_j$. Since more than one pulley may attach to a body, body $\zeta_j$ of the j-th pulley and body $\zeta_j$ of the k-th pulley may actually be the same body. The position of a pulley 11 inserting on body $\zeta_j$ is also represented by $p^{\zeta_j P_i}(s_j^{P_i}=p^{\zeta_j P_i})$ in the global ground-fixed coordinate system 3, and $\pi^{\zeta_j P_i}$ in the local body-fixed coordinate system 5. To calculate the direction of each tendon segment, let $$d_j^{P_i} = d_j^{P_i} \hat{d}_j^{P_i} = s_{j+1}^{P_i} - s_j^{P_i}, \quad 1 \leq j \leq n_{p_i}-1, \tag{53}$$

where $d_j^{P_i}$ is the length of $d_j^{P_i}$, and $\hat{d}_j^{P_i}$ is the unit vector along $d_j^{P_i}$. Also, from equation (1), $$\begin{aligned} d_j^{P_i} &= p^{\zeta_{j+1} P_i} - p^{\zeta_j P_i} \\ &= R(\theta^{\zeta_{j+1} P_i})\pi^{\zeta_{j+1} P_i} + a^{\zeta_{j+1} P_i} - R(\theta^{\zeta_j P_i})\pi^{\zeta_j P_i} - a^{\zeta_j P_i} \end{aligned} \tag{54}$$

$$1 \leq j \leq n_{p_i} - 1.$$

Note that since $s_0^{P_i}$ and $s_{n_{p_i}+1}^{P_i}$ do not exist, vectors $d_0^{P_i}$ and $d_{n_{p_i}}^{P_i}$ do not exist. For convenience in notation let $s_0^{P_i}=s_1^{P_i}$ and $s_{n_{p_i}}^{P_i}=s_{n_{p_i}+1}^{P_i}$; hence, assign $d_0^{P_i}=d_{n_{p_i}}^{P_i}=0$ and $\hat{d}_0^{P_i}=\hat{d}_{n_{p_i}}^{P_i}=0$. Then, the force acting on body $\zeta_j$ through tendon $p_i$ is given by:

$$f^{\zeta_j P_i} = F^{P_i}(\hat{d}_j^{P_i} - \hat{d}_{j-1}^{P_i}), \quad 1 \leq j \leq n_{p_i}, \tag{55}$$

where $F^{P_i}$ is the constant muscle force applied on the tendon. Let x be a vector representing translation vector $a^\delta$ or an attitude vector $\theta^\delta$ of body $\delta$ connected to tendon $P_i$. Differentiating equation (55) with respect to vector x, $$\begin{aligned} \frac{\partial f^{\zeta_j P_i}}{\partial x} &= F^{P_i}\left(\frac{\partial \hat{d}_j^{P_i}}{\partial x} - \frac{\partial \hat{d}_{j-1}^{P_i}}{\partial x}\right) \\ &= F^{P_i}\left(\frac{\partial \hat{d}_j^{P_i}}{\partial d_j^{P_i}} \frac{\partial d_j^{P_i}}{\partial x} - \frac{\partial \hat{d}_{j-1}^{P_i}}{\partial d_{j-1}^{P_i}} \frac{\partial d_{j-1}^{P_i}}{\partial x}\right). \end{aligned} \tag{56}$$

Using equation (41), let $$D_j^{P_i} = \frac{\partial \hat{d}_j^{P_i}}{\partial d_j^{P_i}} = \begin{cases} \frac{1}{d_j^{P_i}}(I - \hat{d}_j^{P_i}\hat{d}_j^{P_i}), & 1 \leq j \leq n_{p_i} - 1 \\ 0, & j=0, j=n_{p_i} \end{cases}. \tag{57}$$

When $x=a^\delta$, from equation (54), $$\frac{\partial d_j^{P_i}}{\partial a^\delta}$$

becomes, $$\frac{\partial d_j^{P_i}}{\partial a^\delta} = \frac{\partial a^{\zeta_{j+1} P_i}}{\partial a^\delta} - \frac{\partial a^{\zeta_j P_i}}{\partial a^\delta}. \tag{58}$$

Substituting equations (57) and (58) into equation (56), $$\frac{\partial f^{\zeta_j P_i}}{\partial a^\delta} = \begin{cases} 0, & \delta > j+1 \\ F^{P_i} D_j^{P_i}, & \delta = j+1 \\ F^{P_i}(-D_j^{P_i} - D_{j-1}^{P_i}), & \delta = j \\ F^{P_i} D_{j-1}^{P_i}, & \delta = j-1 \\ 0, & \delta < j-1 \end{cases}. \tag{59}$$

Similarly, when $x=\theta^\delta$, differentiating equation (54) with respect to $\theta^\delta$, $$\frac{\partial d_j^{P_i}}{\partial \theta^\delta} = \frac{\partial [R(\theta^{\zeta_{j+1} P_i})\pi^{\zeta_{j+1} P_i}]}{\partial \theta^\delta} - \frac{\partial [R(\theta^{\zeta_j P_i})\pi^{\zeta_j P_i}]}{\partial \theta^\delta}. \tag{60}$$

Finally, substituting equations (27), (57), and (60) into (56), $$\frac{\partial f^{\zeta_j P_i}}{\partial \theta^\delta} = \begin{cases} 0, & \delta > j+1 \\ -F^{P_i} D_j^{P_i} \mathcal{A}(p^{\zeta_{j+1} P_i} - a^{\zeta_{j+1}})Q(\theta^{\zeta_{j+1}}), & \delta = j+1 \\ F^{P_i}(D_j^{P_i} + D_{j-1}^{P_i})\mathcal{A}(p^{\zeta_j P_i} - a^{\zeta_j})Q(\theta^{\zeta_j}), & \delta = j \\ -F^{P_i} D_{j-1}^{P_i} \mathcal{A}(p^{\zeta_{j-1} P_i} - a^{\zeta_{j-1}})Q(\theta^{\zeta_{j-1}}), & \delta = j-1 \\ 0, & \delta < j-1 \end{cases}. \tag{61}$$

Although most links in the model connect two bodies, the tendon-pulley link 10 is an example of a link that connects multiple bodies. The calculation of sub-Jacobian for the tendon-pulley link 10 is similar to the ligament and tendon links derived previously. As equations (59) and (61) show, for a tendon-pulley link 10, the force 8 acting on a body is affected by the previous insertion, current insertion, and next insertion.

5.2.7 Articular Contact Link

Contact between two articular surfaces is simulated by a surface contact link 7 ($\alpha$=a). In the model, complex and irregular diarthrodial joint surfaces are represented by parametric equations. The number of points 4 on a surface can reach several thousands to faithfully represent each surface. Although, the cartilage surfaces deform on contact in real joints, to simplify the contact calculation, the model represents the surfaces as rigid surfaces that do not change their shape. To approximate the contact between two articular surfaces, rigid anatomical surfaces are allowed to penetrate each other, and the amount of penetration or overlap is assumed to be related to the amount of deformation. At each point on the surface, the magnitude of the surface traction due to the surface contact is calculated as a function of the amount of overlap, and the contact area is approximated by the region of surface overlap.

In diarthrodial joints, a cartilage layer is much softer than the underlying bone, and most deformation occurs in the cartilage layer upon contact. Thus, a thin deforming layer with rigid backing is a reasonable assumption for articular cartilage. Moreover, cartilage is a biphasic material that deforms as a function of time, and contact stress and area change as a function of time. The model predicts a first order approximation of the surface traction at a certain time after joint loading. Also, the friction between cartilage surfaces is assumed to be negligible. The contact force at each surface point is directed along the surface normal calculated from the rigid undeformed surfaces. These assumptions simplify contact calculation between two complex surfaces. A good approximation of surface traction of the cartilage can be made. Other mechanical variables such as total contact force and contact area can be predicted accurately by the multibody model.

In the contact calculation of the multibody model, one surface is designated as a primary surface (attached to body β), and the opposing surface is designated as a secondary surface (attached to body γ) (FIG. 6). During each iteration, the surface traction and contact force is calculated only on the primary surface, and the contact force on the secondary surfaces is calculated using equation (9). The contact is determined by calculating the proximity from each primary surface point to the secondary surface, along the direction normal to the primary surface. Let $p_j^{\beta a_i}$ be a point on the primary surface of body β. Since there are many points on the surface, j=1 to $n_p^{\beta a_i}$, where $n_p^{\beta a_i}$ is the total number of points on the primary surface. At point $p_j^{\beta a_i}$, let $\hat{n}_j^{\beta a_i}$ represent the unit outward surface normal in the global ground-fixed coordinate system 3. The same normal is represented by $\hat{n}_j^{\beta a_i}$ in the local body-fixed coordinate system 5. As in equation (5), two unit normals are related by:

$$\hat{n}_j^{\beta a_i} = R(\theta^\beta) \hat{v}_j^{\beta a_i}. \qquad (63)$$

Proximity $t_j^{a_i}$ is calculated by finding a point $p_j^{\gamma a_i}(u, v)$ on the secondary surface that intersects a ray from point $p_j^{\beta a_i}$ along the unit normal $\hat{n}_j^{\beta a_i}$:

$$t_j^{\beta a_i} = t_j^{a_i} \hat{n}_j^{\beta a_i} = p_j^{\gamma a_i}(u, v, a^\gamma, \theta^\gamma) - p_j^{\beta a_i}(a^\beta, \theta^\beta) \qquad (64)$$

The position of $p_j^{\gamma a_i}(u, v, a^\gamma, \theta^\gamma)$ is unknown a priori, and it must be determined by solving equation (64). The location of the contact point on the secondary surface is not fixed but changes as body β or γ moves. Hence, the contact point on the secondary surface is located using parametric coordinates u and v along the secondary surface. Although point $p_j^{\gamma a_i}(u, v, a^\gamma, \theta^\gamma)$ lies on the secondary surface, the index j refers to the point number on the primary surface. In equation (64), proximity $t_j^{a_i}$ ($t^{a_i} = t^{\beta a_i} \cdot \hat{n}_j^{\beta a_i}$) is negative if point $p_j^{\beta a_i}$ on the primary surface penetrates the secondary surface, and positive otherwise. The contact force on point $p_j^{\beta a_i}$ is given by:

$$f_j^{\beta a_i} = F_j^{a_i}(t_j^{a_i}) \hat{n}_j^{\beta a_i}, \qquad (65)$$

where $F_j^{a_i}(t_j^{a_i})$ is a function relating the magnitude of the force to the proximity value. The contact force is directed along the primary surface normal, $\hat{n}_j^{\beta a_i}$. Combining contact forces from all points on the primary surface, the total contact force on body β due to contact link $a_i$ is:

$$f^{\beta a} = \sum_{j=1}^{n_p^\beta} f_j^{\beta a}, \qquad (66)$$

Differentiating equation (65) with respect to vector x representing $a^\beta$, $a^\gamma$, $\theta^\beta$, or $\theta^\gamma$, $$\frac{\partial f_j^{\beta a_i}}{\partial x} = \frac{\partial f_j^{\beta a_i}}{\partial t_j^{a_i}} \frac{\partial t_j^{a_i}}{\partial x} = F_j^{a_i\prime} \hat{n}_j^{\beta a_i} \frac{\partial t_j^{a_i}}{\partial x} + F_j^{a_i} \frac{\partial \hat{n}_j^{\beta a_i}}{\partial x}, \qquad (67)$$

where $$F_j^{a_i\prime} = \frac{\partial F_j^{a_i}(t_j^{a_i})}{\partial t_j^{a_i}}.$$

Also, differentiating equation (64) with respect to x, $$\frac{\partial t_j^{\beta a_i}}{\partial x} = \hat{n}_j^{\beta a_i} \frac{\partial t_j^{a_i}}{\partial x} + t_j^{a_i} \frac{\partial \hat{n}_j^{\beta a_i}}{\partial x} = \frac{\partial p_j^{\gamma a_i}}{\partial x} - \frac{\partial p_j^{\beta a_i}}{\partial x}. \qquad (68)$$

Expanding $$\frac{\partial p_j^{\gamma a_i}}{\partial x}$$

in equation (68), $$\hat{n}_j^{\beta a_i} \frac{\partial t_j^{a_i}}{\partial x} + t_j^{a_i} \frac{\partial \hat{n}_j^{\beta a_i}}{\partial x} = \frac{\partial p_j^{\gamma a_i}}{\partial u} \frac{\partial u}{\partial x} + \frac{\partial p_j^{\gamma a_i}}{\partial v} \frac{\partial v}{\partial x} + \qquad (69)$$
$$\left( \left( \frac{\partial p_j^{\gamma a_i}}{\partial a^\gamma} \right)\bigg|_{u,v} \right) \frac{\partial a^\gamma}{\partial x} +$$
$$\left( \left( \frac{\partial p_j^{\gamma a_i}}{\partial \theta^\gamma} \right)\bigg|_{u,v} \right) \frac{\partial \theta^\gamma}{\partial x} - \frac{\partial p_j^{\beta a_i}}{\partial x},$$

where $$\frac{\partial p_j^{\gamma a_i}}{\partial u} \text{ and } \frac{\partial p_j^{\gamma a_i}}{\partial v}$$

are tangent vectors at point $p_j^{\gamma a_i}(u, v, a^\gamma, \theta^\gamma)$ on the secondary surface along the u and v directions, respectively. Substituting equations (1) and (27) above, and operating on both sides of the equation by $\hat{e}_k^o$ which represents a unit vector along the k-th axis of the global coordinate system, $$\left( \hat{n}_j^{\beta a_i} \frac{\partial t_j^{a_i}}{\partial x} \right) \hat{e}_k^o - \left( \frac{\partial p_j^{\gamma a_i}}{\partial u} \frac{\partial u}{\partial x} \right) \hat{e}_k^o - \left( \frac{\partial p_j^{\gamma a_i}}{\partial v} \frac{\partial v}{\partial x} \right) \hat{e}_k^o = \qquad (70)$$
$$\left[ I \frac{\partial a^\gamma}{\partial x} - A(p_j^{\gamma a_i} - a^\gamma) \frac{\partial \theta^\gamma}{\partial x} - \frac{\partial p_j^{\beta a_i}}{\partial x} - t_j^{a_i} \frac{\partial \hat{n}_j^{\beta a_i}}{\partial x} \right] \hat{e}_k^o.$$

Recall that for any vectors a, b, and c:

$$(ab)c = (b \cdot c)a \qquad (71)$$

Hence, using the relationship in equation (71), $$\left(\frac{\partial t_j^{a_i}}{\partial x}\cdot\hat{e}_k^o\right)\hat{n}_j^{\beta a_i} - \left(\frac{\partial u}{\partial x}\cdot\hat{e}_k^o\right)\frac{\partial p_j^{\gamma a_i}}{\partial u} - \left(\frac{\partial v}{\partial x}\cdot\hat{e}_k^o\right)\frac{\partial p_j^{\gamma a_i}}{\partial v} = \left(I\frac{\partial a^\gamma}{\partial x} - \mathcal{A}(p_j^{\gamma a_i}-a^\gamma)Q(\theta^\gamma)\frac{\partial\theta^\gamma}{\partial x} - \frac{\partial p_j^{\beta a_i}}{\partial x} - t_j^{a_i}\frac{\partial\hat{n}_j^{\beta a_i}}{\partial x}\right)\hat{e}_k^o. \quad (72)$$

Equation (72) is a vector equation (i.e., three scalar equations). The unit normal, $\hat{n}_j^{\beta a_i}$, of the primary surface and the tangent vectors, $$\frac{\partial p_j^{\gamma a_i}}{\partial u} \text{ and } \frac{\partial p_j^{\gamma a_i}}{\partial v},$$

of the secondary surface can be calculated from the analytical representation of the surfaces. Three vector equations (k=1 to 3) can be each solved to determine the k-th component of $$\frac{\partial t_j^a}{\partial x}\left(\text{i.e., }\frac{\partial t_j^{a_i}}{\partial x}\cdot\hat{e}_k^o\right).$$

Note that to solve for $$\frac{\partial t_j^{a_i}}{\partial x}, \text{ both } \frac{\partial u}{\partial x} \text{ and } \frac{\partial v}{\partial x}$$

must also be obtained simultaneously.

Substituting $a^\beta$, $a^\gamma$, $\theta^\beta$ and $\theta^\gamma$ with x, when x=$a^\beta$, $$\frac{\partial a^\gamma}{\partial a^\beta} = \frac{\partial a^\theta}{\partial a^\beta} = \frac{\partial n^{\beta a_i}}{\partial a^\beta} = 0 \text{ and } \frac{\partial p^{\beta a_i}}{\partial a^\beta} = I \quad (73)$$

Hence, RHS of equation (72) becomes $(-\hat{e}_k^o)$, and $$\frac{\partial t_j^{a_i}}{\partial a^\beta}$$

can be solved from equation (72). Substituting $$\frac{\partial t_j^{a_i}}{\partial a^\beta}$$

into equation (67), $$\frac{\partial f_j^{\beta a_i}}{\partial a^\beta} = F_j^{a_i\prime}\hat{n}_j^{\beta a_i}\frac{\partial t_j^{a_i}}{\partial a^\beta}. \quad (74)$$

When x=$a^\gamma$, $$\frac{\partial\theta^\gamma}{\partial a^\gamma} = \frac{\partial p_j^{\beta a_i}}{\partial a^\gamma} = \frac{\partial\hat{n}_j^{\beta a_i}}{\partial a^\gamma} = 0 \text{ and } \frac{\partial a^\gamma}{\partial a^\gamma} = I. \quad (75)$$

Hence, the RHS of equation (72) become $\hat{e}_k^o$. Since this RHS is the negative of that obtained when x=$a^\beta$, it follows that $$\frac{\partial t_j^{a_i}}{\partial a^\gamma} = -\frac{\partial t_j^{a_i}}{\partial a^\beta}.$$

Thus, $$\frac{\partial f_j^{\beta a_i}}{\partial a^\gamma} = \frac{\partial f_j^{\beta a_i}}{\partial t_j^{a_i}}\frac{\partial t_j^{a_i}}{\partial a^\gamma} = \frac{\partial f_j^{\beta a_i}}{\partial t_j^{a_i}}\left(-\frac{\partial t_j^{a_i}}{\partial a^\beta}\right) = -\frac{\partial f_j^{\beta a_i}}{\partial a^\beta}. \quad (76)$$

When x=$\theta^\beta$, using equation (27), $$\frac{\partial a^\gamma}{\partial\theta^\beta} = \frac{\partial\theta^\gamma}{\partial\theta^\beta} = 0, \quad (77)$$

$$\frac{\partial p_j^{\beta a_i}}{\partial\theta^\beta} = -\mathcal{A}(p_j^{\beta a_i}-a^\beta)Q(\theta^\beta), \text{ and}$$

$$\frac{\partial\hat{n}_j^{\beta a_i}}{\partial\theta^\beta} = -\mathcal{A}(\hat{n}_j^{\beta a_i})Q(\theta^\beta);$$

and the right-hand-side (RHS) of equation (72) becomes:

$$[\mathbf{A}(p_j^{\beta a_i}-a^\beta)Q(\theta^\beta)++t_j^{a_i}\mathbf{A}(\hat{n}_j^{\beta a_i})Q(\theta^\beta)]\hat{e}_k^o. \quad (78)$$

Substituting the solution of $$\frac{\partial t_j^{a_i}}{\partial\theta^\beta}$$

from equations (72) and (78) into equation (67), $$\frac{\partial f_j^{\beta a_i}}{\partial\theta^\beta} = F_j^{a_i\prime}\hat{n}_j^{\beta a_i}\frac{\partial t_j^{a_i}}{\partial\theta^\beta} - F_j^{a_i}\mathcal{A}(\hat{n}_j^{\beta a_i})Q(\theta^\beta). \quad (79)$$

Finally, when x=$\theta^\gamma$, $$\frac{\partial a^\gamma}{\partial\theta^\gamma} = \frac{\partial p_j^{\beta a_i}}{\partial\theta^\gamma} = \frac{\partial\hat{n}_j^{\beta a_i}}{\partial\theta^\gamma} = 0 \text{ and } \frac{\partial\theta^\gamma}{\partial\theta^\gamma} = I; \quad (80)$$

and the RHS of equation (72) becomes:

$$-\mathbf{A}(p_j^{\gamma a_i}-a^\gamma)Q(\theta^\gamma)\hat{e}_k^o. \quad (81)$$

Again, after calculating $$\frac{\partial t_j^{a_i}}{\partial\theta^\gamma}$$

from equations (72) and (81) and substituting it into equation (67), $$\frac{\partial f_j^{\beta a_i}}{\partial\theta^\gamma} = F_j^{a_i\prime}\hat{n}_j^{\beta a_i}\frac{\partial t_j^{a_i}}{\partial\theta^\gamma}. \quad (82)$$

Equations (74), (76), (79), and (82) provide derivatives of contact force at each point on the primary surface. To calculate the derivative of the total contact force, equation (66) is used to sum all contact force derivatives of each surface point. As in the ligament link derivation, any function relating surface traction to proximity can be used in equation (65) to calculate the contact force and its derivatives. Therefore, the model accommodates complex three-dimensional surfaces with different force-proximity relationships.

5.2.8 Particle Contact Link

Wrapping of ligaments and tendons around articular and bony surfaces is a common occurrence in diarthrodial joints. In the multibody model, to efficiently simulate the wrapping, particles are imbedded into ligaments and tendons, and these particles are allowed to contact the surface and sliding along it with zero friction. The imbedded particles redirect the ligament or muscle forces while transmitting the resultant contact force onto the surface (FIG. 7). These particles are moving bodies with only translational DOF. The particle to surface contact link 12 ($\alpha$=c) calculates contact between a particle and a surface. As in the articular surface contact calculation, the contact force is determined as a function of the proximity between the particle and the surface.

Let $\pi^{\beta c_i}$ be the location of particle $\beta 2$ in the local particle-body coordinate system 5. Although $\pi^{\beta c_i}$ is typically located at the origin of particle body $\beta 2$ (i.e., $\pi^{\beta c_i}=0$), it is assumed nevertheless that $\pi^{\beta c_i}$ could be positioned anywhere in the local coordinate system 5. From equation (1), the same point is represented in the global coordinate system 3 as:

$$p^{\beta c_i} = \pi^{\beta c_i} + a^{\beta}, \tag{83}$$

since particle body $\beta 2$ does not rotate. Let $p^{\gamma c_i}$ be the nearest point on the contacting surface (attached to body $\gamma$) to point $p^{\beta c_i}$. By the definition of the nearest distance between a point and a surface, vector $t^{\beta c_i}$, connecting $p^{\beta c_i}$, and $p^{\gamma c_i}$ is normal to the contacting surface:

$$t^{\beta c_i} = p^{\beta c_i}(a^{\beta}) - p^{\gamma c_i}(u, v, a^{\gamma}, \theta^{\gamma}) = t^{c_i} \hat{n}^{\gamma c_i}, \tag{84}$$

where $t^{c_i}$ is the proximity between the particle and the surface ($t^{c_i} = t^{\beta c_i} \cdot \hat{n}^{\gamma c_i}$), and $\hat{n}^{\gamma c_i}$ is the unit normal of the surface at $p^{\gamma c_i}(u, v, a^{\gamma}, \theta^{\gamma})$. As in the articular contact calculation, $t^{c_i}$ is negative if $p^{\beta c_i}$ lies inside the contacting surface. Since normal vector $\hat{n}^{\beta c_i}$ does not exist for a particle body, the definition of $t^{\beta c_i}$ ($t^{\beta c_i} = p^{\beta c_i} - p^{\gamma c_i}$) is slightly different from the articular contact calculation ($t^{\beta \alpha_i} = p^{\gamma \alpha_i} - p^{\beta c_i}$) (Equation 64). As in the articular contact calculation, the position of $p^{\gamma c_i}(u, v, a^{\gamma}, \theta^{\gamma})$ is unknown a priori, and it must be determined by solving equation (84). Since the contact point 4 on the secondary surface moves as body $\beta 2$ or body $\gamma$ moves, the point is located using parametric coordinates u and v along the surface. Moreover, unit normal $\hat{n}^{\gamma c_i}$ on the secondary surface also changes as the contact point 4 changes, and the normal must be calculated for each contact calculation.

The contact force 8 acting on body $\gamma$ is given by:

$$f^{\beta c_i} = F^{c_i}(t^{c_i}) \hat{n}^{\gamma c_i}, \tag{85}$$

where $F^{c_i}(t^{c_i})$ is a function relating the magnitude of contact force to the proximity $t^{c_i}$. Differentiating equation (85) with respect to vector x representing $a^{\beta}$, $a^{\gamma}$, or $\theta^{\gamma}$, $$\frac{\partial f^{\beta c_i}}{\partial x} = \hat{n}^{\gamma c_i} \frac{\partial F^{c_i}(t^{c_i})}{\partial x} + F^{c_i}(t^{c_i}) \frac{\partial \hat{n}^{\gamma c_i}}{\partial x} \tag{86}$$

$$= F^{c_i \prime} \hat{n}^{\gamma c_i} \frac{\partial t^{c_i}}{\partial x} + F^{c_i}(t^{c_i}) \frac{\partial \hat{n}^{\gamma c_i}}{\partial x},$$

where $F^{c_i}$. From equation (84), $$\frac{\partial t^{\beta c_i}}{\partial x} = \frac{\partial p^{\beta c_i}}{\partial x} - \frac{\partial p^{\gamma c_i}}{\partial x} = \hat{n}^{\gamma c_i} \frac{\partial t^{c_i}}{\partial x} + t^{c_i} \frac{\partial \hat{n}^{\gamma c_i}}{\partial x}. \tag{87}$$

Expanding $$\frac{\partial p^{\gamma c_i}}{\partial x} \text{ and } \frac{\partial \hat{n}^{\gamma c_i}}{\partial x}$$

in the above equation, $$\frac{\partial p^{\beta c_i}}{\partial x} - \frac{\partial p^{\gamma c_i}}{\partial u}\frac{\partial u}{\partial x} - \frac{\partial p^{\gamma c_i}}{\partial v}\frac{\partial v}{\partial x} - \left(\frac{\partial p^{\gamma c_i}}{\partial a^{\gamma}}\bigg|_{u,v}\right)\frac{\partial a^{\gamma}}{\partial x} - \tag{88}$$

$$\left(\frac{\partial p^{\gamma c_i}}{\partial \theta^{\gamma}}\bigg|_{u,v}\right)\frac{\partial \theta^{\gamma}}{\partial x} = \hat{n}^{\gamma c_i} \frac{\partial t^{c_i}}{\partial x} + t^{c_i}\left(\frac{\partial \hat{n}^{\gamma c_i}}{\partial u}\frac{\partial u}{\partial x} + \frac{\partial \hat{n}^{\gamma c_i}}{\partial v}\frac{\partial v}{\partial x} + \right.$$

$$\left. \left(\frac{\partial \hat{n}^{\gamma c_i}}{\partial a^{\beta}}\bigg|_{u,v}\right)\frac{\partial a^{\beta}}{\partial x} + \left(\frac{\partial \hat{n}^{\gamma c_i}}{\partial a^{\gamma}}\bigg|_{u,v}\right)\frac{\partial a^{\gamma}}{\partial x} + \left(\frac{\partial \hat{n}^{\gamma c_i}}{\partial \theta^{\gamma}}\bigg|_{u,v}\right)\frac{\partial \theta^{\gamma}}{\partial x}\right).$$

Note however that since unit normal $\hat{n}^{\gamma c_i}$ does not change with $a^{\beta}$ and $a^{\gamma}$ at fixed u and v, $$\frac{\partial \hat{n}^{\gamma c_i}}{\partial a^{\beta}}\bigg|_{u,v} = \frac{\partial \hat{n}^{\gamma c_i}}{\partial a^{\gamma}}\bigg|_{u,v} = 0.$$

Operating above equation by $\hat{e}_k^o$, a unit vector along the k-th axis of the global coordinate system, and substituting equations (1) and (27), $$\left[\frac{\partial p^{\beta c_i}}{\partial x} - \frac{\partial p^{\gamma c_i}}{\partial u}\frac{\partial u}{\partial x} - \frac{\partial p^{\gamma c_i}}{\partial v}\frac{\partial v}{\partial x} - \right. \tag{89}$$

$$\left. I\frac{\partial a^{\gamma}}{\partial x} + \mathcal{A}(p^{\gamma c_i} - a^{\gamma})Q(\theta^{\gamma})\frac{\partial \theta^{\gamma}}{\partial x}\right]\hat{e}_k^o =$$

$$\hat{n}^{\gamma c_i}\frac{\partial t^{c_i}}{\partial x}\hat{e}_k^o + t^{c_i}\left[\frac{\partial \hat{n}^{\gamma c_i}}{\partial u}\frac{\partial u}{\partial x} + \frac{\partial \hat{n}^{\gamma c_i}}{\partial v}\frac{\partial v}{\partial x} - \mathcal{A}(\hat{n}^{\gamma c_i})Q(\theta^{\gamma})\frac{\partial \theta^{\gamma}}{\partial x}\right]\hat{e}_k^o.$$

By using the relationship given in equation (71) and rearranging, $$\left(\frac{\partial t^{c_i}}{\partial x}\cdot\hat{e}_k^o\right)\hat{n}^{\gamma c_i} + \left(\frac{\partial u}{\partial x}\cdot\hat{e}_k^o\right)\left(t^{c_i}\frac{\partial \hat{n}^{\gamma c_i}}{\partial u} + \frac{\partial p^{\gamma c_i}}{\partial u}\right) + \tag{90}$$

$$\left(\frac{\partial v}{\partial x}\cdot\hat{e}_k^o\right)\left(t^{c_i}\frac{\partial \hat{n}^{\gamma c_i}}{\partial v} + \frac{\partial p^{\gamma c_i}}{\partial v}\right) = \left[\frac{\partial p^{\beta c_i}}{\partial x} - I\frac{\partial a^{\gamma}}{\partial x} + \right.$$

$$\left. \mathcal{A}(p^{\gamma c_i} - a^{\gamma})Q(\theta^{\gamma})\frac{\partial \theta^{\gamma}}{\partial x} + \mathcal{A}(\hat{n}^{\gamma c_i})Q(\theta^{\gamma})\frac{\partial \theta^{\gamma}}{\partial x}\right]\hat{e}_k^o.$$

where $\hat{n}^{\gamma c_i}$ is the surface normal, $$\frac{\partial p^{\gamma c_i}}{\partial u} \text{ and } \frac{\partial p^{\gamma c_i}}{\partial v}$$

are surface tangent vectors along u and v directions, and $$\frac{\partial \hat{n}^{\gamma c_i}}{\partial u} \text{ and } \frac{\partial \hat{n}^{\gamma c_i}}{\partial u}$$

are second derivatives (i.e., related to the curvatures) of the surface along u and v. All these vectors can be calculated from the analytical representation of the surface. Substituting $a^{\beta}$, $a^{\gamma}$, and $\theta^{\gamma}$ for x, from equations (1) and (27), the right-hand side of equation (90) becomes:

$$\hat{e}_k^o, \text{ when } x=a^{\beta}; \tag{91a}$$

$-\hat{e}_k^o$, when $x=a^\gamma$; (91a)

$[\mathbf{A}(p^{\gamma c_i}-a^\gamma)Q(\theta^\gamma)+\mathbf{A}(\hat{n}^{\gamma c_i})Q(\theta^\gamma)]\hat{e}_k^o$, when $x=\theta^\gamma$. (91c)

As in articular contact calculations, since the right-hand-side of equation (90) is known, the k-th component of $$\frac{\partial t^{c_i}}{\partial x}, \frac{\partial u}{\partial x} \text{ and } \frac{\partial v}{\partial x}$$

can be obtained by solving equation (90).

Finally, substituting the solutions of equation (90) into equation (86), $$\frac{\partial f^{\beta c_i}}{\partial a^\beta} = F^{c_i'}\hat{n}^{\gamma c_i}\frac{\partial t^{c_i}}{\partial a^\beta} + F^{c_i}(t^{c_i})\left(\frac{\partial \hat{n}^{\gamma c_i}}{\partial u}\frac{\partial u}{\partial a^\beta} + \frac{\partial \hat{n}^{\gamma c_i}}{\partial v}\frac{\partial v}{\partial a^\beta}\right) \quad (92a)$$

$$\frac{\partial f^{\beta c_i}}{\partial a^\gamma} = -\frac{\partial f^{\beta c_i}}{\partial a^\beta}, \text{ and} \quad (92b)$$

$$\frac{\partial f^{\beta c_i}}{\partial \theta^\gamma} = F^{c_i'}\hat{n}^{\gamma c_i}\frac{\partial t^{c_i}}{\partial \theta^\gamma} + \quad (92c)$$
$$F^{c_i}(t^{c_i})\left(\frac{\partial \hat{n}^{\gamma c_i}}{\partial u}\frac{\partial u}{\partial \theta^\gamma} + \frac{\partial \hat{n}^{\gamma c_i}}{\partial v}\frac{\partial v}{\partial \theta^\gamma} - \mathcal{A}(\hat{n}^{\gamma c_i})Q(\theta^\gamma)\right).$$

Therefore, the interaction between a particle and a surface is calculated using equations (85) and (92). Wrapping of a ligament or a tendon around a surface is approximated by linking particles with ligaments and letting these particles contact the surface. Multiple particles can be linked in series to simulate wrapping around a highly curved surface. Hence, while a tendon-pulley link connects tendons at specific points on a body, a particle contact link allows a ligament or tendon to contact a surface anywhere on the surface.

5.2.9 External Forces Link and Moments Link

All links described so far connect two or more bodies and generate forces and moments as a function of body poses. The multibody model also simulates external forces and moments 8 applied directly on the moving bodies as links. Two types of external forces 8 and moments 8 exist in the model (FIG. 8). External forces 8 and moments 8 can be fixed to the moving body ($\alpha=\epsilon$ for the force 8, and $\alpha=\eta$ for the moment 8); thus, the forces and moments move with the body. For these forces 8 and moments 8, the input must be given in the local body-fixed coordinate system 5. The other type of external forces 8 and moments 8 is fixed relative to the ground ($\alpha=e$ for the force, and $\alpha=h$ for the moment). These forces 8 and moments 8 do not move (e.g., gravity), and the input must be given in the global ground-fixed coordinate system 3.

Let $\phi^{\beta\epsilon_i}$ be the external force $\epsilon_i$ fixed to moving body $\beta$, applied at point $\pi^{\beta\epsilon_i}$ in the local moving-body coordinate system 5. Then repeating equation (5), the same force is given in the global coordinate system 3 as:

$$f^{\beta\epsilon_i}=R(\theta^\beta)\phi^{\beta\epsilon_i} \quad (5)$$

Differentiating the above equation with respect to $a^\beta$ and $\theta^\beta$, $$\frac{\partial f^{\beta\epsilon_i}}{\partial a^\beta} = 0, \text{ and} \quad (154a)$$

-continued $$\frac{\partial f^{\beta\epsilon_i}}{\partial \theta^\beta} = \frac{\partial [R(\theta^\beta)\phi^{\beta\epsilon_i}]}{\partial \theta^\beta} \quad (154b)$$
$$= -\mathcal{A}[R(\theta^\beta)\phi^{\beta\epsilon_i}]Q(\theta^\beta)$$
$$= -\mathcal{A}(f^{\beta\epsilon_i})Q(\theta^\beta).$$

Once $$\frac{\partial f^{\beta\epsilon_i}}{\partial a^\beta} \text{ and } \frac{\partial f^{\beta\epsilon_i}}{\partial \theta^\beta}$$

are calculated, $$\frac{\partial m^{\beta\epsilon_i}}{\partial a^\beta} \text{ and } \frac{\partial m^{\beta\epsilon_i}}{\partial \theta^\beta}$$

can be obtained from equations (24) and (31).

Similarly, let $\mu^{\beta\eta_i}$ represent pure external moment $\eta_i$ fixed to the moving body. Then in the global coordinate system, $$m^{\beta\eta_i}=R(\theta^\beta)\mu^{\beta\eta_i}. \quad (155)$$

Differentiating the above relationship, $$\frac{\partial m^{\beta\eta_i}}{\partial a^\beta} = 0, \text{ and} \quad (156a)$$

$$\frac{\partial m^{\beta\eta_i}}{\partial \theta^\beta} = -\mathcal{A}(m^{\beta\eta_i})Q(\theta^\beta). \quad (156b)$$

Note that since $f^{\beta\epsilon_i}$ and are functions of body $\beta$ only, $$\frac{\partial f^{\beta\epsilon_i}}{\partial a^\delta} = \frac{\partial f^{\beta\epsilon_i}}{\partial \theta^\delta} = \frac{\partial m^{\beta\eta_i}}{\partial a^\delta} = \frac{\partial m^{\beta\eta_i}}{\partial \theta^\delta} = 0, \text{ if } \delta \neq \beta. \quad (157)$$

Globally fixed external force $e_i$ and moment $h_i$ do not change as the local body moves. Hence, $$\frac{\partial f^{\beta e_i}}{\partial a^\delta} = \frac{\partial f^{\beta e_i}}{\partial \theta^\delta} = \frac{\partial m^{\beta h_i}}{\partial a^\delta} = \frac{\partial m^{\beta h_i}}{\partial \theta^\delta} = 0, \text{ for all } \delta. \quad (158)$$

However, for globally fixed external force $f^{\beta\epsilon_i}$ acting on body $\beta$ at point $p^{\beta\epsilon_i}$, moment $m^{\beta\epsilon_i}$ is given by:

$$m^{\beta\epsilon_i}=p^{\beta\epsilon_i}\times f^{\beta\epsilon_i}. \quad (8)$$

Let vector x represent $a^\beta$ or $\theta^\beta$. Then repeating equation (22), $$\frac{\partial m^{\beta e_i}}{\partial x} = \mathcal{A}(p^{\beta e_i})\frac{\partial f^{\beta e_i}}{\partial x} - \mathcal{A}(f^{\beta e_i})\frac{\partial p^{\beta e_i}}{\partial x}. \quad (22)$$

Hence, from equations (24) and (31)

$$\frac{\partial m^{\beta e_i}}{\partial a^\beta} = \mathcal{A}(p^{\beta e_i})\frac{\partial f^{\beta e_i}}{\partial a^\beta} - \mathcal{A}(f^{\beta e_i})\frac{\partial p^{\beta e_i}}{\partial a^\beta} \quad (159a)$$
$$= -\mathcal{A}(f^{\beta e_i}), \text{ and}$$

-continued $$\frac{\partial m^{\beta e_i}}{\partial \theta^\beta} = \mathcal{A}(f^{\beta e_i})\mathcal{A}(p^{\beta e_i} - a^\beta)Q(\theta^\beta).\quad(159b)$$

5.2.10 Constraint of any Degree of Freedom

The multibody model can also constrain any degree-of-freedom (DOF) of a moving body, and its constraint force can be calculated. Repeating equations (13), the model solves a system of nonlinear equations, $$f(q)=0,\quad(13)$$

where f is the generalized force vector, and q is the generalized DOF vector. The equation is solved iteratively by updating q with:

$$q \leftarrow q-dq,\ \text{where}\ Jdq=f.\quad(14)$$

If a DOF is constrained, then that component of q is known in advance; i.e., $q_k=q_k^o$, where $q_k^o$ is the constraint value. Since $q_k$ is known, d $q_k=0$, and there will be an additional constraint force acting along that DOF, such that:

$$f_k \rightarrow f_k + f_k^o,\quad(160)$$

where $f_k^o$ is a constraint force which is unknown a priori. Hence the generalized system of equations to be solved reduces to:

$$\begin{bmatrix} J_{11} & J_{12} & \cdots & J_{1k} & \cdots & J_{1n} \\ J_{21} & J_{22} & \cdots & J_{2k} & \cdots & J_{2n} \\ \vdots & \vdots & \ddots & \vdots & \vdots & \vdots \\ J_{kl} & J_{k2} & \cdots & J_{kk} & \cdots & J_{kn} \\ \vdots & \vdots & \cdots & \vdots & \ddots & \vdots \\ J_{nl} & J_{n2} & \cdots & J_{nk} & \cdots & J_{nn} \end{bmatrix} \begin{bmatrix} dq_1 \\ dq_2 \\ \vdots \\ 0 \\ \vdots \\ dq_n \end{bmatrix} = \begin{bmatrix} f_1 \\ f_2 \\ \vdots \\ f_k + f_k^0 \\ \vdots \\ f_n \end{bmatrix}.\quad(161)$$

For the k-th equation, $$J_{k1}dq_1+J_{k2}dq_2+\ldots+J_{kk}\times 0+\ldots+J_{kn}dq_n=f_k+f_k^o.\quad(162a)$$

For any other equation, $$J_{i1}dq_1+J_{i2}dq_2+\ldots+J_{i2}\times 0+\ldots+J_{in}dq_n=f_i,\ i\neq k.\quad(162a)$$

These equations can be rearranged such that $$J_{k1}dq_1+J_{k2}dq_2+\ldots-f_k^o+\ldots+J_{kn}dq_n=f_k\quad(163a)$$

$$J_{i1}dq_1+J_{i2}dq_2+\ldots+f_k^o\times 0+\ldots+J_{in}dq_n=f_i,\ i\neq k,\quad(163b)$$

where $f_k^o$ replaces d $q_k$ as an unknown in the system of equations. Thus, the updated Jacobian matrix will be:

$$\begin{bmatrix} J_{11} & J_{12} & \cdots & J_{1,k-1} & 0 & J_{1,k+1} & \cdots & J_{1n} \\ J_{21} & J_{22} & \cdots & J_{2,k-1} & 0 & J_{2,k+1} & \cdots & J_{2n} \\ \vdots & \vdots & \ddots & \vdots & \vdots & \vdots & \ddots & \vdots \\ J_{k-1,1} & J_{k-1,2} & \cdots & J_{k-1,k-1} & 0 & J_{k-1,k+1} & \cdots & J_{k-1,n} \\ J_{kl} & J_{k2} & \cdots & J_{k,k-1} & -1 & J_{k,k+1} & \cdots & J_{kn} \\ J_{k+1,1} & J_{k+1,2} & \cdots & J_{k+1,k-1} & 0 & J_{k+1,k+1} & \cdots & J_{k+1,n} \\ \vdots & \vdots & \ddots & \vdots & \vdots & \vdots & \ddots & \vdots \\ J_{nl} & J_{n2} & \cdots & J_{n,k-1} & 0 & J_{n,k+1} & \cdots & J_{nn} \end{bmatrix} \begin{bmatrix} dq_1 \\ dq_2 \\ \vdots \\ dq_{k-1} \\ f_k^0 \\ dq_{k+1} \\ \vdots \\ dq_n \end{bmatrix} = \begin{bmatrix} f_1 \\ f_2 \\ \vdots \\ f_{k-1} \\ f_k \\ f_{k+1} \\ \vdots \\ f_n \end{bmatrix}\quad(164)$$

Using the above equation, the constraint force can be calculated without increasing the size or complexity of the Jacobian matrix. Since $q_k=q_k^o$ is known, $q_k^o$ is used in all the calculations that require it, including the components of the Jacobian matrix and the generalized force vector. While this derivation was provided for the DOF vector $q_k$, it can be similarly performed for any of the sub components of $q_k$.

6.1 Three Dimensional Multibody Modeling

The model is intended to be a general interactive quasi-static three dimensional model. The model incorporates multiple material and particle bodies, and each body accommodates various link types, including ligament links, muscle links, tendon-pulley links, wrapping links, torsional spring links, articular contact surface links, particle contact surface links, and external forces links and external moments links. The bodies interact with each other through surface contacts, ligaments, tendons, and torsional springs. Complex bone and articular surfaces are accurately represented by either bilinear or triangular patches. Articular surfaces are modeled as deformable surfaces that contact each other, with the contact stress approximated by various functions of the surface overlap. The friction between surfaces is assumed to be negligible. Ligaments are modeled as line segments whose forces are linearly or nonlinearly dependent on their length, stretch, or strain. Constant loads are applied through tendons to simulate muscle force, and the tendons may loop through tendon pulleys connected to various bones (e.g., simulation of the flexor digitorum protundus tendon in finger joints). The model permits wrapping of the tendons and ligaments around bone and articular surfaces (e.g. the quadriceps tendon wrapping around the femoral trochlea) by imbedding particles in the ligaments and tendons; these particles are moving bodies that have only translational degrees-of-freedom (DOF), and by their contact with the surfaces, they redirect the ligaments and tendons. Torsional springs, both linear and nonlinear, can be added to resist rotation between two rotating bodies. In addition, external forces and moments can be applied to any of the bodies either in its body-fixed coordinate system, or in a global coordinate system (e.g., gravity). Finally, any translational or rotational DOF of any moving body may be optionally constrained.

FIG. 20 represents a flow chart of a non-limiting embodiment of a three dimensional multibody modeling software program in accordance with the present invention. The source code associated with the program illustrated in FIG. 20 is contained in the appended microfiche appendix. The program provides first for a user interface (13), wherein a user can interact with the model by loading data regarding the joint or joints to be analyzed. The user selects the joint or joints to be studied, and next inputs anatomical data regarding the bodies of the joint or joints (14). Such data may be patient specific or may be retrieved from a clinical database. In accordance with the present invention, the model may utilize any known method for quantitative assessment of the anatomy of articular surfaces and biomechanical testing of soft tissues. In a preferred non-limiting embodiment, data acquisition of the bodies of the knee joint can be achieved by the testing device disclosed in Gardner et al, ASME, BED Adv. Bioeng. 28:279–280 (1994). In a preferred non-limiting embodiment, the data acquisition instrumentation acquires data through the use of an anatomically based coordinate system, which is purely based on the geometry of the bodies. Such a system is set forth in Blankevoort et al., European Society of Biomechanics 10:260 (1996) or Kwak et al, ASME BED Adv. Bioeng. 31:309–310 (1995). Once the data is acquired, it is acquired by the software program by inputting it along with the default parameters for the bodies of the selected joints.

At a second user interface (15), the user then can make a selection of the link types (17) associated with the joint or joints selected. The user also has the option of constraining any degree of freedom of any of the bodies (16). Next the user can make a selection of the link characteristics for each of the selected links (18). Each link type may have one or more parameters that may be varied in order to study the resulting effect on the three dimensional modeled joint or joints. Next the program generates Jacobian matrices for each of the link parameters by way of an analytical method (18). Then the program generates a Jacobian matrices for all of the links in combination (20). The program solves for an equilibrium condition (21), and iteration occurs, requiring the updating of the Jacobian matrices for all links in combination, until convergence to the equilibrium solution is achieved. Once convergence is achieved, then the output is illustrated to the user (22) in a graphical form. In a preferred non-limiting embodiment, the output is a three dimensional image of the joint or joints, illustrating all of the material and particle bodies, and all of the selected link types having the selected link characteristics. The three dimensional representation of the anatomical joint may appear on a two dimensional screen, but the visual image or images appear three dimensional to the user. Further, when rotated on such a two dimensional screen, the visual image or images of the three dimensional representation maintain a three dimensional appearance of the anatomical joint. At this junction, the user can return to the second user interface (15) and alter the link selections and degrees of freedom choices. After modifications are made to the link characteristics, the program will generate the Jacobian matrices and solve for equilibrium. The user is then presented with a new output of a three dimensional representation of the altered joint or joints. In a preferred non-limiting embodiment, the output is displayed as a three dimensional image of the joint or joints, illustrating all of the alterations of the material and particle bodies, and the selected links. The output can be printed or stored in a computer readable form (23).

6.2 Three Dimensional Multibody Modeling System

A three dimensional multibody model system, having a graphical user interface 24, is useful in order to make the model easy to use by surgeons and other medical professionals. The user can readily manipulate images of the multibody joint, or joints, with all surfaces, ligaments and tendons clearly displayed. One of the advantages of the present invention is the tremendous decrease in the amount of time required to perform a model simulation, such as modeling the effect of a tibial tuberosity transfer on the patellofemoral contact which can now be performed in a matter of minutes. Because of the model's complexity and detailed three dimensional computer graphics capability, it is preferred that a dual CPU Silicon Graphics Octane Workstation be used to perform these functions in near real time, yielding results much faster and making the model much more attractive for use by orthopaedic surgeons.

The model program can calculate the poses of moving bodies satisfying the static equlibrium condition, using the Newton-Raphson iterative method. The Jacobian matrix needed for the calculation was analytically derived for each link in the above sections and these derivations were coded into the model program. In addition to the poses of moving bodies, the program predicts forces and moments due to various links, and contact areas and pressure. The three dimensional modeling software program provides a graphical interface for users to interact with the model at a user workstation.

To provide a convenient means for users to interact with the model, the software program may be implemented in a graphical window environment using OSF/Motif subroutines (Open Software Foundation, Cambridge, Mass.). This environment enables users to choose a menu item in the program by simply pointing and selecting it (FIG. 9). Within this window environment, the program displays and provides for manipulation a three-dimensional representations of the model using Open Inventor subroutines (Silicon Graphics, Inc., Mt. View, Calif.). Open Inventor is a general graphics subroutine library which in turn calls OpenGL graphics subroutines (Silicon Graphics, Inc., Mt. View, Calif.). These graphics subroutines display sophisticated three-dimensional graphics and manage user interaction with three-dimensional objects. The program updates the graphics after any input modification or solution convergence, enabling users to visually check the model (FIG. 9). Users can translate or rotate the model to view it from different directions. Furthermore, users can open another sub-window to view a single bone displaying contact area or pressure maps inside the joint, unobstructed by other bones (FIG. 10).

The input file for the model contained geometric entities, link parameters, and initial poses. Geometric entities included bone geometry and articular surface geometry, as well as insertion locations for ligaments and tendons. Link parameters included reference length/angle/strain, material properties, and applied forces or moments. The geometric and link data, were mapped into a data set in the program to easily refer to a specific entity or link and identify all bodies or links affected by it. The input file included initial kinematic translation and rotation of all moving bodies, and the user can also fix any of these translational or rotational DOF components. While running the program, the user can interactively modify various geometric, link, and kinematic parameters, and investigate how these parameters affect and change the kinematics, contact, and internal forces in the joint.

The computer program was implemented on a Silicon Graphics Indigo$^2$ IMPACT R10000 workstation (Silicon Graphics, Inc., Mt. View, Calif.). Although the calculation time depends on the complexity of the model and the computer speed, running the program on the Silicon Graphics workstation demonstrated convergence to an equilibrium solution less then ten seconds for most analyses of the patellofemoral joint. Such calculation speed allows a user to truly interact with the model while sitting in front of the computer.

The present invention maybe embodied in a graphically based user interface to perform pre- and post-processing to facilitate model setup, use and interpretation of results. High level graphic user interfaces on Silicon Graphics Octane Workstation(TM) make the model easy to use by surgeons and other medical professionals. The user can readily manipulate images of the multibody joint, with all surfaces, ligaments and tendons clearly displayed. Every effort was made to minimize the amount of computational resources required of the computer model to provide a rapid demonstration of the results.

In a non-limiting example, the particular workstation specifications include dual R10000 64-bit 185 MHZ processors, 256 MB RAM, 4- and 9 GB disk drives, 4 mm DAT drive, CD-ROM Drive, Dial/buttons box, 20" high resolution color monitor, network interface, Silicon Graphics Desktop graphics acceleration subsystem, and the MXI, which includes two hardware geometry engine processors, two raster engines, dedicated frame buffer memory tuned for three dimensional images and texture caching memory, and a full-performance texture subsystem.

7. MODEL VALIDATION

7.1 Example: Patellofemoral Joint Modeled

The three dimensional multibody model was applied and validated for the patellofemoral joint by comparing model predictions to actual experimental results. For purposes of validation against experimental data, only the patellofemoral joint was modeled, including articular surfaces, bone surfaces, the patellar ligament, and different components of the quadriceps muscle. Other structures such as capsular structures and fat pads were thought to be of secondary importance for a normal patellofemoral joint, and were not simulated. Therefore, this validation study measured the accuracy of an approximate model, with assumptions general to the multibody model and specific to the patellofemoral joint simulation.

Figure 11:
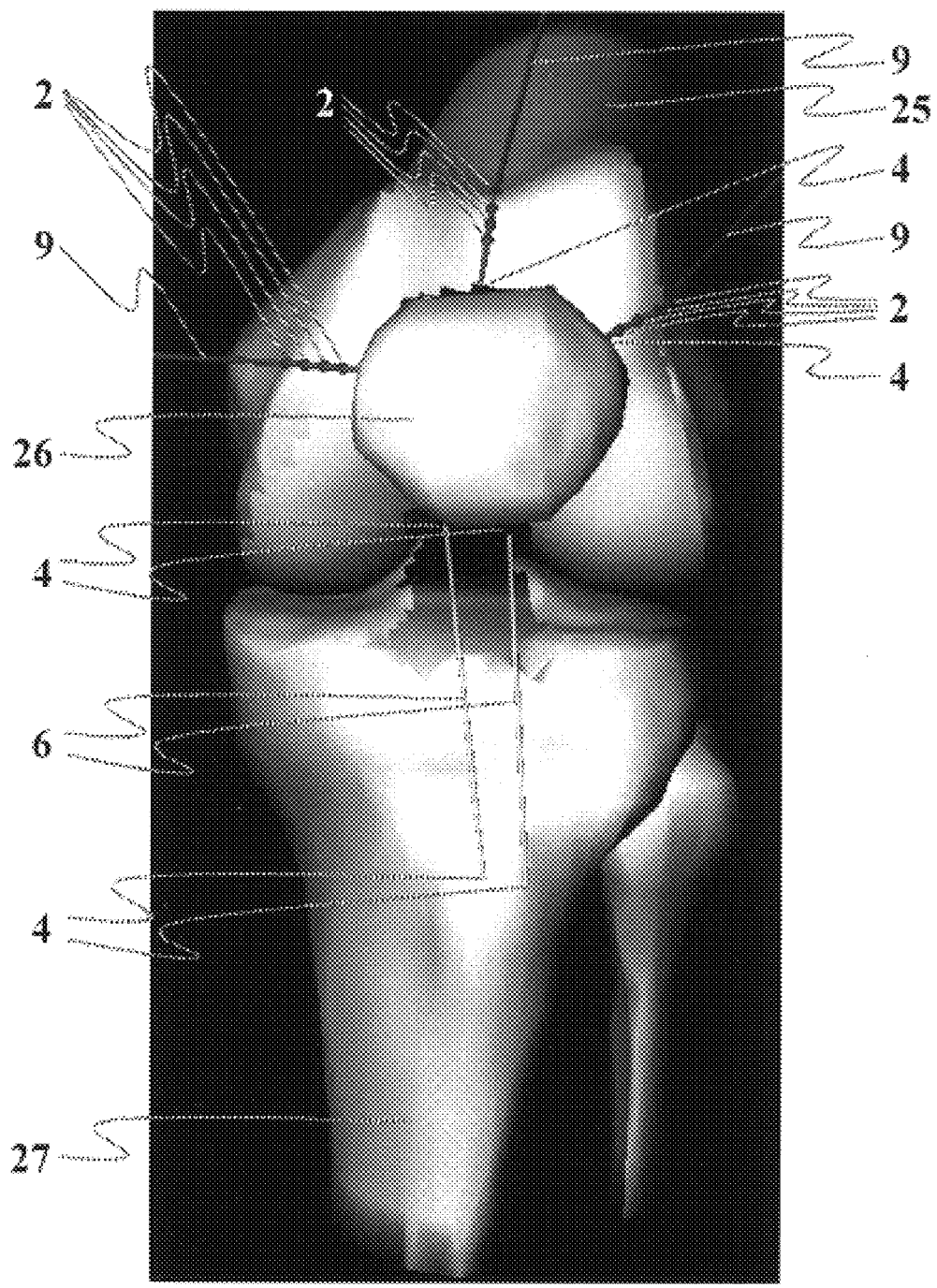
Figure 11:
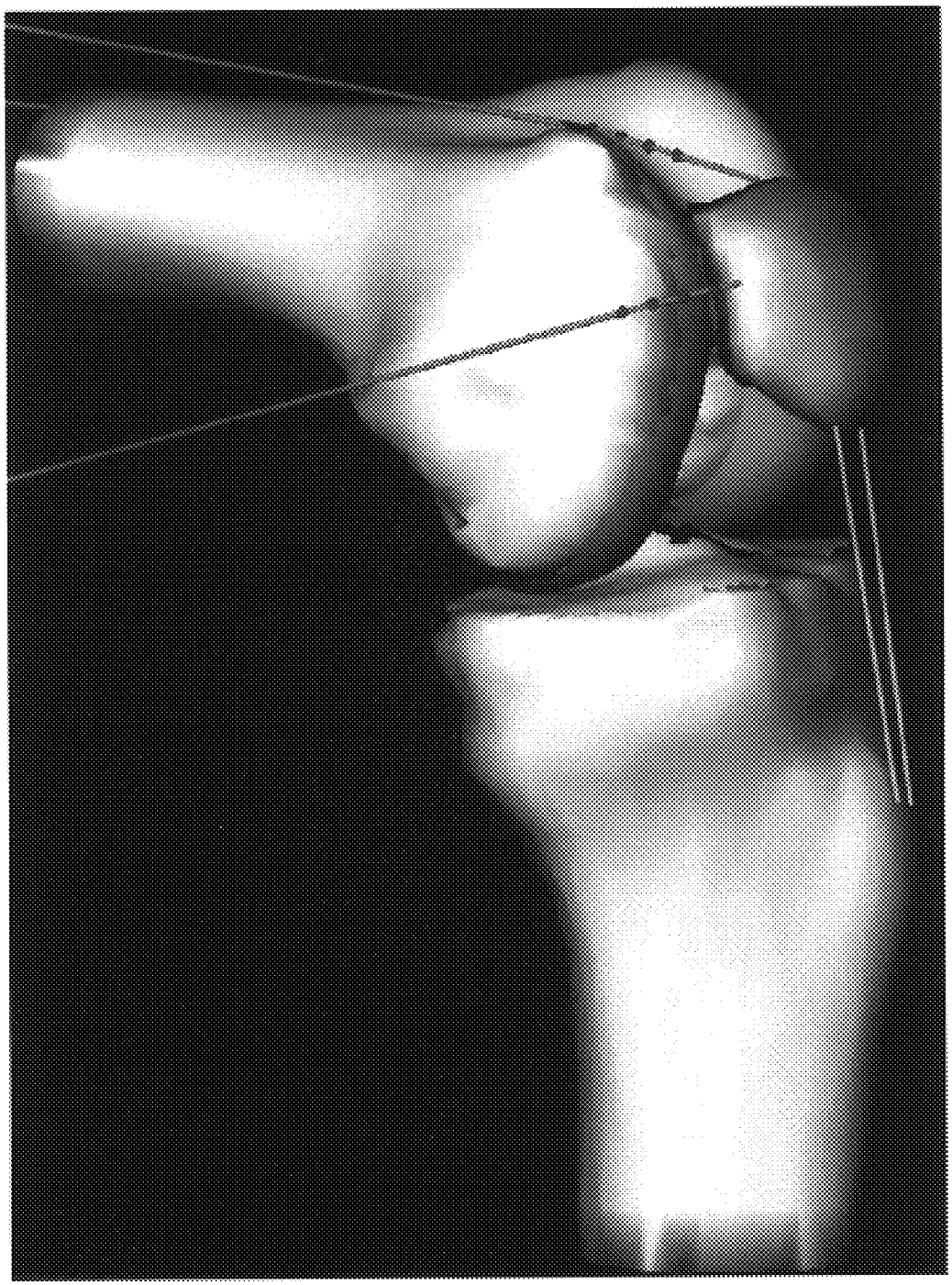
Figure 11:
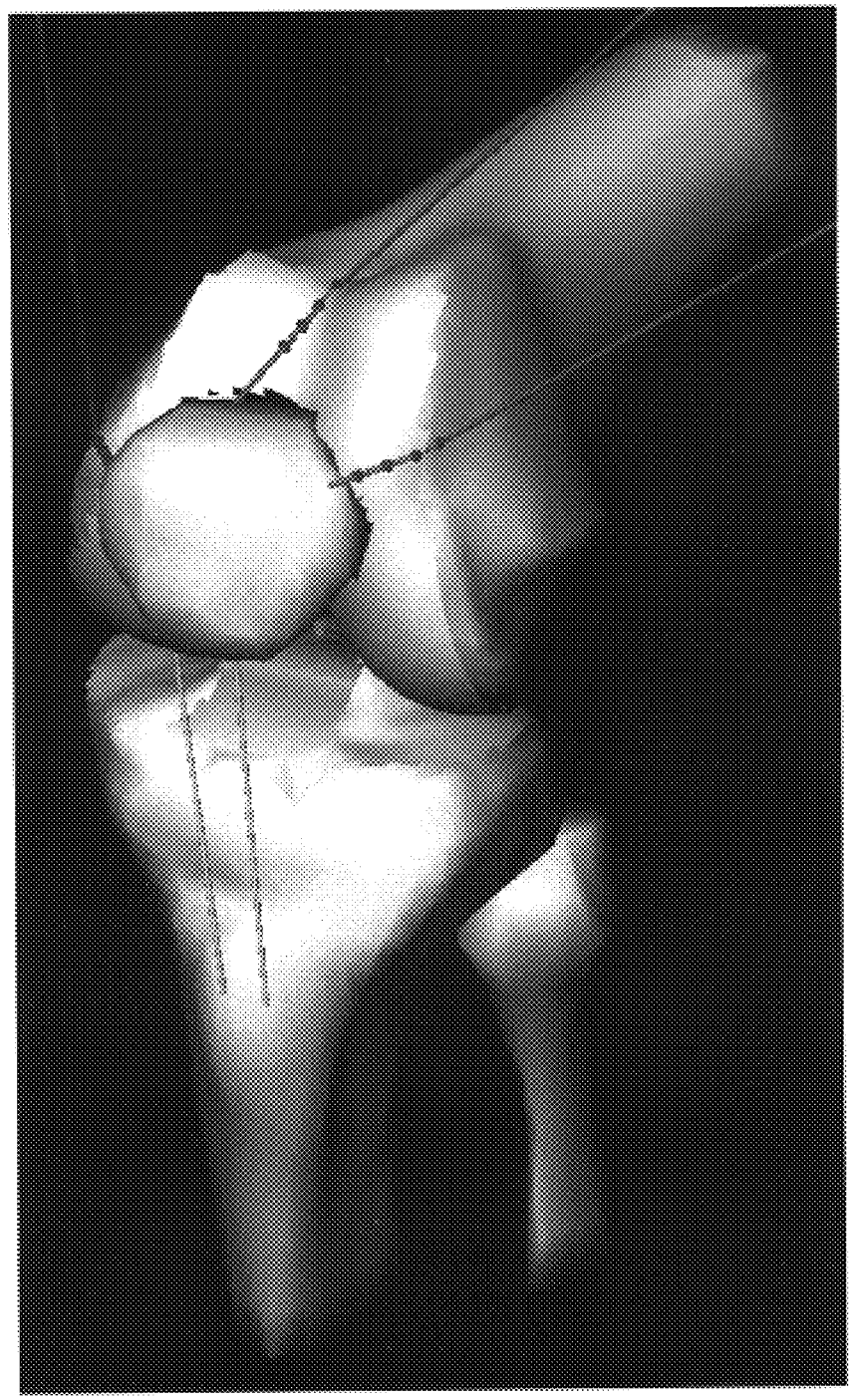
Figure 12:

The model was validated by re producing results of six cadaveric knee joint experiments (ages 49–89, avg. 65 years old). Each knee was dissected free of all skin and muscles leaving the joint intact with its ligamentous, tendinous, and capsular structures. The knee was loaded by simulating three components of quadriceps muscles: rectus femoris+vastus intermedius+vastus medialis longus (267N), vastus lateralis (178N), and vastus medialis ovliquus (VMO)(89N). The pose of the material bodies, the femur 25, patella 26, and tibia 27 were obtained by digitizing two sets of triads rigidly attached to each bone with a coordinate measuring machine (CMM, 50 µm). The knees were tested at 30°, 45°, 60°, and 90° of knee flexion in an open chain configuration; 0° to 20° flexion range was avoided since there was no patellofemoral articular contact in this range in many of the knees. After obtaining the kinematic data, the muscle and ligament insertions, and bone surface geometries were measured using the CMM, and the articular surface topographies were obtained using a stereogrammetric methods (90 µm accuracy). The model was used to simulate the experiments using the experimentally derived geometric data and muscle forces as the inputs to the model. Ligament and cartilage material properties were similar to those in previous knee joint models. The patellar ligament was simulated by two elastic line elements 6 on the medial and lateral side. (FIG. 11). The contours of the patellar ligament insertions 4 on both the tibia 27 and patella 26 were cut in half at the geometric center of each contour along the plane perpendicular to the medial-lateral anatomic axis of each bone. From each halves, the geometric center of the remaining contour was calculated again, and these points 4 served as insertions of the medial and lateral line elements representing the patellar ligament. The initial length of the patellar ligament was approximated as an average of patellar ligament length over all flexion angles calculated from one insertion to the other. As a first approximation, a spring constant of 1000 N/cm was used for each line segment representing the patellar ligament. A constant thickless of 5.0 mm (combined thickness of opposing layers) was assumed throughout the articular cartilage surface, and the cartilage modulus was approximated to be 2.0 MPa. To simulate wrapping of the quadriceps tendons around the femur, four particles bodies 2 were imbedded into each of the three components of the quadriceps muscle 9 (FIG. 11). These particles 2 were moving bodies capable of contacting both the femoral cartilage surface and the bone surface. In this study, the femur 25 was fixed, the position of the tibia 27 was prescribed from the experiment, and the patella 26 and particles 2 were free to move in any direction, bringing the total number of moving bodies to thirteen.

Five of six distinct patellofemoral joints modeled in this study are shown in FIGS. 12A–E. The average and the standard deviation of the differences in translation and rotation of the patella relative to femur 25 between the model and experiment are reported in Tables 1 and 2. In the model, the patella 26 translated 0.63 mm more medially and 0.29 mm more posteriorly on average when compared to the experiment. The standard deviations of the translation differences were all less than 1.6 mm. In rotation, the model exhibited 1.41° more extension, and 1.13° more medial rotation on average. The highest standard deviation of 2.8° was found in the lateral tilt at 45° knee flexion. At 90° knee flexion, the model predicted wrapping of the quadriceps tendon around the femur, redirecting the muscle force for all knees except one (FIG. 11). FIG. 13 shows an example of contact areas predicted by the model and experiment from a typical knee at 45° knee flexion.

The results of the comparison between the model and experimental data demonstrate the capability and accuracy of the model. Only a small number of structures thought to be essential for modeling the patellofemoral joint were simulated, and as a first order approximation, ligaments and cartilage were simplified as linearly elastic materials. Yet, the mathematical model produced a good prediction with the translation of the patella within 2 mm and rotation within 3°, as seen in Tables 1 and 2.

TABLE 1

| Flexion Angle | Translation Error (mm) | | |
|---|---|---|---|
| | med-lat | prox-dist | ant-post |
| 30 | 1.14 ± 1.60 | 0.43 ± 0.33 | −0.51 ± 1.16 |
| 45 | 0.69 ± 1.21 | −0.21 ± 0.92 | −0.25 ± 0.89 |
| 60 | 0.45 ± 0.91 | 0.27 ± 0.78 | −0.12 ± 0.91 |
| 90 | 0.15 ± 0.97 | −0.14 ± 0.59 | −0.26 ± 0.30 |
| average | 0.63 ± 1.19 | 0.10 ± 0.71 | −0.29 ± 0.84 |

TABLE 2

| Flexion Angle | Rotation Error (deg) | | |
|---|---|---|---|
| | patella flexion | tilt | rotation |
| 30 | −1.31 ± 2.66 | −1.05 ± 2.66 | −1.52 ± 1.17 |
| 45 | −1.47 ± 1.74 | −0.40 ± 2.78 | −0.06 ± 2.54 |
| 60 | −1.00 ± 1.38 | 0.06 ± 2.30 | −1.45 ± 1.33 |
| 90 | −1.95 ± 0.72 | 0.26 ± 2.29 | −1.57 ± 2.00 |
| average | −1.41 ± 1.71 | 0.27 ± 2.38 | −1.13 ± 1.83 |

The contact are a prediction also showed good results as demonstrated in FIG. 13. The computer model predicted additional data such as contact force and ligament force that were not measured during the experiment. The model prediction may further improve by better approximation of material properties and by inclusion of other structures such as capsular retinaculum.

Others investigators that have simulated the patellofemoral joint using a three-dimensional model without the wrapping of tendons and with only a single muscle force. Further the model converges very rapidly by using an analytical Jacobian formulation. Further, the present model simulates deformation of articular surfaces during contact by allowing two rigid mathematical surfaces to overlap each other. Hence the present model predicted not only the contact force but contact areas within the joint. Furthermore, while all three previous models simulated the quadriceps tendon as a single muscle, the present model simulated the quadriceps with three muscle components. By separating the muscle, effects of different distributions of muscle forces can be investigated. As an example, dystrophy or weakening of the vastus medialis obliquus, a common patellofemoral pathology, can be simulated by simply reducing the force on that muscle. The vastus medialis obliquus is thought to be an important stabilizer of the patella, that prevents the patella from tracking laterally. FIG. 14 shows the effect of removing the vastus medialis obliquus force on the patellar contact area, demonstrating the ability of the present model to simulate different muscle components and predict changes in the contact areas.

The present model applied a simpler and faster method by imbedding moving particles 2 in the quadriceps tendon 9. These particles 2 contacted the surface and redirected the components of the quadriceps tendon 9 around the femur 25 (FIG. 11).

Therefore, the present model predicted the mechanical behavior of the patellofemoral joint with a good accuracy compared to the experimental results.

7.2 Example: Simulation of Tibial Tuberosity Transfer Modeled

To demonstrate the surgical simulation capability of this multibody model, elevation of the tibial tuberosity, a common knee surgical procedure, was simulated using the model. Elevation of the tibial tuberosity was introduced to alleviate patellar pain by surgically altering the patellofemoral mechanics. In a similar surgical procedure, the tuberosity is transferred both anteriorly and medially. Many experimental and theoretical studies confirm that these procedures involving elevation of the tibial tuberosity decrease contact force. However, when contact stress is examined, clinical studies report mixed results: some studies report that these surgical procedures are satisfactory with a success rates of 80% or higher, and others report less satisfactory results with success rate of less than 80%. The reason for these conflicting results may be caused by differences in the joint anatomy among patients. Although the total contact force decreases with the tuberosity elevation, the size of the contact area may also decrease. Hence, while the surgical procedure attempts to reduce contact stress, depending on the interplay between the contact force and area, the contact stress may increase or decrease. Using the multibody model, this study the effect of tibial tuberosity transfer on contact force, area, and stress for five different cadaver knees was simulated and investigated.

Surgical procedures were simulated with the multibody model on five cadaveric patellofemoral joints. Tibial tuberosity transfer was simulated by simply translating the distal insertions 4 of the patellar ligament along the anatomical direction defined in the tibial anatomic coordinate system (FIG. 15). Four surgical procedures were simulated: 15 mm and 25 mm anterior advancement of the tibial tuberosity, following the values suggested by Maquet, Clin. Orthop. 115:225–230 (1976), and 8.8 mm and 14.8 mm anterior advancement, both combined with 8.4 mm medial translation of the tibial tuberosity as suggested by Fulkerson et al. Am. J. Sports Med. 18:490–496 (1990). The same protocol used in the validation study was followed except for varying the location of patellar ligament insertion 4 on tibia 27 as per the above specifications. The knees were tested at 30°, 45°, and 60° knee flexion angles. Hence, in addition to the control, a total of 60 cases were tested (five knees, three flexion angles, four surgical procedures).

In all cases, the magnitude of the patellofemoral contact force decreased with tibial tuberosity transfer; the decrease was greater for higher elevation. In 56 of the 60 case, the contact area also decreased. FIG. 21 shows the change in contact area due to the 25 mm Maquet procedure with average values for the unoperated case as follows: 3.3+/–0.5 $cm^2$ for 30°, 4.9+/–0.5 $cm^2$ for 45° and 5.9+/–1.0 $cm^2$ for 60°. In many of the cases, however, the contact area also decreased, and the contact stress showed mixed results. For the Maquet procedures, average stress, total contact force divided by contact area, decreased for all three angles of three of the knees, decreased for two of three angles of the fourth knee, and increased for all angles of the last knee (FIG. 16). The average stress showed a greater decrease at the lower flexion angles (FIG. 16). No general pattern was found with Fulkerson procedures. The change in peak stress correlated with the change in average stress for all but two of the 60 cases. Examining the shift of the contact area, anterior transfer of the tibial tuberosity without medial transfer (Maquet procedure) led to a medial shift in the centroid of the contact area in all but six of 30 cases; five of which were from the same knee (FIG. 17). Anterior transfer of the tuberosity accompanied by medial transfer (Fulkerson procedure) led to a medial shift of the contact area for all 30 cases.

Although anterior elevation combined with or without medial transfer of the tibial tuberosity decreased contact force for all knees, the contact stress decreased consistently only in three of the five knees. If the aim of these surgical procedures is to reduce contact stress this simulation demonstrates that the success may be patient specific, and it may explain conflicting clinical outcomes. Furthermore, anterior elevation of the tibial tuberosity alone shifted the contact area medially, suggesting that medial transfer of the tuberosity may not be necessary to shift the contact area.

Valuable results were obtained from this surgical simulation study using a multibody model. The model was validated experimentally for the control case, and the perturbation involved were sufficiently small to assume its validity for surgical simulations.

7.3 Example: Adhesions of the Patellar and Quadriceps Tendons Modeled

In another non-limiting example of the present multibody model, a post-surgical pathology was simulated. Following knee surgery, often after anterior cruciate ligament (ACL) reconstruction, patients complain about a significant decrease in patellar mobility accompanied by anterior knee pain, sometimes severe. A few investigators have indicated that these symptoms may be caused by fibrous adhesion of the patellar tendon to the anterior aspect of the tibia and by formation of fibrous tissue between the quadriceps tendon and the femur. Others attributed the tendon adhesion to the scarring of infrapatellar and suprapatellar fat pad caused by the surgery. While these adhesions may be important clinical problems associated with knee surgery, no study to date has quantitatively investigated the effect of these adhesions on knee kinematics and contact forces. The effects of patellar tendon adhesion to the anterior tibia, as well as quadriceps tendon adhesion to the anterior femur, were studied using the multibody mathematical model. The objective was to demonstrate the effects of these types of post-operative adhesions on patellofemoral joint mechanics.

Three different knees from the validation study (Section 7.1 above) were simulated to study the effects of patellar and quadriceps tendon adhesion. To simulate the adhesion of the patellar tendon to the anterior portion of the tibia, fibrous tissue connecting the tendon to the tibia was modeled as an elastic element 6 connecting the tendon to the anterior tibia 27. To study progressive adhesion of the patellar tendon superiorly along the tibia, three different locations of the adhesion were simulated: adhesion occurring at 15 mm (PA1) from the patellar tendon insertion 4 on the tibia 27, at 21 mm (PA2), and at 27 mm (PA3) (FIGS. 18 and 19). Furthermore, variation in the stiffness of the fibrous tissue was studied parametrically with the various values of the stiffness given by: 100, 200, 400, and 800 N/mm, respectively. The fibrous connection (9A) between the quadriceps tendon and the anterior femur was also simulated by two elastic elements 6 connecting the central part of the quadriceps tendon to the femur (FIG. 18). Again, the effects of fibrous tissue stiffnesses were studied parametrically with stiffness values of 10, 20, 40, 80, 160, 320, and 640 N/mm. The limitation of patellar mobility due to stretching of the fibrous tissue connecting the quadriceps tendon to the femur was simulated by arbitrarily limiting the force of the fibrous connection to 600 N. The knees were tested at 20°, 30°, 45°, 60°, and 90° knee flexion.

The three dimensional multibody simulation of the patellar and quadriceps adhesion demonstrated significant effects of the adhesions on patellofemoral mechanics. FIG. 19A shows the effects of different locations of the patellar tendon adhesion to the anterior tibia (fibrous tissue stiffness of 800 N/mm). As the adhesion occurred more superiorly toward the patella, the patellar contact force increased. FIG. 19B demonstrates the effect of different stiffness of the fibrous connection between the patellar tendon and the tibia. As expected, the patellar contact force increased along with the stiffness. Both FIGS. 19C and 19B show that the effect of patellar adhesion was greatest near full extension of the knee, and this effect decreased with knee flexion. For the quadriceps tendon adhesion, FIG. 19A shows how the patellar contact force increases as the fibrous tissue stiffness increases. Since the stretching of the fibrous tissue will prevent the knee from flexing further, FIG. 19C plots results up to a fibrous connection force of 600 N. With the adhesion of the quadriceps tendon, the patellar contact force increased dramatically as the knee flexed.

The results of this study show that adhesion of the quadriceps tendon on the femur had a large effect on the patellofemoral contact force. Even weak adhesions will dramatically increase this contact force. As expected, this effect increases as knee flexion is increased. As the stiffness of the fibrous connection increases, the tension generated in the adhesions will prevent the knee from further flexion. On the patellar tendon side, the effect of adhesion was greatest near full extension. As the mechanical stiffness of the adhesions increased, and as the location of the adhesions progressed more superiorly, the patellar contact force increased. The contact force significantly increased at low flexion angles for the patellar tendon adhesion and significantly increased at high flexion angles for the quadriceps tendon adhesion. Such increases in the contact force at the articulating surfaces may be a source of anterior knee pain seen clinically.

8. MODEL APPLICATIONS

Many applications exist for this three dimensional multibody model. One of the greatest potential uses of the model is in surgical simulation. Different surgeries can be planned, performed and their effectiveness can be evaluated using the model. The model may even be used to optimize the surgery to produce the best outcome. A surgeon can select an optimization parameter such as reduction in contact stress or contact force, translation of contact area to an area of healthy cartilage, or restoration of normal joint kinematics for one or more joints. With improving non-invasive in vivo imaging technologies such as CT and MRI, it may be possible to obtain geometric data needed for the model directly from patients. Already several investigators have reconstructed cartilage topography and thickness from MR images. Once the patient joint geometry is obtained, a patient specific model can be constructed and analyzed to suggest a best physical therapy program or a surgical procedure. One of the advantages of the multibody model is its rapid convergence by using an efficient analytical Jacobian formulation and contact calculation. It also provides sophisticated interactive graphics to view the three-dimensional model, and menu-driven windows to easily modify model parameters. Through all these features, the model allows a user to interactively modify different geometric and structural parameters, and observe the effects of these parameters almost immediately. The user can explore various parameters efficiently and quantify their mechanical effects on the joint.

This three dimensional software multibody model has been derived and written in a very general way to simulate different joints and accommodate a variety of anatomical structures. Different contact, ligament, tendon, and spring functions can be easily added to the model without altering the general program. The contact between articular surfaces was modeled by two rigid surfaces penetrating each other, simulating articular surface deformation. Hence, the contact analysis provided an approximation of contact areas and contact stresses based on surface overlap. The contact overlap calculation is a full three-dimensional vector calculation, enabling calculation of contact between any two arbitrarily shaped surfaces. Furthermore, ligaments or tendons wrapping around a surface are simulated by embedding moving particles in the ligament or tendon. The multibody model simplifies wrapping as contact between particles and surfaces, yet it predicts changes in the ligament or tendon direction and contact force due to wrapping. The multibody model has improved upon the previously described models by its ability to model any number of moveable bodies.

We claim:

1. A method of generating a three dimensional representation of an anatomical joint on an output device, wherein said representation comprises two or more movable bodies and one or more links, comprising the steps of:

acquiring anatomically representative data of two or more movable bodies of a selected joint;

selecting one or more link types responsive to said representative data of the bodies;

selecting link characteristics responsive to each selected link type;

generating an equilibrium condition responsive to interaction between the bodies and the one or more links; and displaying a three dimensional representation on the output device of said anatomical joint responsive to the data generated from the equilibrium condition of said anatomical joint.

2. A method of generating a three dimensional representation of more than one anatomical joint on an output device, wherein said representation comprises two or more movable bodies and one or more links associated with the selected number of joints, comprising the steps of:

acquiring anatomically representative data of two or more movable bodies of a selected number of joints;

selecting one or more link types responsive to said representative data of the bodies for each of the selected number of joints;

selecting link characteristics responsive to each selected link type;

generating an equilibrium condition responsive to interaction between the bodies and the links; and displaying a three dimensional representation of said anatomical joints on the output device responsive to the data generated from the equilibrium condition for the selected number of joints.

3. A method according to claims 1 or 2, wherein the data generated from the equilibrium condition responsive to interaction between the bodies and links predicts the kinematic orientation, the kinematic position, the contact force, and the contact area of the movable bodies and links.

4. A method according to claims 1 or 2, wherein the one or more link types is selected from the group consisting of ligament links, muscle links, tendon-pulley links, wrapping links, torsional spring links, articular contact links, particle contact links, external forces links, and external moments links.

5. A method according to claims 1 or 2, wherein the one or more movable bodies are selected from the group consisting of material bodies or particle bodies.

6. A method according to claims 1 or 2, further comprising the step of constraining one or more degrees of freedom of one or more movable body, prior to the step of selecting link characteristics responsive to each selected link type.

7. A system for generating a three dimensional representation of an anatomical joint, wherein said representation comprises two or more movable bodies and one or more links, comprising means for providing a user interface;

means for acquiring anatomically representative data of two or more movable bodies of a selected joint;

means for selecting one or more link types responsive to said representative data of the bodies;

means for selecting link characteristics responsive to each selected link type;

means for generating an equilibrium condition responsive to interaction between the bodies and the one or more links; and means for displaying a three dimensional representation of said anatomical joint responsive to the data generated from the equilibrium condition of said anatomical joint.

8. A system for generating a three dimensional representation of more than one anatomical joint, wherein said representation comprises two or more movable bodies and one or more links associated with the selected number of joints, comprising means for providing a user interface;

means for acquiring anatomically representative data of two or more movable bodies of a selected number of joints;

means for selecting one or more link types responsive to said representative data of the bodies for each of the selected number of joints;

means for selecting link characteristics responsive to each selected link type;

means for generating an equilibrium condition responsive to interaction between the bodies and the links; and means for displaying a three dimensional representation of said anatomical joints responsive to the data generated from the equilibrium condition for the selected number of joints.

9. A system according to claims 7 or 8, wherein the data generated from the equilibrium condition responsive to interaction between the bodies and links predicts the kinematic orientation, the kinematic position, the contact force, and the contact area of the movable bodies and links.

10. A system according to claims 7 or 8, wherein the one or more link types is selected from the group consisting of ligament links, muscle links, tendon-pulley links, wrapping links, torsional spring links, articular contact links, particle contact links, external forces links, and external moments links.

11. A system according to claims 7 or 8, wherein the one or more movable bodies are selected from the group consisting of material bodies or particle bodies.

12. A system according to claims 7 or 8, further comprising means for constraining one or more degrees of freedom of one or more movable body, prior to selecting link characteristics responsive to each selected link type.

13. A method of planning surgery of an anatomical joint comprising the steps of:

acquiring, from a subject for whom surgery is being planned, anatomically representative data of a selected joint having two or more bodies and one or more links;

selecting one or more link types responsive to said representative data of the bodies;

selecting link characteristics responsive to each selected link type;

generating an equilibrium condition responsive to interaction between the bodies and the one or more links; and displaying a three dimensional representation on an output device for planning surgery of said anatomical joint responsive to the data generated from the equilibrium condition of said anatomical joint.

* * * * *

UNITED STATES PATENT AND TRADEMARK OFFICE
CERTIFICATE OF CORRECTION

| | | |
|---|---|---|
| PATENT NO. | : 6,161,080 | |
| APPLICATION NO. | : 08/972160 | |
| DATED | : December 12, 2000 | |
| INVENTOR(S) | : Gerard H. Aouni-Ateshian et al. | |

It is certified that error appears in the above-identified patent and that said Letters Patent is hereby corrected as shown below:

On page 1, Column 1, line 3, please insert the following header and paragraph:

--Statement Regarding Federally Sponsored Research or Development
This invention was made with government support under grant number ASC9318184 awarded by the National Science Foundation. The government has certain rights in the invention.--

Signed and Sealed this
Thirteenth Day of November, 2012

David J. Kappos
*Director of the United States Patent and Trademark Office*